United States Patent
Leubitz et al.

(10) Patent No.: US 11,191,848 B2
(45) Date of Patent: *Dec. 7, 2021

(54) METHODS OF INDUCING RESPONSIVENESS TO ANTI-ANGIOGENIC AGENT

(71) Applicant: Vascular Biogenics Ltd., Modiin (IL)

(72) Inventors: Andrea Rachel Leubitz, Efrat (IL); Naamit Sher, Rechovot (IL); Erez Feige, Hemed (IL); Eyal Breitbart, Hashmonaim (IL)

(73) Assignee: Vascular Biogenics Ltd., Modiin (IL)

( * ) Notice: Subject to any disclaimer, the term of this patent is extended or adjusted under 35 U.S.C. 154(b) by 167 days.

This patent is subject to a terminal disclaimer.

(21) Appl. No.: 16/505,130

(22) Filed: Jul. 8, 2019

(65) Prior Publication Data

US 2020/0046852 A1 Feb. 13, 2020

Related U.S. Application Data

(63) Continuation of application No. 15/607,083, filed on May 26, 2017, now Pat. No. 10,383,954, which is a continuation of application No. 14/767,977, filed as application No. PCT/IB2014/000704 on Feb. 4, 2014, now Pat. No. 9,682,154.

(60) Provisional application No. 61/907,286, filed on Nov. 21, 2013, provisional application No. 61/858,467, filed on Jul. 25, 2013, provisional application No. 61/800,716, filed on Mar. 15, 2013, provisional application No. 61/760,601, filed on Feb. 4, 2013.

(51) Int. Cl.

| *A61K 38/17* | (2006.01) |
|---|---|
| *A61K 38/19* | (2006.01) |
| *A61K 39/00* | (2006.01) |
| *A61K 48/00* | (2006.01) |
| *C07K 14/705* | (2006.01) |
| *C07K 16/22* | (2006.01) |
| *A61K 39/395* | (2006.01) |

(52) U.S. Cl.
CPC ...... *A61K 48/0058* (2013.01); *A61K 38/1793* (2013.01); *A61K 38/191* (2013.01); *A61K 39/3955* (2013.01); *C07K 14/70578* (2013.01); *C07K 16/22* (2013.01); *C12N 2710/10343* (2013.01)

(58) Field of Classification Search
CPC ........ A61K 38/17; A61K 38/19; A61K 39/00; A61K 39/395; A61K 48/00; C07K 14/705; C07K 16/22

See application file for complete search history.

(56) References Cited

U.S. PATENT DOCUMENTS

| 5,952,199 | A | 9/1999 | Davis-Smyth et al. |
|---|---|---|---|
| 7,067,649 | B2 | 6/2006 | Harats |
| 7,169,901 | B2 | 1/2007 | Baca et al. |
| 7,297,334 | B2 | 11/2007 | Baca et al. |
| 7,423,125 | B2 | 9/2008 | Alitalo et al. |
| 7,498,414 | B2 | 3/2009 | Zhu |
| 7,579,327 | B2 | 8/2009 | Harats et al. |
| 7,585,666 | B2 | 9/2009 | Harats et al. |
| 7,972,596 | B2 | 7/2011 | Wu et al. |
| 7,989,427 | B2 | 8/2011 | Harats et al. |
| 8,034,905 | B2 | 10/2011 | Kavile et al. |
| 8,039,261 | B2 | 10/2011 | Harats et al. |
| 8,071,740 | B2 | 12/2011 | Harats et al. |
| 8,206,743 | B2 | 6/2012 | Harats et al. |
| 8,415,318 | B2 | 4/2013 | Harats et al. |
| 8,835,398 | B2 | 9/2014 | Harats et al. |
| 8,846,401 | B2 | 9/2014 | Harats et al. |
| 8,859,745 | B2 | 10/2014 | Harats et al. |
| 8,859,747 | B2 | 10/2014 | Harats et al. |
| 8,916,378 | B2 | 12/2014 | Harats et al. |
| 9,200,056 | B2 | 12/2015 | Breitbart et al. |
| 9,682,154 | B2* | 6/2017 | Leubitz .................. C07K 16/22 |
| 10,383,954 | B2* | 8/2019 | Leubitz ............ C07K 14/70578 |
| 2002/0110543 | A1 | 8/2002 | Chiocca et al. |
| 2003/0138405 | A1 | 7/2003 | Fueyo et al. |
| 2007/0286845 | A1 | 12/2007 | Harats et al. |
| 2009/0317456 | A1* | 12/2009 | Karrasch .............. A61K 31/437 424/450 |
| 2010/0282634 | A1 | 11/2010 | Harats et al. |
| 2010/0298226 | A1 | 11/2010 | Breitbart et al. |
| 2011/0129511 | A1* | 6/2011 | Harats ..................... A61P 35/04 424/402 |
| 2011/0201677 | A1 | 8/2011 | Harats et al. |
| 2011/0207985 | A1 | 8/2011 | Harats et al. |

(Continued)

FOREIGN PATENT DOCUMENTS

| WO | WO-0044777 A1 | 8/2000 |
|---|---|---|
| WO | WO-03033514 A1 | 4/2003 |

(Continued)

OTHER PUBLICATIONS

Libertini et al, Clin. Cancer Res. 14(20): 6505-6514, 2008.*
Ferrara et al, Biochem. Biophys. Res. Comm. 333:328-335, 2005.*
Gerber and Ferrara, Cancer Res. 65(3):671-680, 2005.*
Boldin, M.P., et al., "A novel protein that interacts with the death domain of Fas/APO1 contains a sequence motif related to the death domain," Journal of Biological Chemistry 270(14):7795-7798, American Society for Biochemistry and Molecular Biology, United States (1995).

(Continued)

*Primary Examiner* — Kevin K Hill
(74) *Attorney, Agent, or Firm* — Sterne, Kessler, Goldstein & Fox P.L.L.C.

(57) ABSTRACT

The invention provides methods of inducing or improving responsiveness to a VEGF antagonist to a subject or a subject population comprising administering an adenovirus comprising a nucleic acid construct comprising a FAS-chimera gene operably linked to an endothelial cell-specific promoter and administering the VEGF antagonist.

16 Claims, 3 Drawing Sheets

Specification includes a Sequence Listing.

(56) References Cited

U.S. PATENT DOCUMENTS

| | | |
|---|---|---|
| 2011/0319479 A1 | 12/2011 | Breitbart et al. |
| 2013/0011367 A1 | 1/2013 | Harats et al. |
| 2013/0052165 A1 | 2/2013 | Bangio et al. |
| 2013/0209450 A1 | 8/2013 | Cohen et al. |
| 2013/0280216 A1 | 10/2013 | Cohen et al. |
| 2013/0280217 A1 | 10/2013 | Cohen et al. |
| 2013/0295053 A1 | 11/2013 | Bangio et al. |
| 2013/0303595 A1 | 11/2013 | Cohen et al. |
| 2014/0010785 A1 | 1/2014 | Cohen et al. |
| 2015/0111957 A1 | 4/2015 | Breitbart et al. |
| 2019/0054130 A1* | 2/2019 | Breitbart ............... A61K 45/06 |

FOREIGN PATENT DOCUMENTS

| | | | |
|---|---|---|---|
| WO | WO-03093409 | A2 | 11/2003 |
| WO | WO-2006051545 | A2 | 5/2006 |
| WO | WO-2007096882 | A2 | 8/2007 |
| WO | WO-2008015675 | A2 | 2/2008 |
| WO | WO 11/083464 | * | 7/2011 |
| WO | WO-2011083464 | A2 | 7/2011 |
| WO | WO-2011083466 | A1 | 7/2011 |
| WO | WO-2011086509 | A1 | 7/2011 |
| WO | WO-2012052878 | A1 | 4/2012 |
| WO | WO-2013082511 | A9 | 9/2013 |
| WO | WO-2014060848 | A2 | 4/2014 |

OTHER PUBLICATIONS

Boldin, M.P., et al., "Self-association of the "Death Domains" of the p55 Tumor Necrosis Factor (TNF) Receptor and Fas/APO1 Prompts Signaling for TNF and Fas/APO1 Effects," Journal of Biological Chemistry 270(1):387-391, American Society for Biochemistry and Molecular Biology, United States (1995).

Chen, Y.H., et al., "Upstream Stimulatory Factors Regulate Aortic Preferentially Expressed Gene-1 Expression in Vascular Smooth Muscle Cells," Journal of Biological Chemistry 276(50):47658-47663, American Society for Biochemistry and Molecular Biology, United States (2001).

Collins, C.J., et al., "Molecular Cloning of the Human Gene for Von Willebrand Factor and Identification of the Transcription Initiation Site," Proceedings of the National Academy of Sciences USA 84(13):4393-4397, National Academy of Sciences, United States (1987).

Collins, T.J., et al., "Structure and Chromosomal Location of the Gene for Endothelial-leukocyte Adhesion Molecule 1," Journal of Biological Chemistry 266(4):2466-2473, American Society for Biochemistry and Molecular Biology, United States (1991).

Dennis, M.S., et al., "Albumin Binding as a General Strategy for Improving the Pharmacokinetics of Proteins," The Journal of Biological Chemistry 277(38):35035-35043, American Society for Biochemistry and Molecular Biology, United States (Sep. 2002).

Friedman, H.S., et al., "Bevacizumab Alone and in Combination with Irinotecan in Recurrent Glioblastoma," Journal of Clinical Oncology 27(28):4733-4740, American Society of Clinical Oncology, United States (2009).

Harats, D., et al., "Targeting Gene Expression to the Vascular Wall in Transgenic Mice Using the Murine Preproendothelin-1 Promoter," Journal of Clinical Investigation 95(3):1335-1344, American Society for Clinical Investigation, United States (1995).

Horley, K.J., et al., "Molecular Cloning of Murine Intercellular Adhesion Molecule (ICAM-1)," EMBO Journal 8(10):2889-2896, Wiley Blackwell, England (1989).

Iademarco, M.F., et al., "Characterization of the Promoterfor Vascular Cell Adhesion Molecule-1 (VCAM-1)," Journal of Biological Chemistry 267(23):16323-16329, American Society for Biochemistry and Molecular Biology, United States (1992).

International Search Report for International Application No. PCT/IB2014/000704, ISA/US, Alexandria, Virginia, United States, dated Sep. 26, 2014, 4 pages.

Layne, M.D., et al., "Characterization of the Mouse Aortic Carboxypeptidase-Like Protein Promoter Reveals Activity in Differentiated and Dedifferentiated Vascular Smooth Muscle Cells," Circulation Research 90(6):728-736, Lippincott Williams & Wilkins, United States (2002).

Morishita, K., et al., "A Novel Promoter for Vascular Endothelial Growth Factor Receptor (flt-1) that Confers Endothelial-Specific Gene Expression," Journal of Biological Chemistry 270(46):27948-27953, American Society for Biochemistry and Molecular Biology,United States (1995).

Newman, P.J., et al., "PECAM-1 (CD31) Cloning and Relation to Adhesion Molecules of the Immunoglobulin Gene Superfamily," Science 247(4947):1219-1222, Association for the Advancement of Science, United States (1990).

Piantadosi, S., "Sample Size and Power," in Clinical Trials, A Methodologic Perspective, 2nd edition, pp. 251-308, John Wiley & Sons, Inc., United States (2005).

Rapisarda, A., et al., "Increased Antitumor Activity of Bevacizumab in Combination with Hypoxia Inducible Factor-1 Inhibition," Molecular Cancer Therapeutics 8(7):1867-1877, American Association for Cancer Research, United States (2009).

Rattan, S.I., et al., "Protein Synthesis, Posttranslational Modifications, and Aging," Annals of the New York Academy of Sciences 663:48-62, John Wiley & Sons, Inc., United States (1992).

Rius, C., et al., "Cloning of the Promoter Region of Human Endoglin, the Target Gene for Hereditary Hemorrhagic Telangiectasia Type 1," Blood 92(12):4677-4690, American Society of Hematology, United States (1998).

Ronicke, V., et al., "Characterization of the Endothelium-Specific Murine Vascular Endothelial Growth Factor Receptor-2 (Flk-1) Promoter," Circulation Research 79(2):277-285, Lippincott Williams & Wilkins, United States (1996).

Sato, T.N., et al., "Tie-1 and Tie-2 Define Another Class of Putative Receptor Tyrosine Kinase Genes Expressed in Early Embryonic Vascular System," Proceedings of the National Academy of Sciences USA 90(20):9355-9358, National Academy of Sciences, United States (1993).

Seifter, S. and Englard, S., "Analysis for Protein Modifications and Nonprotein Cofactors," Methods in Enzymology 182:626-646, Academic Press, United States (1990).

Sukhatme, V.P., et al., "A Novel Early Growth Response Gene Rapidly Induced by Fibroblast, Epithelial Cell and Lymphocyte Mitogens," Oncogene Research 1(4):343-355, Nature Publishing Group, England (1987).

UniProtKB Database, "Submitted name: Tumor necrosis factor receptor 1", Accession No. D1MH71, Entry Date Apr. 16, 2014.

UniProtKB Database, "Recommended name: Tumor necrosis factor receptor superfamily member 1A", Accession No. O19131, Entry Date Jun. 11, 2014.

UniProtKB Database, "Recommended name: Tumor necrosis factor receptor superfamily member 1 A", Accession No. P19438-1, Entry Date Jul. 9, 2014.

UniProtKB Database, "Recommended name: Tumor necrosis factor receptor superfamily member 1A", Accession No. P19438-2, Entry Date Jul. 9, 2014.

UniProtKB Database, "Recommended name: Tumor necrosis factor receptor superfamily member 1A", Accession No. P19438-3, Entry Date Jul. 9, 2014.

UniProtKB Database, "Recommended name: Tumor necrosis factor receptor superfamily member 1A", Accession No. P22934, Entry Date Jun. 11, 2014.

UniProtKB Database, "Recommended name: Tumor necrosis factor receptor superfamily member 1 A", Accession No. P25118, Entry Date Jul. 9, 2014.

UniProtKB Database, "Recommended name: Tumor necrosis factor receptor superfamily member 6", Accession No. P25445, Entry Date Jul. 9, 2014.

UniProtKB Database, "Recommended name: Tumor necrosis factor receptor superfamily member 6", Accession No. P25446, Entry Date Jul. 9, 2014.

UniProtKB Database, "Recommended name: Tumor necrosis factor receptor superfamily member 1A", Accession No. P50555, Entry Date Apr. 16, 2014.

(56) References Cited

OTHER PUBLICATIONS

UniProtKB Database, "Recommended name: Tumor necrosis factor receptor superfamily member 6", Accession No. P51867, Entry Date May 14, 2014.

UniProtKB Database, "Recommended name: Tumor necrosis factor receptor superfamily member 6", Accession No. Q63199, Entry Date Jun. 11, 2014.

UniProtKB Database, "Recommended name: Tumor necrosis factor receptor superfamily member 6", Accession No. Q9BDN4, Entry Date Feb. 19, 2014.

UniProtKB Database, "Recommended name: Tumor necrosis factor receptor superfamily member 6", Accession No. Q9BDP2, Entry Date Feb. 19, 2014.

Wen, P.Y., et al., "Updated Response Assessment Criteria for High-grade Gliomas: Response Assessment in Neuro-oncology Working Group," Journal of Clinical Oncology 28(11):1963-1972, American Society of Clinical Oncology, United States (2010).

Written Opinion for International Application No. PCT/IB2014/000704, ISA/US, Alexandria, Virginia, United States, dated Sep. 26, 2014, 6 pages.

Wold, F., "Posttranslational Protein Modifications: Perspectives and Perspectives," in Posttranslational Covalent Modification of Proteins, Johnson, B.C., ed., pp. 1-21, Academic Press, New York, USA (1983).

Triozzi, P.L. and Borden, E.C., "VB-111 for Cancer," Expert Opinion on Biological Therapy 11 (12):1669-1676, Taylor & Francis, England (2011).

Breitbart, E., et al., "VB-111 a Novel Anti-Angiogenic Vector and a Promising Treatment for Metastatic Cancer in Combination with Other Anticancer Drugs," Cancer Research 71(8) Supplement, Abstract 3283 (Apr. 2011), American Association for Cancer Research, United States.

Ferrara, N., et al., "Bevacizumab (Avastin), a Humanized Anti-VEGF Monoclonal Antibody for Cancer Therapy," Biochemical and Biophysical Research Communications 333(2):328-335, Elsevier, United States (2005).

Gerber, H.P. and Ferrara, N., "Pharmacology and Pharmacodynamics of Bevacizumab as Monotherapy or in Combination With Cytotoxic Therapy in Preclinical Studies," Cancer Research 65(3):671-680, American Association for Cancer Research, United States (2005).

Libertini, S., et al., "Bevacizumab Increases Viral Distribution in Human Anaplastic Thyroid Carcinoma Xenografts and Enhances the Effects of E1a-defective Adenovirus DI922-947," Clinical Cancer Research 14(20):6505-6514, The Association, United States (2008).

\* cited by examiner

SEQUENCE LISTING

```
<160> NUMBER OF SEQ ID NOS: 33

<210> SEQ ID NO 1
<211> LENGTH: 1365
<212> TYPE: DNA
<213> ORGANISM: Homo sapiens
<220> FEATURE:
<221> NAME/KEY: misc_feature
<223> OTHER INFORMATION: TNFRSF1A

<400> SEQUENCE: 1
atgggcctct ccaccgtgcc tgacctgctg ctgccgctgg tgctcctgga gctgttggtg      60
ggaatatacc cctcaggggt tattggactg gtccctcacc tagggacag ggagaagaga      120 gatagtgtgt gtccccaagg aaatatatc caccctcaaa ataattcgat ttgctgtacc      180
aagtgccaca aggaaccta cttgtacaat gactgtccag gcccggggca ggatacggac      240
tgcagggagt gtgagagcgg ctccttcacc gcttcagaaa accacctcag acactgcctc      300
agctgctcca aatgccgaaa ggaaatgggt caggtggaga tctcttcttg cacagtggac      360
cgggacaccg tgtgtggctg caggaagaac cagtaccggc attattggag tgaaaacctt      420
ttccagtgct tcaattgcag cctctgcctc aatgggaccg tgcacctctc ctgccaggag      480
aaacagaaca ccgtgtgcac ctgccatgca ggtttctttc taagagaaaa cgagtgtgtc      540
tcctgtagta actgtaagaa aagcctggag tgcacgaagt tgtgcctacc ccagattgag      600
aatgttaagg gcactgagga ctcaggcacc acagtgctgt gcccctggt catttctcttt      660 ggtctttgcc ttttatccct cctcttcatt ggtttaatgt atcgctacca acggtggaag      720
tccaagctct actccattgt ttgtgggaaa tcgacacctg aaaaagaggg ggagcttgaa      780
ggaactacta ctaagcccct ggccccaaac ccaagcttca gtcccactcc aggcttcacc      840 cccacctgg gcttcagtcc cgtgcccagt tccaccttca cctccagctc cacctatacc      900
cccggtgact gtcccaactt tgcggctccc cgcagagagg tggcaccacc ctatcagggg      960
gctgacccca tccttgcgac agccctcgcc tccgacccca tcccaaccc ccttcagaag    1020 tgggaggaca gcgcccacaa gccacagagc ctagacactg atgacccgc gacgctgtac    1080 gccgtggtgg agaacgtgcc cccgttgcgc tggaaggaat tcgtgcggcg cctagggctg    1140
agcgaccacg agatcgatcg gctggagctg cagaacgggc gctgcctgcg cgaggcgcaa    1200
tacagcatgc tggcgacctg gaggcggcgc acgccgcggc gcgaggccac gctggagctg    1260
ctgggacgcg tgctccgcga catggaccctg ctgggctgcc tggaggacat cgaggaggcg    1320
ctttgcggcc ccgccgccct cccgccgcg cccagtcttc tcaga                    1365

<210> SEQ ID NO 2
<211> LENGTH: 455
<212> TYPE: PRT
<213> ORGANISM: Homo sapiens
<220> FEATURE:
<221> NAME/KEY: MISC_FEATURE
```

<223> OTHER INFORMATION: Wild Type TNF Receptor 1

<400> SEQUENCE: 2

```
Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Lys
        35                  40                  45

Tyr Ile His Pro Gln Asn Asn Ser Ile Cys Cys Thr Lys Cys His Lys
    50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Ser Glu Asn His Leu
            85                  90                  95

Arg His Cys Leu Ser Cys Ser Lys Cys Arg Lys Glu Met Gly Gln Val
        100                 105                 110

Glu Ile Ser Ser Cys Thr Val Asp Arg Asp Thr Val Cys Gly Cys Arg
    115                 120                 125

Lys Asn Gln Tyr Arg His Tyr Trp Ser Glu Asn Leu Phe Gln Cys Phe
130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
370                 375                 380

Ile Asp Arg Leu Glu Leu Gln Asn Gly Arg Cys Leu Arg Glu Ala Gln
385                 390                 395                 400
```

```
Tyr Ser Met Leu Ala Thr Trp Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
        435                 440                 445

Pro Ala Pro Ser Leu Leu Arg
    450                 455

<210> SEQ ID NO 3
<211> LENGTH: 591
<212> TYPE: DNA
<213> ORGANISM: Homo sapiens
<220> FEATURE:
<221> NAME/KEY: misc_feature
<223> OTHER INFORMATION: Ligand Binding Domain of TNFR1

<400> SEQUENCE: 3
atgggcctct ccaccgtgcc tgacctgctg ctgccgctgg tgctcctgga gctgttggtg      60
ggaatatacc cctcaggggt tattggactg gtccctcacc taggggacag ggagaagaga     120
gatagtgtgt gtccccaagg aaaatatatc caccctcaaa ataattcgat ttgctgtacc     180
aagtgccaca aaggaaccta cttgtacaat gactgtccag gcccggggca ggatacggac     240
tgcagggagt gtgagagcgg ctccttcacc gcttcagaaa accacctcag acactgcctc     300
agctgctcca atgccgaaa ggaaatgggt caggtggaga tctcttcttg cacagtggac     360
cgggacaccg tgtgtggctg caggaagaac cagtaccggc attattggag tgaaaacctt     420
ttccagtgct tcaattgcag cctctgcctc aatgggaccg tgcacctctc ctgccaggag     480
aaacagaaca ccgtgtgcac ctgccatgca ggtttctttc taagagaaaa cgagtgtgtc     540
tcctgtagta actgtaagaa aagcctggag tgcacgaagt tgtgcctacc a              591

<210> SEQ ID NO 4
<211> LENGTH: 197
<212> TYPE: PRT
<213> ORGANISM: Homo sapiens
<220> FEATURE:
<221> NAME/KEY: MISC_FEATURE
<223> OTHER INFORMATION: Ligand Binding Domain of TNFR1

<400> SEQUENCE: 4

Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Lys
        35                  40                  45

Tyr Ile His Pro Gln Asn Asn Ser Ile Cys Cys Thr Lys Cys His Lys
    50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Ser Glu Asn His Leu
                85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
```

```
                130             135             140
Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro
        195

<210> SEQ ID NO 5
<211> LENGTH: 1008
<212> TYPE: DNA
<213> ORGANISM: Homo sapiens
<220> FEATURE:
<221> NAME/KEY: misc_feature
<223> OTHER INFORMATION: full-length FAS

<400> SEQUENCE: 5
atgctgggca tctggaccct cctacctctg gttcttacgt ctgttgctag attatcgtcc      60
aaaagtgtta atgcccaagt gactgacatc aactccaagg gattggaatt gaggaagact    120
gttactacag ttgagactca gaacttggaa ggcctgcatc atgatggcca attctgccat    180
aagccctgtc ctccaggtga aggaaagct agggactgca cagtcaatgg ggatgaacca    240
gactgcgtgc cctgccaaga agggaaggag tacacagaca agcccatttt tcttccaaa    300 tgcagaagat gtagattgtg tgatgaagga catggcttag aagtgaaat aaactgcacc    360 cggacccaga taccaagtg cagatgtaaa ccaaactttt tttgtaactc tactgtatgt    420
gaacactgtg acccttgcac caaatgtgaa catggaatca tcaaggaatg cacactcacc    480
agcaacacca gtgcaaaga ggaaggatcc agatctaact gggggtggct ttgtcttctt    540
cttttgccaa ttccactaat tgtttgggtg aagagaaagg aagtacagaa acatgcaga    600 aagcacagaa aggaaaacca aggttctcat gaatctccaa ctttaaatcc tgaaacagtg    660
gcaataaatt tatctgatgt tgacttgagt aaatatatca ccactattgc tggagtcatg    720
acactaagtc aagttaaagg ctttgttcga agaatggtg tcaatgaagc caaaatagat    780
gagatcaaga tgacaatgt ccaagacaca gcagaacaga agttcaact gcttcgtaat    840 tggcatcaac ttcatggaaa gaagaagcg tatgacacat tgattaaaga tctcaaaaaa    900
gccaatcttt gtactcttgc agagaaaatt cagactatca tcctcaagga cattactagt    960
gactcagaaa attcaaactt cagaaatgaa atccaaagct tggtctag                 1008

<210> SEQ ID NO 6
<211> LENGTH: 335
<212> TYPE: PRT
<213> ORGANISM: Homo sapiens
<220> FEATURE:
<221> NAME/KEY: MISC_FEATURE
<223> OTHER INFORMATION: full-length FAS

<400> SEQUENCE: 6

Met Leu Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
            20                  25                  30

Lys Gly Leu Glu Leu Arg Lys Thr Val Thr Thr Val Glu Thr Gln Asn
        35                  40                  45
```

Leu Glu Gly Leu His His Asp Gly Gln Phe Cys His Lys Pro Cys Pro
    50                  55                  60

Pro Gly Glu Arg Lys Ala Arg Asp Cys Thr Val Asn Gly Asp Glu Pro
65                  70                  75                  80

Asp Cys Val Pro Cys Gln Glu Gly Lys Glu Tyr Thr Asp Lys Ala His
                85                  90                  95

Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
            115                 120                 125

Cys Lys Pro Asn Phe Phe Cys Asn Ser Thr Val Cys Glu His Cys Asp
    130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Arg Ser Asn Leu Gly Trp
                165                 170                 175

Leu Cys Leu Leu Leu Leu Pro Ile Pro Leu Ile Val Trp Val Lys Arg
            180                 185                 190

Lys Glu Val Gln Lys Thr Cys Arg Lys His Arg Lys Glu Asn Gln Gly
            195                 200                 205

Ser His Glu Ser Pro Thr Leu Asn Pro Glu Thr Val Ala Ile Asn Leu
    210                 215                 220

Ser Asp Val Asp Leu Ser Lys Tyr Ile Thr Thr Ile Ala Gly Val Met
225                 230                 235                 240

Thr Leu Ser Gln Val Lys Gly Phe Val Arg Lys Asn Gly Val Asn Glu
                245                 250                 255

Ala Lys Ile Asp Glu Ile Lys Asn Asp Asn Val Gln Asp Thr Ala Glu
            260                 265                 270

Gln Lys Val Gln Leu Leu Arg Asn Trp His Gln Leu His Gly Lys Lys
            275                 280                 285

Glu Ala Tyr Asp Thr Leu Ile Lys Asp Leu Lys Lys Ala Asn Leu Cys
    290                 295                 300

Thr Leu Ala Glu Lys Ile Gln Thr Ile Ile Leu Lys Asp Ile Thr Ser
305                 310                 315                 320

Asp Ser Glu Asn Ser Asn Phe Arg Asn Glu Ile Gln Ser Leu Val
                325                 330                 335

<210> SEQ ID NO 7
<211> LENGTH: 505
<212> TYPE: DNA
<213> ORGANISM: Homo sapiens
<220> FEATURE:
<221> NAME/KEY: misc_feature
<223> OTHER INFORMATION: Effector Domain of FAS

<400> SEQUENCE: 7
aggatccaga tctaacttgg ggtggctttg tcttcttctt tgccaattc cactaattgt      60 ttgggtgaag agaaaggaag tacagaaaac atgcagaaag cacagaaagg aaaaccaagg    120
ttctcatgaa tctccaacct taaatcctga aacagtggca ataaatttat ctgatgttga    180
cttgagtaaa tatatcacca ctattgctgg agtcatgaca ctaagtcaag ttaaaggctt    240
tgttcgaaag aatggtgtca atgaagccaa aatagatgag atcaagaatg acaatgtcca    300
agacacagca gaacagaaag ttcaactgct tcgtaattgg catcaacttc atggaaagaa    360
agaagcgtat gacacattga ttaaagatct caaaaaagcc aatctttgta ctcttgcaga    420

```
gaaaattcag actatcatcc tcaaggacat tactagtgac tcagaaaatt caaacttcag    480
aaatgaaatc caaagcttgg tctag                                         505
```

<210> SEQ ID NO 8
<211> LENGTH: 167
<212> TYPE: PRT
<213> ORGANISM: Homo sapiens
<220> FEATURE:
<221> NAME/KEY: MISC_FEATURE
<223> OTHER INFORMATION: Effector Domain of FAS

<400> SEQUENCE: 8

```
Gly Ser Arg Ser Asn Leu Gly Trp Leu Cys Leu Leu Leu Leu Pro Ile
 1               5                  10                  15

Pro Leu Ile Val Trp Val Lys Arg Lys Glu Val Gln Lys Thr Cys Arg
            20                  25                  30

Lys His Arg Lys Glu Asn Gln Gly Ser His Glu Ser Pro Thr Leu Asn
        35                  40                  45

Pro Glu Thr Val Ala Ile Asn Leu Ser Asp Val Asp Leu Ser Lys Tyr
    50                  55                  60

Ile Thr Thr Ile Ala Gly Val Met Thr Leu Ser Gln Val Lys Gly Phe
65                  70                  75                  80

Val Arg Lys Asn Gly Val Asn Glu Ala Lys Ile Asp Glu Ile Lys Asn
                85                  90                  95

Asp Asn Val Gln Asp Thr Ala Glu Gln Lys Val Gln Leu Leu Arg Asn
            100                 105                 110

Trp His Gln Leu His Gly Lys Lys Glu Ala Tyr Asp Thr Leu Ile Lys
        115                 120                 125

Asp Leu Lys Lys Ala Asn Leu Cys Thr Leu Ala Glu Lys Ile Gln Thr
    130                 135                 140

Ile Ile Leu Lys Asp Ile Thr Ser Asp Ser Glu Asn Ser Asn Phe Arg
145                 150                 155                 160

Asn Glu Ile Gln Ser Leu Val
                165
```

<210> SEQ ID NO 9
<211> LENGTH: 1101
<212> TYPE: DNA
<213> ORGANISM: Homo sapiens
<220> FEATURE:
<221> NAME/KEY: misc_feature
<223> OTHER INFORMATION: FAS-chimera

<400> SEQUENCE: 9

```
atgggcctct ccaccgtgcc tgacctgctg ctgccgctgg tgctcctgga gctgttggtg    60
ggaatatacc cctcagggt tattggactg gtccctcacc tagggacag ggagaagaga    120 gatagtgtgt gtccccaagg aaaatatatc caccctcaaa ataattcgat ttgctgtacc    180
aagtgccaca aggaaccta cttgtacaat gactgtccag gccgggggca ggatacggac    240
tgcagggagt gtgagagcgg ctccttcacc gcttcagaaa accacctcag acactgcctc    300
agctgctcca atgccgaaa ggaaatgggt caggtggaga tctcttcttg cacagtggac    360
cgggacaccg tgtgtggctg caggaagaac cagtaccggc attattggag tgaaaacctt    420
ttccagtgct tcaattgcag cctctgcctc aatgggaccg tgcacctctc ctgccaggag    480
aaacagaaca ccgtgtgcac ctgccatgca ggtttctttc taagagaaaa cgagtgtgtc    540
tcctgtagta actgtaagaa aagcctggag tgcacgaagt tgtgcctacc aagcttagga    600
```

-continued

```
tccagatcta acttggggtg gctttgtctt cttcttttgc caattccact aattgtttgg    660
gtgaagagaa aggaagtaca gaaaacatgc agaaagcaca gaaaggaaaa ccaaggttct    720
catgaatctc caaccttaaa tcctgaaaca gtggcaataa atttatctga tgttgacttg    780
agtaaatata tcaccactat tgctggagtc atgacactaa gtcaagttaa aggctttgtt    840
cgaaagaatg gtgtcaatga agccaaaata gatgagatca gaatgacaa tgtccaagac     900 acagcagaac agaaagttca actgcttcgt aattggcatc aacttcatgg aaagaaagaa    960
gcgtatgaca cattgattaa agatctcaaa aaagccaatc tttgtactct tgcagagaaa   1020
attcagacta tcatcctcaa ggacattact agtgactcag aaaattcaaa cttcagaaat   1080
gaaatccaaa gcttggtcta g                                              1101
```

<210> SEQ ID NO 10
<211> LENGTH: 366
<212> TYPE: PRT
<213> ORGANISM: Homo sapiens
<220> FEATURE:
<221> NAME/KEY: MISC_FEATURE
<223> OTHER INFORMATION: FAS-chimera

<400> SEQUENCE: 10

```
Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Lys
        35                  40                  45

Tyr Ile His Pro Gln Asn Asn Ser Ile Cys Cys Thr Lys Cys His Lys
    50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Ser Glu Asn His Leu
                85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Ser Leu Gly Ser Arg Ser Asn Leu Gly Trp Leu
        195                 200                 205

Cys Leu Leu Leu Leu Pro Ile Pro Leu Ile Val Trp Val Lys Arg Lys
    210                 215                 220

Glu Val Gln Lys Thr Cys Arg Lys His Arg Lys Glu Asn Gln Gly Ser
225                 230                 235                 240

His Glu Ser Pro Thr Leu Asn Pro Glu Thr Val Ala Ile Asn Leu Ser
                245                 250                 255

Asp Val Asp Leu Ser Lys Tyr Ile Thr Thr Ile Ala Gly Val Met Thr
            260                 265                 270
```

```
Leu Ser Gln Val Lys Gly Phe Val Arg Lys Asn Gly Val Asn Glu Ala
    275                 280                 285
Lys Ile Asp Glu Ile Lys Asn Asp Asn Val Gln Asp Thr Ala Glu Gln
    290                 295                 300
Lys Val Gln Leu Leu Arg Asn Trp His Gln Leu His Gly Lys Lys Glu
305                 310                 315                 320
Ala Tyr Asp Thr Leu Ile Lys Asp Leu Lys Lys Ala Asn Leu Cys Thr
                325                 330                 335
Leu Ala Glu Lys Ile Gln Thr Ile Ile Leu Lys Asp Ile Thr Ser Asp
                340                 345                 350
Ser Glu Asn Ser Asn Phe Arg Asn Glu Ile Gln Ser Leu Val
                355                 360                 365

<210> SEQ ID NO 11
<211> LENGTH: 47
<212> TYPE: DNA
<213> ORGANISM: Artificial Sequence
<220> FEATURE:
<223> OTHER INFORMATION: Endothelial Cell-Specific Enhancer Elements

<400> SEQUENCE: 11
ctggagggtg actttgcttc tggagccagt acttcatact tttcatt              47

<210> SEQ ID NO 12
<211> LENGTH: 47
<212> TYPE: DNA
<213> ORGANISM: Artificial Sequence
<220> FEATURE:
<223> OTHER INFORMATION: Endothelial Cell-Specific Enhancer

<400> SEQUENCE: 12
aatgaaaagt atgaagtact ggctccagaa gcaaagtcac cctccag              47

<210> SEQ ID NO 13
<211> LENGTH: 44
<212> TYPE: DNA
<213> ORGANISM: Artificial Sequence
<220> FEATURE:
<223> OTHER INFORMATION: Endothelial Cell-Specific Enhancer

<400> SEQUENCE: 13
gtacttcata cttttcattc caatggggtg actttgcttc tgga                 44

<210> SEQ ID NO 14
<211> LENGTH: 44
<212> TYPE: DNA
<213> ORGANISM: Artificial Sequence
<220> FEATURE:
<223> OTHER INFORMATION: Endothelial Cell-Specific Enhancer Element

<400> SEQUENCE: 14
tccagaagca aagtcacccc attggaatga aaagtatgaa gtac                 44

<210> SEQ ID NO 15
<211> LENGTH: 131
<212> TYPE: DNA
<213> ORGANISM: Artificial Sequence
<220> FEATURE:
<223> OTHER INFORMATION: Endothelial Cell-Specific 3X Enhancer Element

<400> SEQUENCE: 15
ctccagaagc aaagtcaccc cattggaatg aaaagtatga agtacaatga aaagtatgaa   60
```
gtactggctc cagaagcaaa gtcaccctcc agaagcaaag tcaccccatt ggaatgaaaa    120
gtatgaagta c                                                        131

<210> SEQ ID NO 16
<211> LENGTH: 131
<212> TYPE: DNA
<213> ORGANISM: Artificial Sequence
<220> FEATURE:
<223> OTHER INFORMATION: Endothelial Cell-Specific 3X Enhancer Element

<400> SEQUENCE: 16
gtacttcata cttttcattc caatggggtg actttgcttc tggagggtga ctttgcttct    60
ggagccagta cttcatactt ttcattgtac ttcatacttt tcattccaat ggggtgactt    120
tgcttctgga g                                                        131

<210> SEQ ID NO 17
<211> LENGTH: 850
<212> TYPE: DNA
<213> ORGANISM: Artificial Sequence
<220> FEATURE:
<223> OTHER INFORMATION: Endothelial Cell-Specific PPE-1 Promoter

<400> SEQUENCE: 17
gtacgtgtac ttctgatcgg cgatactagg gagataagga tgtgcctgac aaaaccacat    60
tgttgttgtt atcattatta tttagttttc cttccttgct aactcctgac ggaatctttc    120
tcacctcaaa tgcgaagtac tttagtttag aaaagacttg gtggaagggg tggtggtgga    180
aaagtagggt gatcttccaa actaatctgg ttccccgccc gccccagtag ctgggattca    240
agagcgaaga gtggggatcg tccccttgtt tgatcagaaa gacataaaag gaaaatcaag    300
tgaacaatga tcagccccac ctccacccca ccccccctgcg cgcgcacaat acaatctatt    360
taattgtact tcatactttt cattccaatg gggtgactttt gcttctggag aaactcttga    420
ttcttgaact ctggggctgg cagctagcaa aaggggaagc gggctgctgc tctctgcagg    480
ttctgcagcg gtctctgtct agtgggtgtt ttcttttttct tagccctgcc cctggattgt    540
cagacggcgg gcgtctgcct ctgaagttag ccgtgatttc ctctagagcc gggtcttatc    600
tctggctgca cgttgcctgt gggtgactaa tcacacaata acattgttta gggctggaat    660
gaagtcagag ctgtttaccc ccactctata ggggttcaat ataaaaaggc ggcggagaac    720
tgtccgagtc agaagcgttc ctgcaccggc gctgagagcc tgacccggtc tgctccgctg    780
tccttgcgcg ctgcctcccg gctgcccgcg acgctttcgc cccagtggaa gggccacttg    840
ctgcggccgc                                                          850

<210> SEQ ID NO 18
<211> LENGTH: 987
<212> TYPE: DNA
<213> ORGANISM: Artificial Sequence
<220> FEATURE:
<223> OTHER INFORMATION: Endothelial Cell-Specific PPE-1 3X Promoter

<400> SEQUENCE: 18
gtacgtgtac ttctgatcgg cgatactagg gagataagga tgtgcctgac aaaaccacat    60
tgttgttgtt atcattatta tttagttttc cttccttgct aactcctgac ggaatctttc    120
tcacctcaaa tgcgaagtac tttagtttag aaaagacttg gtggaagggg tggtggtgga    180
aaagtagggt gatcttccaa actaatctgg ttccccgccc gccccagtag ctgggattca    240
agagcgaaga gtggggatcg tccccttgtt tgatcagaaa gacataaaag gaaaatcaag    300

```
tgaacaatga tcagccccac ctccacccca cccccctgcg cgcgcacaat acaatctatt       360
taattgtact tcatactttt cattccaatg gggtgacttt gcttctggag aaactcttga       420
ttcttgaact ctggggctgg cagctagcct ccagaagcaa agtcacccca ttggaatgaa       480
aagtatgaag tacaatgaaa agtatgaagt actggctcca gaagcaaagt caccctccag       540
aagcaaagtc accccattgg aatgaaaagt atgaagtacg ctagcaaaag gggaagcggg       600
ctgctgctct ctgcaggttc tgcagcggtc tctgtctagt gggtgttttc ttttcttag       660 ccctgcccct ggattgtcag acggcgggcg tctgcctctg aagttagccg tgatttcctc       720
tagagccggg tcttatctct ggctgcacgt tgcctgtggg tgactaatca cacaataaca       780
ttgtttaggg ctggaatgaa gtcagagctg tttacccca ctctataggg gttcaatata       840
aaaaggcggc ggagaactgt ccgagtcaga agcgttcctg caccggcgct gagagcctga       900
cccggtctgc tccgctgtcc ttgcgcgctg cctcccggct gcccgcgacg ctttcgcccc       960
agtggaaggg ccacttgctg cggccgc                                           987

<210> SEQ ID NO 19
<211> LENGTH: 35207
<212> TYPE: DNA
<213> ORGANISM: Artificial Sequence
<220> FEATURE:
<223> OTHER INFORMATION: VB-111 entire construct

<400> SEQUENCE: 19
catcatcaat aatataccttt attttggatt gaagccaata tgataatgag ggggtggagt       60
ttgtgacgtg gcgcggggcg tgggaacggg gcgggtgacg tagtagtgtg gcggaagtgt      120
gatgttgcaa gtgtggcgga acacatgtaa gcgacggatg tggcaaaagt gacgttttg       180 gtgtgcgccg gtgtacacag gaagtgacaa ttttcgcgcg gttttaggcg gatgttgtag      240
taaatttggg cgtaaccgag taagatttgg ccattttcgc gggaaaactg aataagagga      300
agtgaaatct gaataatttt gtgttactca tagcgcgtaa tatttgtcta gggccgcggg      360
gactttgacc gtttacgtgg agactcgccc aggtgttttt ctcaggtgtt ttccgcgttc      420
cgggtcaaag ttggcgtttt attattatag tcagtacgta cgtgtacttc tgatcggcga      480
tactagggag ataaggatgt gcctgacaaa accacattgt tgttgttatc attattattt      540
agttttcctt ccttgctaac tcctgacgga atctttctca cctcaaatgc gaagtacttt      600
agtttagaaa agacttggtg aaggggtgg tggtggaaaa gtagggtgat cttccaaact      660
aatctggttc cccgcccgcc ccagtagctg ggattcaaga gcgaagagtg gggatcgtcc      720
ccttgtttga tcagaaagac ataaaaggaa aatcaagtga acaatgatca gccccacctc      780 cacccccaccc cctgcgcgc gcacaataca atctatttaa ttgtacttca tacttttcat      840
tccaatgggg tgactttgct tctggagaaa ctcttgattc ttgaactctg ggctggcag      900 ctagcctcca gaagcaaagt caccccattg aatgaaaag tatgaagtac aatgaaaagt      960
atgaagtact ggctccagaa gcaaagtcac cctccagaag caaagtcacc ccattggaat     1020
gaaaagtatg aagtacgcta gcaaaagggg aagcgggctg ctgctctctg caggttctgc     1080
agcggtctct gtctagtggg tgttttcttt tccttagccc tgcccctgga ttgtcagacg     1140
gcgggcgtct gcctctgaag ttagccgtga tttcctctag agccgggtct tatctctggc     1200
tgcacgttgc ctgtgggtga ctaatcacac aataacattg tttagggctg gaatgaagtc     1260
agagctgttt accccactc tatagggtt caatataaaa aggcggcgga gaactgtccg     1320
```

```
agtcagaagc gttcctgcac cggcgctgag agcctgaccc ggtctgctcc gctgtccttg    1380
cgcgctgcct cccggctgcc cgcgacgctt tcgccccagt ggaagggcca cttgctgcgg    1440
ccgctaattc tgcagatcgg gatccggcat gggcctctcc accgtgcctg acctgctgct    1500
gccgctggtg ctcctggagc tgttggtggg aatataccccc tcaggggtta ttggactggt    1560
ccctcaccta ggggacaggg agaagagaga tagtgtgtgt ccccaaggaa aatatatcca    1620
ccctcaaaat aattcgattt gctgtaccaa gtgccacaaa ggaacctact tgtacaatga    1680
ctgtccaggc ccggggcagg atacggactg cagggagtgt gagagcggct ccttcaccgc    1740
ttcagaaaac cacctcagac actgcctcag ctgctccaaa tgccgaaagg aaatgggtca    1800
ggtggagatc tcttcttgca cagtggaccg ggacaccgtg tgtggctgca ggaagaacca    1860
gtaccggcat tattggagtg aaaaccttt ccagtgcttc aattgcagcc tctgcctcaa    1920
tgggaccgtg cacctctcct gccaggagaa acagaacacc gtgtgcacct gccatgcagg    1980
tttctttcta agagaaaacg agtgtgtctc ctgtagtaac tgtaagaaaa gcctggagtg    2040
cacgaagttg tgcctaccaa gcttaggatc cagatctaac ttggggtggc tttgtcttct    2100
tcttttgcca attccactaa ttgtttgggt gaagagaaag gaagtacaga aaacatgcag    2160
aaagcacaga aaggaaaacc aaggttctca tgaatctcca accttaaatc ctgaaacagt    2220
ggcaataaat ttatctgatg ttgacttgag taaatatatc accactattg ctggagtcat    2280
gacactaagt caagttaaag gctttgttcg aaagaatggt gtcaatgaag ccaaaataga    2340
tgagatcaag aatgacaatg tccaagacac agcagaacag aaagttcaac tgcttcgtaa    2400
ttggcatcaa cttcatggaa agaaagaagc gtatgacaca ttgattaaag atctcaaaaa    2460
agccaatctt tgtactcttg cagagaaaat tcagactatc atcctcaagg acattactag    2520
tgactcagaa aattcaaact tcagaaatga aatccaaagc ttggtctagc tcgagcatgc    2580
atctaggcgg ccgcatggca gaaattcgcg aattcgctag cgttaacgga tcctctagac    2640
gagatccgaa cttgtttatt gcagcttata atggttacaa ataaagcaat agcatcacaa    2700
atttcacaaa taaagcattt ttttcactgc attctagttg tggtttgtcc aaactcatca    2760
atgtatctta tcatgtctag atctgtactg aaatgtgtgg gcgtggctta agggtgggaa    2820
agaatatata aggtgggggt cttatgtagt tttgtatctg ttttgcagca gccgccgccg    2880
ccatgagcac caactcgttt gatggaagca ttgtgagctc atatttgaca acgcgcatgc    2940
ccccatgggc cggggtgcgt cagaatgtga tgggctccag cattgatggt cgccccgtcc    3000
tgcccgcaaa ctctactacc ttgacctacg agaccgtgtc tggaacgccg ttggagactg    3060
cagcctccgc cgccgcttca gccgctgcag ccaccgcccg cgggattgtg actgactttg    3120
ctttcctgag cccgcttgca agcagtgcag cttcccgttc atccgcccgc gatgacaagt    3180
tgacggctct tttggcacaa ttggattctt tgacccggga acttaatgtc gtttctcagc    3240
agctgttgga tctgcgccag caggtttctg ccctgaaggc ttcctcccct cccaatgcgg    3300
tttaaaacat aaataaaaaa ccagactctg tttggatttg gatcaagcaa gtgtcttgct    3360
gtctttattt aggggttttg cgcgcgcggt aggcccggga ccagcggtct cggtcgttga    3420
gggtcctgtg tatttttttcc aggacgtggt aaaggtgact ctggatgttc agatacatgg    3480
gcataagccc gtctctgggg tggaggtagc accactgcag agcttcatgc tgcgggtgg    3540
tgttgtagat gatccagtcg tagcaggagc gctgggcgtg gtgcctaaaa atgtctttca    3600
gtagcaagct gattgccagg gcaggccct tggtgtaagt gttacaaag cggttaagct    3660
gggatgggtg catacgtggg gatatgagat gcatcttgga ctgtattttt aggttggcta    3720
```

```
tgttcccagc catatccctc cggggattca tgttgtgcag aaccaccagc acagtgtatc    3780
cggtgcactt gggaaatttg tcatgtagct tagaaggaaa tgcgtggaag aacttggaga    3840
cgcccttgtg acctccaaga ttttccatgc attcgtccat aatgatggca atgggcccac    3900
gggcggcggc ctgggcgaag atatttctgg gatcactaac gtcatagttg tgttccagga    3960
tgagatcgtc ataggccatt tttacaaagc gcgggcggag ggtgccagac tgcggtataa    4020
tggttccatc cggcccaggg gcgtagttac cctcacagat ttgcatttcc cacgctttga    4080
gttcagatgg ggggatcatg tctacctgcg gggcgatgaa gaaaacggtt tccggggtag    4140
gggagatcag ctgggaagaa agcaggttcc tgagcagctg cgacttaccg cagccggtgg    4200
gcccgtaaat cacacctatt accggctgca actggtagtt aagagagctg cagctgccgt    4260
catccctgag caggggggcc acttcgttaa gcatgtccct gactcgcatg ttttccctga    4320
ccaaatccgc cagaaggcgc tcgccgccca gcgatagcag ttcttgcaag gaagcaaagt    4380
ttttcaacgg tttgagaccg tccgccgtag gcatgctttt gagcgtttga ccaagcagtt    4440
ccaggcggtc ccacagctcg gtcacctgct ctacggcatc tcgatccagc atatctcctc    4500
gtttcgcggg ttggggcggc tttcgctgta cggcagtagt cggtgctcgt ccagacgggc    4560
cagggtcatg tctttccacg ggcgcagggt cctcgtcagc gtagtctggg tcacggtgaa    4620
ggggtgcgct ccgggctgcg cgctggccag ggtgcgcttg aggctggtcc tgctggtgct    4680
gaagcgctgc cggtcttcgc cctgcgcgtc ggccaggtag catttgacca tggtgtcata    4740
gtccagcccc tccgcggcgt ggcccttggc gcgcagcttg cccttggagg aggcgccgca    4800
cgaggggcag tgcagacttt tgagggcgta gagcttgggc gcgagaaata ccgattccgg    4860
ggagtaggca tccgcgccgc aggccccgca gacggtctcg cattccacga gccaggtgag    4920
ctctggccgt tcggggtcaa aaaccaggtt tcccccatgc ttttgatgc gtttcttacc    4980
tctggtttcc atgagccggt gtccacgctc ggtgacgaaa aggctgtccg tgtccccgta    5040
tacagacttg agaggcctgt cctcgagcgg tgttccgcgg tcctcctcgt atagaaactc    5100
ggaccactct gagacaaagg ctcgcgtcca ggccagcacg aaggaggcta agtgggaggg    5160
gtagcggtcg ttgtccacta gggggtccac tcgctccagg gtgtgaagac acatgtcgcc    5220
ctcttcggca tcaaggaagg tgattggttt gtaggtgtag ccacgtgac cgggtgttcc    5280
tgaaggggg ctataaaagg gggtgggggc gcgttcgtcc tcactctctt ccgcatcgct    5340
gtctgcgagg gccagctgtt ggggtgagta ctccctctga aaagcgggca tgacttctgc    5400
gctaagattg tcagtttcca aaaacgagga ggatttgata ttcacctggc ccgcggtgat    5460
gcctttgagg gtggccgcat ccatctggtc agaaaagaca atcttttgt tgtcaagctt    5520
ggtggcaaac gacccgtaga gggcgttgga cagcaacttg gcgatggagc gcagggtttg    5580
gttttttgtcg cgatcggcgc gctccttggc cgcgatgttt agctgcacgt attcgcgcgc    5640
aacgcaccgc cattcgggaa agacggtggt gcgctcgtcg ggcaccaggt gcacgcgcca    5700
accgcggttg tgcagggtga caaggtcaac gctggtggct acctctccgc gtaggcgctc    5760
gttggtccag cagaggcggc cgcccttgcg cgagcagaat ggcggtaggg ggtctagctg    5820
cgtctcgtcc gggggtctg cgtccacggt aaagaccccg ggcagcaggc gcgcgtcgaa    5880
gtagtctatc ttgcatcctt gcaagtctag cgcctgctgc catgcgcggg cggcaagcgc    5940
gcgctcgtat gggttgagtg ggggaccccca tggcatgggg tgggtgagcg cggaggcgta    6000
catgccgcaa atgtcgtaaa cgtagagggg ctctctgagt attccaagat atgtagggta    6060
```

```
gcatcttcca ccgccggatgc tggcgcgcac gtaatcgtat agttcgtgcg agggagcgag      6120
gaggtcggga ccgaggttgc tacgggcggg ctgctctgct cggaagacta tctgcctgaa      6180
gatggcatgt gagttggatg atatggttgg acgctggaag acgttgaagc tggcgtctgt      6240
gagacctacc gcgtcacgca cgaaggaggc gtaggagtcg cgcagcttgt tgaccagctc      6300
ggcggtgacc tgcacgtcta gggcgcagta gtccagggtt tccttgatga tgtcatactt      6360
atcctgtccc tttttttttcc acagctcgcg gttgaggaca aactcttcgc ggtctttcca      6420
gtactcttgg atcggaaacc cgtcggcctc cgaacggtaa gagcctagca gtagaactg       6480 gttgacggcc tggtaggcgc agcatcccctt ttctacgggt agcgcgtatg cctgcgcggc     6540
cttccggagc gaggtgtggg tgagcgcaaa ggtgtccctg accatgactt tgaggtactg      6600
gtatttgaag tcagtgtcgt cgcatccgcc ctgctcccag agcaaaaagt ccgtgcgctt      6660
tttggaacgc ggatttggca gggcgaaggt gacatcgttg aagagtatct ttcccgcgcg      6720
aggcataaag ttgcgtgtga tgcggaaggg tcccggcacc tcggaacggt tgttaattac      6780
ctgggcggcg agcacgatct cgtcaaagcc gttgatgttg tggcccacaa tgtaaagttc      6840
caagaagcgc gggatgccct tgatggaagg caattttttta agttcctcgt aggtgagctc     6900
ttcaggggag ctgagcccgt gctctgaaag ggcccagtct gcaagatgag ggttggaagc     6960
gacgaatgag ctccacaggt cacgggccat tagcatttgc aggtggtcgc gaaaggtcct      7020
aaactggcga cctatggcca ttttttctgg ggtgatgcag tagaaggtaa gcgggtcttg      7080
ttcccagcgg tcccatccaa ggttcgcggc taggtctcgc gcggcagtca ctagaggctc      7140
atctccgccg aacttcatga ccagcatgaa gggcacgagc tgcttcccaa aggcccccat      7200
ccaagtatag gtctctacat cgtaggtgac aaagagacgc tcggtgcgag gatgcgagcc      7260
gatcgggaag aactggatct cccgccacca attggaggag tggctattga tgtggtgaaa      7320
gtagaagtcc ctgcgacggg ccgaacactc gtgctggctt ttgtaaaaac gtgcgcagta      7380
ctggcagcgg tgcacgggct gtacatcctg cacgaggttg acctgacgac cgcgcacaag      7440
gaagcagagt gggaatttga gcccctcgcc tggcgggttt ggctggtggt cttctacttc      7500
ggctgcttgt ccttgaccgt ctggctgctc gaggggagtt acggtggatc ggaccaccac      7560
gccgcgcgag cccaaagtcc agatgtccgc gcgcggcggt cggagcttga tgacaacatc      7620
gcgcagatgg gagctgtcca tggtctggag ctcccgcggc gtcaggtcag gcgggagctc      7680
ctgcaggttt acctcgcata cgggtcag ggcgcgggct agatccaggt gatacctaat        7740
ttccaggggc tggttggtgg cggcgtcgat ggcttcaag aggccgcatc cccgcggcgc       7800
gactacggta ccgcgcggcg ggcggtgggc gcgggggtg tccttggatg atgcatctaa       7860
aagcggtgac gcgggcgagc ccccggaggt aggggggct ccggacccgc cgggagaggg      7920
ggcaggggca cgtcggcgcc gcgcgcgggc aggagctggt gctgcgcgcg taggttgctg      7980
gcgaacgcga cgacgcggcg gttgatctcc tgaatctggc gcctctgcgt gaagacgacg      8040
ggcccggtga gcttgaacct gaaagagagt tcgacagaat caatttcggt gtcgttgacg      8100
gcggcctggc gcaaaatctc ctgcacgtct cctgagttgt cttgataggc gatctcggcc      8160
atgaactgct cgatctcttc ctcctggaga tctccgcgtc cggctcgctc cacggtggcg      8220
gcgaggtcgt tggaaatgcg ggccatgagc tgcgagaagg cgttgaggcc tccctcgttc      8280
cagacgcggc tgtagaccac gccccttcg gcatcgcggg cgcgcatgac cacctgcgcg      8340
agattgagct ccacgtgccg ggcgaagacg gcgtagtttc gcaggcgctg aaagaggtag      8400
ttgagggtgg tggcggtgtg ttctgccacg aagaagtaca taacccagcg tcgcaacgtg      8460
```

```
gattcgttga tatcccccaa ggcctcaagg cgctccatgg cctcgtagaa gtccacggcg   8520
aagttgaaaa actgggagtt gcgcgccgac acgttaact  cctcctccag aagacggatg   8580
agctcggcga cagtgtcgcg cacctcgcgc tcaaaggcta caggggcctc ttcttcttct   8640
tcaatctcct cttccataag ggcctcccct tcttcttctt ctggcggcgg tgggggaggg   8700
gggacacggc ggcgacgacg gcgcaccggg aggcggtcga caaagcgctc gatcatctcc   8760
ccgcggcgac ggcgcatggt ctcggtgacg gcgcggccgt tctcgcgggg gcgcagttgg   8820
aagacgccgc ccgtcatgtc ccggttatgg gttggcgggg ggctgccatg cggcagggat   8880
acggcgctaa cgatgcatct caacaattgt tgtgtaggta ctccgccgcc gagggacctg   8940
agcgagtccg catcgaccgg atcggaaaac ctctcgagaa aggcgtctaa ccagtcacag   9000
tcgcaaggta ggctgagcac cgtggcgggc ggcagcgggc ggcggtcggg gttgtttctg   9060
gcggaggtgc tgctgatgat gtaattaaag taggcggtct tgagacggcg gatggtcgac   9120
agaagcacca tgtccttggg tccggcctgc tgaatgcgca ggcggtcggc catgccccag   9180
gcttcgtttt gacatcggcg caggtctttg tagtagtctt gcatgagcct ttctaccggc   9240
acttcttctt ctccttcctc ttgtcctgca tctcttgcat ctatcgctgc ggcggcggcg   9300
gagtttggcc gtaggtggcg ccctcttcct cccatgcgtg tgaccccgaa gcccctcatc   9360
ggctgaagca gggctaggtc ggcgacaacg cgctcggcta atatggcctg ctgcacctgc   9420
gtgagggtag actggaagtc atccatgtcc acaaagcggt ggtatgcgcc cgtgttgatg   9480
gtgtaagtgc agttggccat aacggaccag ttaacggtct ggtgacccgg ctgcgagagc   9540
tcggtgtacc tgagacgcga gtaagccctc gagtcaaata cgtagtcgtt gcaagtccgc   9600
accaggtact ggtatcccac caaaaagtgc ggcggcggct ggcggtagag gggccagcgt   9660
agggtggccg gggctccggg ggcgagatct tccaacataa ggcgatgata tccgtagatg   9720
tacctggaca tccaggtgat gccggcggcg gtggtggagg cgcgcggaaa gtcgcggacg   9780
cggttccaga tgttgcgcag cggcaaaaag tgctccatgg tcgggacgct ctggccggtc   9840
aggcgcgcgc aatcgttgac gctctagacc gtgcaaaagg agagcctgta agcgggcact   9900
cttccgtggt ctggtggata aattcgcaag ggtatcatgg cggacgaccg gggttcgagc   9960
cccgtatccg gccgtccgcc gtgatccatg cggttaccgc ccgcgtgtcg aacccaggtg  10020
tgcgacgtca dacaacggggg gagtgctcct tttggcttcc ttccaggcgc ggcggctgct  10080
gcgctagctt ttttggccac tggccgcgcg cagcgtaagc ggttaggctg gaaagcgaaa  10140
gcattaagtg gctcgctccc tgtagccgga gggttatttt ccaaggggttg agtcgcggga  10200 cccccggttc gagtctcgga ccggccggac tgcggcgaac gggggtttgc ctccccgtca  10260
tgcaagaccc cgcttgcaaa ttcctccgga aacaggacg agcccctttt ttgcttttcc  10320
cagatgcatc cggtgctgcg gcagatgcgc ccccctcctc agcagcggca agagcaagag  10380
cagcggcaga catgcagggc accctcccct cctcctaccg cgtcaggagg ggcgacatcc  10440
gcggttgacg cggcagcaga tggtgattac gaaccccgc  ggcgccgggc ccggcactac  10500
ctggacttgg aggagggcga gggcctggcc cggctaggag cgccctctcc tgagcggcac  10560
ccaagggtgc agctgaagcg tgatacgcgt gaggcgtacg tgccgcggca gaacctgttt  10620
cgcgaccgcg agggagagga gcccgaggag atgcgggatc gaaagttcca cgcagggcgc  10680
gagctgcggc atggcctgaa tcgcgagcgg ttgctgcgcg aggaggactt tgagcccgac  10740
gcgcgaaccg ggattagtcc cgcgcgcgca cacgtggcgg ccgccgacct ggtaaccgca  10800
```

```
tacgagcaga cggtgaacca ggagattaac tttcaaaaaa gctttaacaa ccacgtgcgt   10860
acgcttgtgg cgcgcgagga ggtggctata ggactgatgc atctgtggga ctttgtaagc   10920
gcgctggagc aaaacccaaa tagcaagccg ctcatggcgc agctgttcct tatagtgcag   10980
cacagcaggg acaacgaggc attcagggat gcgctgctaa acatagtaga gcccgagggc   11040
cgctggctgc tcgatttgat aaacatcctg cagagcatag tggtgcagga gcgcagcttg   11100
agcctggctg acaaggtggc cgccatcaac tattccatgc ttagcctggg caagttttac   11160
gcccgcaaga tataccatac cccttacgtt cccatagaca aggaggtaaa gatcgagggg   11220
ttctacatgc gcatggcgct gaaggtgctt accttgagcg acgacctggg cgtttatcgc   11280
aacgagcgca tccacaaggc cgtgagcgtg agccggcggc gcgagctcag cgaccgcgag   11340
ctgatgcaca gcctgcaaag ggccctggct ggcacgggca gcggcgatag agaggccgag   11400
tcctactttg acgcgggcgc tgacctgcgc tgggccccaa gccgacgcgc cctggaggca   11460
gctggggccg gacctgggct ggcggtggca cccgcgcgcg ctggcaacgt cggcggcgtg   11520
gaggaatatg acgaggacga tgagtacgag ccagaggacg gcgagtacta gcggtgatg   11580 tttctgatca gatgatgcaa gacgcaacgg accggcggt cgggcggcg ctgcagagcc   11640 agccgtccgg ccttaactcc acggacgact ggcgccaggt catggaccgc atcatgtcgc   11700
tgactgcgcg caatcctgac gcgttccggc agcagccgca ggccaaccgg ctctccgcaa   11760
ttctggaagc ggtggtcccg gcgcgcgcaa accccacgca cgagaaggtg ctggcgatcg   11820
taaacgcgct ggccgaaaac agggccatcc ggcccgacga ggccggcctg gtctacgacg   11880
cgctgcttca gcgcgtggct cgttacaaca gcggcaacgt gcagaccaac ctggaccggc   11940
tggtggggga tgtgcgcgag gccgtggcgc agcgtgagcg cgcgcagcag cagggcaacc   12000
tgggctccat ggttgcacta aacgccttcc tgagtacaca gcccgccaac gtgccgcggg   12060
gacaggagga ctacaccaac tttgtgagcg cactgcggct aatggtgact gagacaccgc   12120
aaagtgaggt gtaccagtct gggccagact atttttttcca gaccagtaga caaggcctgc   12180
agaccgtaaa cctgagccag gctttcaaaa acttgcaggg gctgtggggg gtgcgggctc   12240
ccacaggcga ccgcgcgacc gtgtctagct tgctgacgcc caactcgcgc ctgttgctgc   12300
tgctaatagc gcccttcacg gacagtggca gcgtgtcccg ggacacatac ctaggtcact   12360
tgctgacact gtaccgcgag gccataggtc aggcgcatgt ggacgagcat actttccagg   12420
agattacaag tgtcagccgc gcgctggggc aggaggacac gggcagcctg gaggcaaccc   12480
taaactacct gctgaccaac cggcggcaga agatcccctc gttgcacagt ttaaacagcg   12540
aggaggagcg cattttgcgc tacgtgcagc agagcgtgag ccttaacctg atgcgcgacg   12600
gggtaacgcc cagcgtggcg ctggacatga ccgcgcgcaa catggaaccg ggcatgtatg   12660
cctcaaaccg gccgtttatc aaccgcctaa tggactactt gcatcgcgcg ccgccgtga   12720 accccgagta tttcaccaat gccatcttga acccgcactg gctaccgccc ctggttttct   12780
acaccggggg attcgaggtg cccgagggta acgatggatt cctctgggac gacatagacg   12840
acagcgtgtt ttcccgcaa ccgcagaccc tgctagagtt gcaacagcgc gagcaggcag   12900
aggcggcgcg cgaaaggaa agcttccgca ggccaagcag cttgtccgat ctaggcgctg   12960
cggccccgcg gtcagatgct agtagcccat ttccaagctt gatagggtct cttaccagca   13020
ctcgcaccac ccgcccgcgc ctgctgggcg aggaggagta cctaaacaac tcgctgctgc   13080
agcccgcagc cgaaaaaaac ctgcctccgg catttcccaa caacgggata gagagcctag   13140
tggacaagat gagtagatgg aagacgtacg cgcaggagca cagggacgtg ccaggcccgc   13200
```

```
gcccgcccac ccgtcgtcaa aggcacgacc gtcagcgggg tctggtgtgg gaggacgatg   13260
actcggcaga cgacagcagc gtcctggatt tgggaggag tggcaacccg tttgcgcacc    13320
ttcgccccag gctggggaga atgttttaaa aaaaaaaaaa gcatgatgca aaataaaaaa   13380
ctcaccaagg ccatggcacc gagcgttggt tttcttgtat tccccttagt atgcggcgcg   13440
cggcgatgta tgaggaaggt cctcctccct cctacgagag tgtggtgagc gcggcgccag   13500
tggcggcggc gctgggttct cccttcgatg ctccccctgga cccgccgttt gtgcctccgc  13560
ggtacctgcg gcctaccggg gggagaaaca gcatccgtta ctctgagttg cacccctat    13620 tcgacaccac ccgtgtgtac ctggtggaca acaagtcaac ggatgtggca tccctgaact   13680
accagaacga ccacagcaac tttctgacca cggtcattca aaacaatgac tacagcccgg   13740
gggaggcaag cacacagacc atcaatcttg acgaccggtc gcactggggc ggcgacctga   13800
aaaccatcct gcataccaac atgccaaatg tgaacgagtt catgtttacc aataagttta   13860
aggcgcgggt gatggtgtcg cgcttgccta ctaaggacaa tcaggtggag ctgaaatacg   13920
agtgggtgga gttcacgctg cccgagggca actactccga gaccatgacc atagacctta   13980
tgaacaacgc gatcgtggag cactacttga aagtgggcag acagaacggg gttctggaaa   14040
gcgacatcgg ggtaaagttt gacacccgca acttcagact ggggtttgac cccgtcactg   14100
gtcttgtcat gcctggggta tatacaaacg aagccttcca tccagacatc attttgctgc   14160
caggatgcgg ggtggacttc acccacagcc gcctgagcaa cttgttgggc atccgcaagc   14220 ggcaacccctt ccaggagggc tttaggatca cctacgatga tctggaggt ggtaacattc    14280 ccgcactgtt ggatgtggac gcctaccagg cgagcttgaa agatgacacc gaacagggcg   14340
ggggtggcgc aggcggcagc aacagcagtg gcagcggcgc ggaagagaac tccaacgcgg   14400
cagccgcggc aatgcagccg gtggaggaca tgaacgatca tgccattcgc ggcgacacct   14460
ttgccacacg ggctgaggag aagcgcgctg aggccgaagc agcggccgaa gctgccgccc   14520
ccgctgcgca acccgaggtc gagaagcctc agaagaaacc ggtgatcaaa cccctgacag   14580
aggacagcaa gaaacgcagt tacaacctaa taagcaatga cagcaccttc acccagtacc   14640
gcagctggta ccttgcatac aactacggcg acctcagac cggaatccgc tcatggaccc   14700
tgctttgcac tcctgacgta acctgcggct cggagcaggt ctactggtcg ttgccagaca   14760
tgatgcaaga ccccgtgacc ttccgctcca cgcgccagat cagcaacttt ccggtggtgg   14820
gcgccgagct gttgcccgtg cactccaaga gcttctacaa cgaccaggcc gtctactccc   14880
aactcatccg ccagtttacc tctctgaccc acgtgttcaa tcgctttccc gagaaccaga   14940
ttttggcgcg cccgccagcc cccaccatca ccaccgtcag tgaaaacgtt cctgctctca   15000
cagatcacgg gacgctaccg ctgcgcaaca gcatcggagg agtccagcga gtgaccatta   15060
ctgacgccag acgccgcacc tgccctacg tttacaaggc cctgggcata gtctcgccgc    15120
gcgtcctatc gagccgcact ttttgagcaa gcatgtccat ccttatatcg cccagcaata   15180
acacaggctg gggcctgcgc ttcccaagca agatgtttgg cggggccaag aagcgctccg   15240
accaacaccc agtgcgcgtg cgcgggcact accgcgcgcc ctgggcgcg cacaaacgcg     15300 gccgcactgg gcgcaccacc gtcgatgacg ccatcgacgc ggtggtggag gaggcgcgca   15360
actacacgcc cacgccgcca ccagtgtcca cagtggacgc ggccattcag accgtggtgc   15420
gcggagcccg cgctatgct aaaatgaaga cggcggag gcgcgtagca cgtcgccacc      15480
gccgccgacc cggcactgcc gcccaacgcg cggcggcggc cctgcttaac cgcgcacgtc   15540
```

```
gcaccggccg acgggcggcc atgcgggccg ctcgaaggct ggccgcgggt attgtcactg   15600 tgcccccag gtccaggcga cgagcggccg ccgcagcagc cgcggccatt agtgctatga   15660
ctcagggtcg caggggcaac gtgtattggg tgcgcgactc ggttagcggc ctgcgcgtgc   15720
ccgtgcgcac ccgccccccg cgcaactaga ttgcaagaaa aaactactta gactcgtact   15780
gttgtatgta tccagcggcg gcggcgcgca acgaagctat gtccaagcgc aaaatcaaag   15840
aagagatgct ccaggtcatc gcgccggaga tctatggccc cccgaagaag gaagagcagg   15900
attacaagcc ccgaaagcta agcgggtca aaaagaaaaa gaaagatgat gatgatgaac   15960
ttgacgacga ggtggaactg ctgcacgcta ccgcgcccag gcgacgggta cagtggaaag   16020
gtcgacgcgt aaaacgtgtt ttgcgacccg gcaccaccgt agtctttacg cccggtgagc   16080
gctccacccg cacctacaag cgcgtgtatg atgaggtgta cggcgacgag gacctgcttg   16140
agcaggccaa cgagcgcctc ggggagtttg cctacgaaa cggcataag gacatgctgg   16200 cgttgccgct ggacgagggc aacccaacac ctagcctaaa gcccgtaaca ctgcagcagg   16260 tgctgccgc gcttgcaccg tccgaagaaa agcgcggcct aaagcgcgag tctggtgact   16320
tggcacccac cgtgcagctg atggtaccca agcgccagcg actggaagat gtcttggaaa   16380
aaatgaccgt ggaacctggg ctggagcccg aggtccgcgt gcggcaatc aagcaggtgg   16440 cgccgggact gggcgtgcag accgtggacg ttcagatacc cactaccagt agcaccagta   16500
ttgccaccgc cacagagggc atggagacac aaacgtcccc ggttgcctca gcggtggcgg   16560
atgccgcggt gcaggcggtc gctgcggccg cgtccaagac ctctacggag gtgcaaacgg   16620
acccgtggat gtttcgcgtt tcagcccccc ggcgcccgcg ccgttcgagg aagtacggcg   16680
ccgccagcgc gctactgccc gaatatgccc tacatccttc cattgcgcct accccggct   16740 atcgtggcta cacctaccgc cccagaagac gagcaactac ccgacgccga accaccactg   16800
gaacccgccg ccgccgtcgc cgtcgccagc ccgtgctggc ccgattttcc gtgcgcaggg   16860
tggctcgcga aggaggcagg accctggtgc tgccaacagc gcgctaccac cccagcatcg   16920
tttaaaagcc ggtctttgtg gttcttgcag atatggccct cacctgccgc ctccgttttcc   16980 cggtgccggg attccgagga agaatgcacc gtaggagggg catggccggc cacggcctga   17040
cgggcggcat gcgtcgtgcg caccaccggc ggcggcgcgc gtcgcaccgt cgcatgcgcg   17100
gcggtatcct gcccctcctt attccactga tcgccgcggc gattggcgcc gtgcccggaa   17160
ttgcatccgt ggccttgcag cgcagagac actgattaaa aacaagttgc atgtggaaaa   17220
atcaaaataa aaagtctgga ctctcacgct cgcttggtcc tgtaactatt ttgtagaatg   17280
gaagacatca actttgcgtc tctggccccg cgacacggct cgcgcccgtt catgggaaac   17340
tggcaagata tcggcaccag caatatgagc ggtggcgcct tcagctgggg ctcgctgtgg   17400
agcggcatta aaaatttcgg ttccaccgtt aagaactatg cagcaaggc ctggaacagc   17460 agcacaggcc agatgctgag ggataagttg aaagagcaaa atttccaaca aaaggtggta   17520
gatggcctgg cctctggcat tagcggggtg gtggacctgg ccaaccaggc agtgcaaaat   17580
aagattaaca gtaagcttga tccccgccct cccgtagagg agcctccacc ggccgtggag   17640
acagtgtctc cagaggggcg tggcgaaaag cgtccgcgcc ccgacaggga agaaactctg   17700
gtgacgcaaa tagacgagcc tccctcgtac gaggaggcac taaagcaagg cctgcccacc   17760
acccgtccca tcgcgcccat ggctaccgga gtgctgggcc agcacacacc cgtaacgctg   17820
gacctgcctc cccccgccga cacccagcag aaacctgtgc tgccaggccc gaccgccgtt   17880
gttgtaaccc gtcctagccg cgcgtccctg cgccgcgccg ccagcggtcc gcgatcgttg   17940
```

```
cggcccgtag ccagtggcaa ctggcaaagc acactgaaca gcatcgtggg tctgggggtg   18000
caatccctga agcgccgacg atgcttctga tagctaacgt gtcgtatgtg tgtcatgtat   18060
gcgtccatgt cgccgccaga ggagctgctg agccgccgcg cgcccgcttt ccaagatggc   18120
taccccttcg atgatgccgc agtggtctta catgcacatc tcgggccagg acgcctcgga   18180
gtacctgagc cccgggctgg tgcagtttgc ccgcgccacc gagacgtact tcagcctgaa   18240
taacaagttt agaaacccca cggtggcgcc tacgcacgac gtgaccacag accggtccca   18300
gcgtttgacg ctgcggttca tccctgtgga ccgtgaggat actgcgtact cgtacaaggc   18360
gcggttcacc ctagctgtgg gtgataaccg tgtgctggac atggcttcca cgtactttga   18420
catccgcggc gtgctggaca ggggccctac ttttaagccc tactctggca ctgcctacaa   18480
cgccctggct cccaagggtg ccccaaatcc ttgcgaatgg gatgaagctg ctactgctct   18540
tgaaataaac ctagaagaag aggacgatga caacgaagac gaagtagacg agcaagctga   18600
gcagcaaaaa actcacgtat ttgggcaggc gccttattct ggtataaata ttacaaagga   18660
gggtattcaa ataggtgtcg aaggtcaaac acctaaatat gccgataaaa catttcaacc   18720
tgaacctcaa ataggagaat ctcagtggta cgaaacagaa attaatcatg cagctgggag   18780
agtcctaaaa aagactaccc caatgaaacc atgttacggt tcatatgcaa acccacaaa    18840 tgaaaatgga gggcaaggca ttcttgtaaa gcaacaaaat ggaaagctag aaagtcaagt   18900
ggaaatgcaa tttttctcaa ctactgaggc agccgcaggc aatggtgata acttgactcc   18960
taaagtggta ttgtacagtg aagatgtaga tatagaaacc ccagacactc atatttctta   19020
catgcccact attaaggaag gtaactcacg agaactaatg ggccaacaat ctatgcccaa   19080
caggcctaat tacattgctt ttagggacaa ttttattggt ctaatgtatt acaacagcac   19140
gggtaatatg ggtgttctgg cgggccaagc atcgcagttg aatgctgttg tagatttgca   19200
agacagaaac acagagcttt cataccagct tttgcttgat tccattggtg atagaaccag   19260
gtacttttct atgtggaatc aggctgttga cagctatgat ccagatgtta gaattattga   19320
aaatcatgga actgaagatg aacttccaaa ttactgcttt ccactgggag gtgtgattaa   19380
tacagagact cttaccaagg taaaacctaa aacaggtcag gaaaatggat gggaaaaaga   19440
tgctacagaa ttttcagata aaaatgaaat aagagttgga ataaattttg ccatggaaat   19500
caatctaaat gccaacctgt ggagaaattt cctgtactcc aacatagcgc tgtatttgcc   19560
cgacaagcta agtacagtc cttccaacgt aaaaatttct gataacccaa acacctacga   19620
ctacatgaac aagcgagtgg tggctcccgg gctagtggac tgctacatta accttggagc   19680
acgctggtcc cttgactata tggacaacgt caacccattt aaccaccacc gcaatgctgg   19740
cctgcgctac cgctcaatgt tgctgggcaa tggtcgctat gtgcccttcc acatccaggt   19800
gcctcagaag ttctttgcca ttaaaaacct ccttctcctg ccgggctcat acacctacga   19860
gtggaacttc aggaaggatg ttaacatggt tctgcagagc tccctaggaa atgacctaag   19920
ggttgacgga gccagcatta agtttgatag catttgcctt tacgccacct tcttccccat   19980
ggcccacaac accgcctcca cgcttgaggc catgcttaga aacgacacca acgaccagtc   20040
ctttaacgac tatctctccg ccgccaacat gctctaccct ataccccgcca acgctaccaa   20100 cgtgcccata tccatcccct cccgcaactg ggcggctttc cgcggctggg ccttcacgcg   20160
ccttaagact aaggaaaccc catcactggg ctcgggctac gacccttatt acacctactc   20220
tggctctata ccctacctag atggaacctt ttacctcaac cacaccttta agaaggtggc   20280
```

```
cattaccttt gactcttctg tcagctggcc tggcaatgac cgcctgctta cccccaacga    20340
gtttgaaatt aagcgctcag ttgacgggga gggttacaac gttgcccagt gtaacatgac    20400
caaagactgg ttcctggtac aaatgctagc taactataac attggctacc agggcttcta    20460
tatcccagag agctacaagg accgcatgta ctccttcttt agaaacttcc agcccatgag    20520
ccgtcaggtg gtggatgata ctaaatacaa ggactaccaa caggtgggca tcctacacca    20580
acacaacaac tctggatttg ttggctacct tgccccacc atgcgcgaag acaggcta     20640
ccctgctaac ttcccctatc cgcttatagg caagaccgca gttgacagca ttacccagaa    20700
aaagtttctt tgcgatcgca ccctttggcg catcccattc tccagtaact ttatgtccat    20760
gggcgcactc acagacctgg gccaaaacct tctctacgcc aactccgccc acgcgctaga    20820
catgactttt gaggtggatc ccatggacga gcccacccct ctttatgttt tgtttgaagt    20880
ctttgacgtg gtccgtgtgc accagccgca ccgcggcgtc atcgaaaccg tgtacctgcg    20940
cacgcccttc tcggccggca acgccacaac ataaagaagc aagcaacatc aacaacagct    21000
gccgccatgg gctccagtga gcaggaactg aaagccattg tcaaagatct tggttgtggg    21060
ccatattttt tgggcaccta tgacaagcgc tttccaggct ttgtttctcc acacaagctc    21120
gcctgcgcca tagtcaatac ggccggtcgc gagactgggg gcgtacactg gatggccttt    21180
gcctggaacc cgcactcaaa acatgctac ctctttgagc cctttggctt ttctgaccag    21240
cgactcaagc aggtttacca gtttgagtac gagtcactcc tgcgccgtag cgccattgct    21300
tcttcccccg accgctgtat aacgctggaa aagtccaccc aaagcgtaca ggggcccaac    21360
tcggccgcct gtggactatt ctgctgcatg tttctccacg cctttgccaa ctggcccaa     21420
actcccatgg atcacaaccc caccatgaac cttattaccg gggtacccaa ctccatgctc    21480
aacagtcccc aggtacagcc caccctgcgt cgcaaccagg aacagctcta cagcttcctg    21540
gagcgccact cgccctactt ccgcagccac agtgcgcaga ttaggagcgc cacttctttt    21600
tgtcacttga aaaacatgta aaataatgt actagagaca cttcaataa aggcaaatgc    21660
ttttatttgt acactctcgg gtgattattt accccccaccc ttgccgtctg cgccgtttaa    21720
aaatcaaagg ggttctgccg cgcatcgcta tgcgccactg gcaggacac gttgcgatac     21780
tggtgtttag tgctccactt aaactcaggc acaaccatcc gcggcagctc ggtgaagttt    21840
tcactccaca ggctgcgcac catcaccaac gcgtttagca ggtcgggcgc cgatatcttg    21900
aagtcgcagt tggggcctcc gccctgcgcg cgcgagttgc gatacacagg gttgcagcac    21960
tggaacacta tcagcgccgg gtggtgcacg ctggccagca cgctcttgtc ggagatcaga    22020
tccgcgtcca ggtcctccgc gttgctcagg gcgaacggag tcaactttgg tagctgcctt    22080
cccaaaaagg gcgcgtgccc aggctttgag ttgcactcgc accgtagtgg catcaaaagg    22140
tgaccgtgcc cggtctgggc gttaggatac agcgcctgca taaaagcctt gatctgctta    22200
aaagccacct gagcctttgc gccttcagag aagaacatgc cgcaagactt gccggaaaac    22260
tgattggccg gacaggccgc gtcgtgcacg cagcaccttg cgtcggtgtt ggagatctgc    22320
accacatttc ggccccaccg gttcttcacg atcttggcct tgctagactg ctccttcagc    22380
gcgcgctgcc cgttttcgct cgtcacatcc atttcaatca cgtgctcctt atttatcata    22440
atgcttccgt gtagacactt aagctcgcct tcgatctcag cgcagcggtg cagccacaac    22500
gcgcagcccg tgggctcgtg atgcttgtag tcacctctg caaacgactg caggtacgcc    22560
tgcaggaatc gccccatcat cgtcacaaag gtcttgttgc tggtgaaggt cagctgcaac    22620
ccgcggtgct cctcgttcag ccaggtcttg catacggccg ccagagcttc cacttggtca    22680
```

```
ggcagtagtt tgaagttcgc ctttagatcg ttatccacgt ggtacttgtc catcagcgcg   22740
cgcgcagcct ccatgccctt ctcccacgca gacacgatcg gcacactcag cgggttcatc   22800
accgtaattt cactttccgc ttcgctgggc tcttcctctt cctcttgcgt ccgcatacca   22860
cgcgccactg ggtcgtcttc attcagccgc cgcactgtgc gcttacctcc tttgccatgc   22920
ttgattagca ccggtgggtt gctgaaaccc accatttgta gcgccacatc ttctctttct   22980
tcctcgctgt ccacgattac ctctggtgat ggcgggcgct cgggcttggg agaagggcgc   23040 ttcttttttct tcttgggcgc aatggccaaa tccgccgccg aggtcgatgg ccgcgggctg   23100
ggtgtgcgcg gcaccagcgc gtcttgtgat gagtcttcct cgtcctcgga ctcgatacgc   23160
cgcctcatcc gctttttgg gggcgcccgg ggaggcggcg gcgacgggga cggggacgac   23220
acgtcctcca tggttggggg acgtcgcgcc gcaccgcgtc cgcgctcggg ggtggtttcg   23280
cgctgctcct cttcccgact ggccatttcc ttctcctata ggcagaaaaa gatcatggag   23340
tcagtcgaga agaaggacag cctaaccgcc ccctctgagt tcgccaccac cgcctccacc   23400
gatgccgcca acgcgcctac caccttcccc gtcgaggcac cccgcttga ggaggaggaa    23460 gtgattatcg agcaggaccc aggttttgta agcgaagacg acgaggaccg ctcagtacca   23520
acagaggata aaaagcaaga ccaggacaac gcagaggcaa acgaggaaca agtcgggcgg   23580
ggggacgaaa ggcatggcga ctacctagat gtgggagacg acgtgctgtt gaagcatctg   23640
cagcgccagt gcgccattat ctgcgacgcg ttgcaagagc gcagcgatgt gcccctcgcc   23700
atagcggatg tcagccttgc ctacgaacgc cacctattct caccgcgcgt accccccaaa   23760
cgccaagaaa acggcacatg cgagcccaac ccgcgcctca acttctaccc cgtatttgcc   23820
gtgccagagt gcttgccac ctatcacatc ttttttccaaa actgcaagat accectatcc    23880 tgccgtgcca accgcagccg agcggacaag cagctggcct tgcggcaggg cgctgtcata   23940
cctgatatcg cctcgctcaa cgaagtgcca aaaatctttg agggtcttgg acgcgacgag   24000
aagcgcgcgg caaacgctct gcaacaggaa acagcgaaa atgaaagtca ctctggagtg   24060
ttggtggaac tcgagggtga caacgcgcgc ctagccgtac taaaacgcag catcgaggtc   24120
acccactttg cctacccggc acttaaccta cccccaagg tcatgagcac agtcatgagt    24180
gagctgatcg tgcgccgtgc gcagcccctg gagagggatg caaatttgca agaacaaaca   24240
gaggagggcc taccgcagt tggcgacgag cagctagcgc gctggcttca aacgcgcgag   24300
cctgccgact tggaggagcg acgcaaacta atgatggccg cagtgctcgt taccgtggag   24360
cttgagtgca tgcagcggtt ctttgctgac ccggagatgc agcgcaagct agaggaaaca   24420
ttgcactaca cctttcgaca gggctacgta cgccaggcct gcaagatctc caacgtggag   24480
ctctgcaacc tggtctccta ccttggaatt ttgcacgaaa accgccttgg gcaaaacgtg   24540
cttcattcca cgctcaaggg cgaggcgcgc cgcgactacg tccgcgactg cgtttactta   24600
tttctatgct acacctggca gacgccatg ggcgtttggc agcagtgctt ggaggagtgc   24660
aacctcaagg agctgcagaa actgctaaag caaaacttga aggacctatg gacggccttc   24720
aacgagcgct ccgtggccgc gcacctggcg gacatcattt tccccgaacg cctgcttaaa   24780
accctgcaac agggtctgcc agacttcacc agtcaaagca tgttgcagaa ctttaggaac   24840
tttatcctag agcgctcagg aatcttgccc gccacctgct gtgcacttcc tagcgacttt   24900
gtgcccatta gtaccgcgga atgccctccg ccgctttggg gccactgcta ccttctgcag   24960
ctagccaact accttgccta ccactctgac ataatggaag acgtgagcgg tgacggtcta   25020
```

```
ctggagtgtc actgtcgctg caacctatgc accccgcacc gctccctggt ttgcaattcg    25080
cagctgctta acgaaagtca aattatcggt acctttgagc tgcagggtcc ctcgcctgac    25140
gaaaagtccg cggctccggg gttgaaactc actccggggc tgtggacgtc ggcttacctt    25200
cgcaaatttg tacctgagga ctaccacgcc cacgagatta ggttctacga agaccaatcc    25260
cgcccgccta atgcggagct taccgcctgc gtcattaccc agggccacat tcttggccaa    25320
ttgcaagcca tcaacaaagc ccgccaagag tttctgctac gaaagggacg ggggtttac    25380 ttggaccccc agtccggcga ggagctcaac ccaatccccc cgccgccgca gccctatcag    25440
cagcagccgc gggcccttgc ttcccaggat ggcacccaaa aagaagctgc agctgccgcc    25500
gccacccacg gacgaggagg aatactggga cagtcaggca gaggaggttt tggacgagga    25560
ggaggaggac atgatggaag actgggagag cctagacgag gaagcttccg aggtcgaaga    25620
ggtgtcagac gaaacaccgt caccctcggt cgcattcccc tcgccggcgc cccagaaatc    25680
ggcaaccggt tccagcatgg ctacaacctc cgctcctcag gcgccgccgg cactgcccgt    25740
tcgccgaccc aaccgtagat gggacaccac tggaaccagg gccggtaagt ccaagcagcc    25800
gccgccgtta gcccaagagc aacaacagcg ccaaggctac cgctcatggc gcgggcacaa    25860
gaacgccata gttgcttgct tgcaagactg tgggggcaac atctccttcg cccgccgctt    25920
tcttctctac catcacggcg tggccttccc ccgtaacatc ctgcattact accgtcatct    25980
ctacagccca tactgcaccg gcggcagcgg cagcaacagc agcggccaca cagaagcaaa    26040
ggcgaccgga tagcaagact ctgacaaagc ccagaaaatc cacagcggcg gcagcagcag    26100
gaggaggagc gctgcgtctg gcgcccaacg aacccgtatc gacccgcgag cttagaaaca    26160 ggattttttcc cactctgtat gctatatttc aacagagcag gggccaagaa caagagctga    26220
aaataaaaaa caggtctctg cgatccctca cccgcagctg cctgtatcac aaaagcgaag    26280
atcagcttcg gcgcacgctg gaagacgcgg aggctctctt cagtaaatac tgcgcgctga    26340
ctcttaagga ctagtttcgc gcccttctc aaatttaagc gcgaaaacta cgtcatctcc    26400
agcggccaca cccggcgcca gcacctgttg tcagcgccat tatgagcaag gaaattccca    26460
cgccctacat gtggagttac cagccacaaa tgggacttgc ggctggagct gcccaagact    26520
actcaacccg aataaactac atgagcgcgg accccacat gatatcccgg gtcaacggaa    26580
tacgcgccca ccgaaaccga attctcctgg aacaggcggc tattaccacc acacctcgta    26640
ataaccttaa tccccgtagt tggcccgctg ccctggtgta ccaggaaagt cccgctccca    26700
ccactgtggt acttcccaga gacgcccagg ccgaagttca gatgactaac tcaggggcgc    26760
agcttgcggg cggctttcgt cacagggtgc ggtcgcccgg gcagggtata actcacctga    26820
caatcagagg gcgaggtatt cagctcaacg acgagtcggt gagctcctcg cttggtctcc    26880
gtccggacgg gacatttcag atcggcggcg ccggccgctc ttcattcacg cctcgtcagg    26940
caatcctaac tctgcagacc tcgtcctctg agccgcgctc tggaggcatt ggaactctgc    27000
aatttattga ggagtttgtg ccatcggtct actttaaccc cttctcggga cctcccggcc    27060
actatccgga tcaatttatt cctaactttg acgcggtaaa ggactcggcg gacggctacg    27120
actgaatgtt aagtgagag gcagagcaac tgcgcctgaa acacctggtc cactgtcgcc    27180
gccacaagtg ctttgcccgc gactccggtg agttttgcta ctttgaattg cccgaggatc    27240
atatcgaggg cccggcgcac ggcgtccggc ttaccgccca gggagagctt gcccgtagcc    27300
tgattcggga gtttacccag cgcccctgc tagttgagcg ggacagggga ccctgtgttc    27360
tcactgtgat ttgcaactgt cctaaccctg gattacatca agatctttgt tgccatctct    27420
```

```
gtgctgagta taataaatac agaaattaaa atatactggg gctcctatcg ccatcctgta  27480
aacgccaccg tcttcacccg cccaagcaaa ccaaggcgaa ccttacctgg tactttaac   27540 atctctccct ctgtgattta caacagtttc aacccagacg gagtgagtct acgagagaac  27600
ctctccgagc tcagctactc catcagaaaa acaccaccc tccttacctg ccgggaacgt   27660
acgagtgcgt caccggccgc tgcaccacac ctaccgcctg accgtaaacc agactttttc  27720
cggacagacc tcaataactc tgtttaccag aacaggaggt gagcttagaa aacccttagg   27780
gtattaggcc aaaggcgcag ctactgtggg gtttatgaac aattcaagca actctacggg   27840
ctattctaat tcaggtttct ctagaatcgg ggttggggtt attctctgtc ttgtgattct   27900
ctttattctt atactaacgc ttctctgcct aaggctcgcc gcctgctgtg tgcacatttg   27960
catttattgt cagcttttta aacgctgggg tcgccaccca agatgattag gtacataatc   28020
ctaggtttac tcacccttgc gtcagcccac ggtaccaccc aaaaggtgga ttttaaggag   28080
ccagcctgta atgttacatt cgcagctgaa gctaatgagt gcaccactct tataaaatgc   28140
accacagaac atgaaaagct gcttattcgc cacaaaaaca aaattggcaa gtatgctgtt   28200 tatgctatt ggcagccagg tgacactaca gagtataatg ttacagttt ccagggtaaa    28260 agtcataaaa cttttatgta acttttcca ttttatgaaa tgtgcgacat taccatgtac    28320
atgagcaaac agtataagtt gtggcccca caaaattgtg tggaaaacac tggcactttc    28380
tgctgcactg ctatgctaat tacagtgctc gctttggtct gtaccctact ctatattaaa   28440
tacaaaagca gacgcagctt tattgaggaa aagaaaatgc cttaatttac taagttacaa   28500
agctaatgtc accactaact gctttactcg ctgcttgcaa aacaaattca aaaagttagc   28560
attataatta gaataggatt taaaccccc ggtcattcc tgctcaatac cattccctg      28620 aacaattgac tctatgtggg atatgctcca gcgctacaac cttgaagtca ggcttcctgg   28680
atgtcagcat ctgactttgg ccagcacctg tcccgcggat ttgttccagt ccaactacag   28740
cgacccaccc taacagagat gaccaacaca accaacgcgg ccgccgctac cggacttaca   28800
tctaccacaa atacaccca gtttctgcc tttgtcaata actgggataa cttgggcatg     28860
tggtggttct ccatagcgct tatgtttgta tgccttatta ttatgtggct catctgctgc   28920
ctaaagcgca acgcgcccg accacccatc tatagtccca tcattgtgct acacccaaac   28980
aatgatggaa tccatagatt ggacggactg aaacacatgt tcttttctct tacagtatga   29040
ttaaatgaga catgattcct cgagtttta tattactgac ccttgttgcg cttttttgt     29100 gcgtgctcca cattggctgc ggtttctcac atcgaagtag actgcattcc agccttcaca   29160
gtctatttgc tttacggatt tgtcacccct cgctcatct gcagcctcat cactgtggtc    29220
atcgccttta tccagtgcat tgactgggtc tgtgtgcgct ttgcatatct cagacaccat   29280
ccccagtaca gggacaggac tatagctgag cttcttagaa ttctttaatt atgaaattta   29340 ctgtgactt tctgctgatt atttgcaccc tatctgcgtt ttgttcccg acctccaagc    29400 ctcaaagaca tatatcatgc agattcactc gtatatggaa tattccaagt tgctacaatg   29460
aaaaaagcga tctttccgaa gcctggttat atgcaatcat ctctgttatg gtgttctgca   29520
gtaccatctt agccctagct atatatccct accttgacat tggctggaac gcaatagatg   29580
ccatgaacca cccaacttc cccgcgcccg ctatgcttcc actgcaacaa gttgttgccg   29640 gcggcttgt cccagccaat cagcctcgcc caccttctcc caccccact gaaatcagct    29700 actttaatct aacaggagga gatgactgac accctagatc tagaaatgga cggaattatt   29760
```

```
acagagcagc gcctgctaga aagacgcagg gcagcggccg agcaacagcg catgaatcaa    29820
gagctccaag acatggttaa cttgcaccag tgcaaaaggg gtatcttttg tctggtaaag    29880
caggccaaag tcacctacga cagtaatacc accggacacc gccttagcta caagttgcca    29940
accaagcgtc agaaattggt ggtcatggtg ggagaaaagc ccattaccat aactcagcac    30000
tcggtagaaa ccgaaggctg cattcactca ccttgtcaag gacctgagga tctctgcacc    30060
cttattaaga ccctgtgcgg tctcaaagat cttattccct ttaactaata aaaaaaaata    30120
ataaagcatc acttacttaa aatcagttag caaatttctg tccagtttat tcagcagcac    30180
ctccttgccc tcctcccagc tctggtattg cagcttcctc ctggctgcaa actttctcca    30240
caatctaaat ggaatgtcag tttcctcctg ttcctgtcca tccgcaccca ctatcttcat    30300
gttgttgcag atgaagcgcg caagaccgtc tgaagatacc ttcaaccccg tgtatccata    30360
tgacacggaa accggtcctc caactgtgcc ttttcttact cctcccttg tatcccccaa     30420
tgggtttcaa gagagtcccc ctggggtact ctctttgcgc ctatccgaac ctctagttac    30480
ctccaatggc atgcttgcgc tcaaaatggg caacggcctc tctctggacg aggccggcaa    30540
ccttacctcc caaaatgtaa ccactgtgag cccacctctc aaaaaaacca agtcaaacat    30600
aaacctggaa atatctgcac ccctcacagt tacctcagaa gccctaactg tggctgccgc    30660
cgcacctcta atggtcgcgg gcaacacact caccatgcaa tcacaggccc cgctaaccgt    30720
gcacgactcc aaacttagca ttgccaccca aggaccctc acagtgtcag aaggaaagct     30780
agccctgcaa acatcaggcc ccctcaccac caccgatagc agtaccctta ctatcactgc    30840
ctcacccct ctaactactg ccactggtag cttgggcatt gacttgaaag agcccattta     30900
tacacaaaat ggaaaactag gactaaagta cggggctcct ttgcatgtaa cagacgacct    30960
aaacactttg accgtagcaa ctggtccagg tgtgactatt aataatactt ccttgcaaac    31020
taaagttact ggagccttgg gttttgattc acaaggcaat atgcaactta atgtagcagg    31080
aggactaagg attgattctc aaaacagacg ccttatactt gatgttagtt atccgtttga    31140
tgctcaaaac caactaaatc taagactagg acagggccct cttttttataa actcagccca    31200
caacttggat attaactaca acaaaggcct ttacttgttt acagcttcaa acaattccaa    31260
aaagcttgag gttaacctaa gcactgccaa ggggttgatg tttgacgcta cagccatagc    31320
cattaatgca ggagatgggc ttgaatttgg ttcacctaat gcaccaaaca caaatccccct    31380
caaaacaaaa attggccatg cctagaatt tgattcaaac aaggctatgg ttcctaaact     31440
aggaactggc cttagttttg acagcacagg tgccattaca gtaggaaaca aaaataatga    31500
taagctaact ttgtggacca caccagctcc atctcctaac tgtagactaa atgcagagaa    31560
agatgctaaa ctcactttgg tcttaacaaa atgtggcagt caaatacttg ctacagtttc    31620
agttttggct gttaaaggca gtttggctcc aatatctgga acagttcaaa gtgctcatct    31680
tattataaga tttgacgaaa atggagtgct actaaacaat tccttcctgg acccagaata    31740
ttggaacttt agaaatggag atcttactga aggcacagcc tatacaaacg ctgttggatt    31800
tatgcctaac ctatcagctt atccaaaatc tcacggtaaa actgccaaaa gtaacattgt    31860
cagtcaagtt tacttaaacg gagacaaaac taaacctgta acactaacca ttacactaaa    31920
cggtacacag gaaacaggag acacaactcc aagtgcatac tctatgtcat ttcatggga     31980
ctggtctggc cacaactaca ttaatgaaat atttgccaca tcctcttaca cttttttcata    32040
cattgcccaa gaataaagaa tcgtttgtgt tatgtttcaa cgtgtttatt tttcaattgc    32100
agaaaatttc aagtcatttt tcattcagta gtatagcccc accaccacat agcttataca    32160
```

```
gatcaccgta ccttaatcaa actcacagaa ccctagtatt caacctgcca cctccctccc    32220
aacacacaga gtacacagtc ctttctcccc ggctggcctt aaaaagcatc atatcatggg    32280
taacagacat attcttaggt gttatattcc acacggtttc ctgtcgagcc aaacgctcat    32340
cagtgatatt aataaactcc ccgggcagct cacttaagtt catgtcgctg tccagctgct    32400
gagccacagg ctgctgtcca acttgcggtt gcttaacggg cggcgaagga gaagtccacg    32460
cctacatggg ggtagagtca taatcgtgca tcaggatagg gcggtggtgc tgcagcagcg    32520
cgcgaataaa ctgctgccgc cgccgctccg tcctgcagga atacaacatg gcagtggtct    32580
cctcagcgat gattcgcacc gcccgcagca taaggcgcct tgtcctccgg gcacagcagc    32640
gcaccctgat ctcacttaaa tcagcacagt aactgcagca cagcaccaca atattgttca    32700
aaatcccaca gtgcaaggcg ctgtatccaa agctcatggc ggggaccaca gaacccacgt    32760
ggccatcata ccacaagcgc aggtagatta agtggcgacc cctcataaac acgctggaca    32820
taaacattac ctcttttggc atgttgtaat tcaccacctc ccgtaccat ataaacctct    32880 gattaaacat ggcgccatcc accaccatcc taaaccagct ggccaaaacc tgcccgccgg    32940
ctatacactg cagggaaccg ggactggaac aatgacagtg gagagcccag gactcgtaac    33000
catggatcat catgctcgtc atgatatcaa tgttggcaca acacaggcac acgtgcatac    33060
acttcctcag gattacaagc tcctcccgcg ttagaaccat atcccaggga acaacccatt    33120
cctgaatcag cgtaaatccc acactgcagg gaagacctcg cacgtaactc acgttgtgca    33180
ttgtcaaagt gttacattcg ggcagcagcg gatgatcctc cagtatggta gcgcgggttt    33240
ctgtctcaaa aggaggtaga cgatccctac tgtacggagt gcgccgagac aaccgagatc    33300
gtgttggtcg tagtgtcatg ccaaatggaa cgccggacgt agtcatattt cctgaagcaa    33360
aaccaggtgc gggcgtgaca aacagatctg cgtctccggt ctcgccgctt agatcgctct    33420
gtgtagtagt tgtagtatat ccactctctc aaagcatcca ggcgccccct ggcttcgggt    33480
tctatgtaaa ctccttcatg cgccgctgcc ctgataacat ccaccaccgc agaataagcc    33540
acacccagcc aacctacaca ttcgttctgc gagtcacaca cgggaggagc gggaagagct    33600
ggaagaacca tgttttttt tttattccaa aagattatcc aaaacctcaa aatgaagatc    33660
tattaagtga acgcgctccc ctccggtggc gtggtcaaac tctacagcca agaacagat    33720 aatggcattt gtaagatgtt gcacaatggc ttccaaaagg caaacggccc tcacgtccaa    33780
gtggacgtaa aggctaaacc cttcagggtg aatctcctct ataaacattc cagcaccttc    33840
aaccatgccc aaataattct catctcgcca ccttctcaat atatctctaa gcaaatcccg    33900
aatattaagt ccggccattg taaaaatctg ctccagagcg ccctccacct tcagcctcaa    33960
gcagcgaatc atgattgcaa aaattcaggt tcctcacaga cctgtataag attcaaaagc    34020
ggaacattaa caaaaatacc gcgatcccgt aggtcccttc gcagggccag ctgaacataa    34080
tcgtgcaggt ctgcacggac cagcgcggcc acttccccgc caggaaccat gacaaaagaa    34140
cccacactga ttatgacacg catactcgga gctatgctaa ccagcgtagc cccgatgtaa    34200
gcttgttgca tgggcggcga tataaaatgc aaggtgctgc tcaaaaaatc aggcaaagcc    34260
tcgcgcaaaa aagaaagcac atcgtagtca tgctcatgca gataaaggca ggtaagctcc    34320
ggaaccacca cagaaaaaga caccatttt ctctcaaaca tgtctgcggg tttctgcata    34380
aacacaaaat aaaataacaa aaaaacattt aaacattaga agcctgtctt acaacaggaa    34440 aaacaacccct tataagcata agacggacta cggccatgcc ggcgtgaccg taaaaaaact    34500
```

-continued

```
ggtcaccgtg attaaaaagc accaccgaca gctcctcggt catgtccgga gtcataatgt      34560
aagactcggt aaacacatca ggttgattca catcggtcag tgctaaaaag cgaccgaaat      34620
agcccggggg aatacatacc cgcaggcgta gagacaacat tacagccccc ataggaggta      34680
taacaaaatt aataggagag aaaaacacat aaacacctga aaaaccctcc tgcctaggca      34740
aaatagcacc ctcccgctcc agaacaacat acagcgcttc cacagcggca gccataacag      34800
tcagccttac cagtaaaaaa gaaaacctat taaaaaaaca ccactcgaca cggcaccagc      34860
tcaatcagtc acagtgtaaa aaagggccaa gtgcagagcg agtatatata ggactaaaaa      34920
atgacgtaac ggttaaagtc cacaaaaaac acccagaaaa ccgcacgcga acctacgccc      34980
agaaacgaaa gccaaaaaac ccacaacttc ctcaaatcgt cacttccgtt ttcccacgtt      35040
acgtcacttc ccattttaag aaaactacaa ttcccaacac atacaagtta ctccgcccta      35100
aaacctacgt cacccgcccc gttcccacgc cccgcgccac gtcacaaact ccacccctc      35160 attatcatat tggcttcaat ccaaaataag gtatattatt gatgatg                   35207
```

<210> SEQ ID NO 20

<400> SEQUENCE: 20

000

<210> SEQ ID NO 21

<400> SEQUENCE: 21

000

<210> SEQ ID NO 22
<211> LENGTH: 19
<212> TYPE: DNA
<213> ORGANISM: Artificial Sequence
<220> FEATURE:
<223> OTHER INFORMATION: Endothelial Cell-Specific Enhancer Element

<400> SEQUENCE: 22
ggtgactttg cttctggag                                                    19

<210> SEQ ID NO 23
<211> LENGTH: 19
<212> TYPE: DNA
<213> ORGANISM: Artificial Sequence
<220> FEATURE:
<223> OTHER INFORMATION: Endothelial Cell-Specific Enhancer Element

<400> SEQUENCE: 23
ctccagaagc aaagtcacc                                                    19

<210> SEQ ID NO 24
<211> LENGTH: 19
<212> TYPE: DNA
<213> ORGANISM: Artificial Sequence
<220> FEATURE:
<223> OTHER INFORMATION: Endothelial Cell-Specific Enhancer Element

<400> SEQUENCE: 24
gtacttcata cttttcatt                                                    19

<210> SEQ ID NO 25
<211> LENGTH: 19
<212> TYPE: DNA
<213> ORGANISM: Artificial Sequence

```
<220> FEATURE:
<223> OTHER INFORMATION: Endothelial Cell-Specific Enhancer Element

<400> SEQUENCE: 25
aatgaaaagt atgaagtac                                                    19

<210> SEQ ID NO 26
<211> LENGTH: 6
<212> TYPE: DNA
<213> ORGANISM: Artificial Sequence
<220> FEATURE:
<223> OTHER INFORMATION: Hypoxia Response element

<400> SEQUENCE: 26 gcacgt                                                                   6

<210> SEQ ID NO 27
<211> LENGTH: 40
<212> TYPE: PRT
<213> ORGANISM: Artificial Sequence
<220> FEATURE:
<223> OTHER INFORMATION: peptide linker

<400> SEQUENCE: 27

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser
        35                  40

<210> SEQ ID NO 28
<211> LENGTH: 10
<212> TYPE: PRT
<213> ORGANISM: Artificial Sequence
<220> FEATURE:
<223> OTHER INFORMATION: VH CDR1

<400> SEQUENCE: 28

Gly Tyr Thr Phe Thr Asn Tyr Gly Met Asn
1               5                   10

<210> SEQ ID NO 29
<211> LENGTH: 17
<212> TYPE: PRT
<213> ORGANISM: Artificial Sequence
<220> FEATURE:
<223> OTHER INFORMATION: VH CDR2

<400> SEQUENCE: 29

Trp Ile Asn Thr Tyr Thr Gly Glu Pro Thr Tyr Ala Ala Asp Phe Lys
1               5                   10                  15

Arg

<210> SEQ ID NO 30
<211> LENGTH: 14
<212> TYPE: PRT
<213> ORGANISM: Artificial Sequence
<220> FEATURE:
<223> OTHER INFORMATION: VH CDR3

<400> SEQUENCE: 30

Tyr Pro His Tyr Tyr Gly Ser Ser His Trp Tyr Phe Asp Val
1               5                   10
```

```
<210> SEQ ID NO 31
<211> LENGTH: 11
<212> TYPE: PRT
<213> ORGANISM: Artificial Sequence
<220> FEATURE:
<223> OTHER INFORMATION: VL CDR1

<400> SEQUENCE: 31

Ser Ala Ser Gln Asp Ile Ser Asn Tyr Leu Asn
1               5                   10

<210> SEQ ID NO 32
<211> LENGTH: 7
<212> TYPE: PRT
<213> ORGANISM: Artificial Sequence
<220> FEATURE:
<223> OTHER INFORMATION: VL CDR2

<400> SEQUENCE: 32

Phe Thr Ser Ser Leu His Ser
1               5

<210> SEQ ID NO 33
<211> LENGTH: 9
<212> TYPE: PRT
<213> ORGANISM: Artificial Sequence
<220> FEATURE:
<223> OTHER INFORMATION: VL CDR3

<400> SEQUENCE: 33

Gln Gln Tyr Ser Thr Val Pro Trp Thr
1               5
```

METHODS OF INDUCING RESPONSIVENESS TO ANTI-ANGIOGENIC AGENT

REFERENCE TO RELATED APPLICATIONS

This application is a continuation of U.S. patent application No. Ser. 15/607,083, now U.S. Pat. No. 10,383,954, which is continuation of U.S. patent application Ser. No. 14/767,977, now U.S. Pat. No. 9,682,154, which is a U.S. national stage entry of PCT Application No. PCT/IB2014/000704, filed Feb. 4, 2014, which claims the benefit of U.S. Provisional Patent Application Nos. 61/907,286, filed Nov. 21, 2013; 61/858,467, filed Jul. 25, 2013; 61/800,716, filed Mar. 15, 2013; and 61/760,601, filed Feb. 4, 2013. The contents of the above applications are all incorporated by reference in their entireties.

REFERENCE TO SEQUENCE LISTING SUBMITTED ELECTRONICALLY

The content of the electronically submitted sequence listing in ASCII text file (Name: 3182_0530006_Seq-Listing_ST25, Size: 73,907 bytes; and Date of Creation: Jul. 5, 2019), filed herewith, is incorporated herein by reference in its entirety.

BACKGROUND OF THE DISCLOSURE

Angiogenesis is a common and major feature of several pathologies. Among these are diseases in which the angiogenesis can improve the disease condition (such as ischemic heart disease) and diseases in which the excessive angiogenesis is a part of the pathology and thus should be eliminated. These latter diseases include diabetes (diabetic retinopathy), cardiovascular diseases (atherosclerosis), chronic inflammation (rheumatoid arthritis), and cancer. Angiogenesis occurs in tumors and permits their growth, invasion and metastasis. In 1971, Folkman proposed that tumor growth and metastases are angiogenesis dependent, and thus inhibiting angiogenesis may be a strategy to arrest tumor growth.

There are several molecules involved in angiogenesis, from transcription factors to growth factors. Hypoxia is an important environmental factor that leads to neovascularization, and it induces release of several cytokines release that are pro-angiogenic factors. Among them are vascular endothelial growth factors (VEGF) and their receptors, members of the angiopoietin family, basic fibroblast growth factor, and endothelin-1 (ET-1). These factors are involved in induction of angiogenesis through activation, proliferation and migration of endothelial cells.

Recombinant forms of endogenous inhibitors of angiogenesis were tested for the treatment of cancer. The potential pharmacokinetic, biotechnological and economic drawbacks of chronic delivery of these recombinant inhibitors have led scientists to develop other approaches.

The development of the anti-VEGF monoclonal antibody bevacizumab has validated an antiangiogenic approach as a complementary therapeutic modality to chemotherapy. Several small molecule inhibitors, including second-generation multi-targeted tyrosine kinase inhibitors, have also shown promise as antiangiogenic agents for cancer.

However, the potential pharmacokinetic and economic drawbacks of chronic delivery of recombinant inhibitors, antibodies, and small molecules, as well as the limited activity manifested when applied as monotherapy have led scientists to evaluate antiangiogenic gene therapy. Gene therapy is an emerging modality for treating inherited and acquired human diseases. However, there are a number of obstacles limiting successful gene therapy, including duration of expression, induction of the immune response, cytotoxicity of the vectors and tissue specificity. Two general strategies for the cancer gene therapy were proposed: tumor directed or systemic gene therapy. The lack of success in targeting gene therapy products to cancerous cells or their environment by systemic treatments caused most therapies to be administered to the tumor itself.

BRIEF SUMMARY OF DISCLOSURE

The present invention is directed to a method for inducing or improving responsiveness to a vascular endothelial growth factor (VEGF) antagonist in a subject in need thereof, comprising administering a vector which comprises a Fas-chimera gene operably linked to an endothelial cell specific promoter, and the VEGF antagonist to the subject, wherein the responsiveness to the VEGF antagonist is induced or improved after the administration of the vector compared to the responsiveness to the VEGF antagonist without the administration of the vector. The invention is further directed to a method for inducing or improving responsiveness to a VEGF antagonist in a subject population in need thereof, comprising administering a vector which comprises a Fas-chimera gene operably linked to an endothelial cell specific promoter and the VEGF antagonist to the subject, wherein the responsiveness to the VEGF antagonist is induced or improved after the administration of the vector compared to the responsiveness to the VEGF antagonist without the administration of the vector.

In one aspect, the subject or the subject population is in need of inducing or improving responsiveness to a VEGF antagonist. In one embodiment, the responsiveness to the VEGF antagonist is an anti-angiogenesis property of the VEGF antagonist. In another embodiment, the responsiveness to the VEGF antagonist is an anti-tumor effect of the VEGF antagonist.

In another aspect, the VEGF antagonist is an anti-VEGF antibody or a VEGF binding molecule. In one aspect of the present invention, the VEGF antagonist is bevacizumab.

In some aspects, the vector comprising a Fas-chimera gene encodes a polypeptide comprising an extracellular domain of a TNF Receptor 1 (TNFR1) polypeptide fused to a transmembrane domain and an intracellular domain of a Fas polypeptide.

One feature of the present invention is that the vector and the VEGF antagonist are administered concurrently or sequentially. Another feature of the invention is that the vector is administered prior to the VEGF antagonist.

In one embodiment, the vector is administered at an effective amount of equal to or less than about $1 \times 10^{13}$, $9 \times 10^{12}$, $8 \times 10^{12}$, $7 \times 10^{12}$, $6 \times 10^{12}$, $5 \times 10^{12}$, $4 \times 10^{12}$, $3 \times 10^{12}$, $2 \times 10^{12}$, $1 \times 10^{12}$, $9 \times 10^{11}$, $8 \times 10^{11}$, $7 \times 10^{11}$, $6 \times 10^{11}$, $5 \times 10^{11}$, $4 \times 10^{11}$, $3 \times 10^{11}$, $2 \times 10^{11}$, $1 \times 10^{11}$, $9 \times 10^{10}$, $8 \times 10^{10}$, $7 \times 10^{10}$, $6 \times 10^{10}$, $5 \times 10^{10}$, $4 \times 10^{10}$, $3 \times 10^{10}$, $2 \times 10^{10}$, or $1 \times 10^{10}$ virus particles.

In one embodiment, the vector is administered at an effective amount of at least about $1 \times 10^{11}$ virus particles. In another embodiment, the vector is administered at an effective amount of at least about $1 \times 10^{12}$ virus particles. In another embodiment, the vector is administered at an effective amount of at least about $1 \times 10^{13}$ virus particles. In another embodiment, the vector is administered at an effective amount of at least about $1 \times 10^{14}$ virus particles.

In another embodiment of the present invention, bevacizumab is administered at an effective amount of equal to or less than about 15 mg/kg, 14 mg/kg, 13 mg/kg, 12 mg/kg, 11 mg/kg, 10 mg/kg, 9 mg/kg, 8 mg/kg, 7 mg/kg, 6 mg/kg, 5 mg/kg, 4 mg/kg, 3 mg/kg, 2 mg/kg, or 1 mg/kg.

In another embodiment of the present invention, the vector is administered at an effective amount of $3 \times 10^{12}$ to $1 \times 10^{13}$ virus particles and bevacizumab is administered at an effective amount of 5 mg/kg to 15 mg/kg.

In other embodiments, the VEGF antagonist is an anti-VEGF receptor binding antibody or a VEGF receptor binding molecule. In another embodiment, the anti-VEGF receptor binding antibody is a monoclonal antibody, a humanized antibody, a human antibody, a single chain antibody, or a chimeric antibody. For example, a VEGF antagonist can be selected from bevacizumab, ranibizumab, VGX-100, r84, aflibercept, IMC-18F1, IMC-1C11, ramucirumab, and any combination thereof.

In some embodiments, the vector is repeatedly administered. The vector can be repeatedly administered every day, once in about 2 days, once in about 3 days, once in about 4 days, once in about 5 days, once in about 6 days, once in about 7 days, once in about 2 weeks, once in about 3 weeks, once in about 4 weeks, once in about 5 weeks, once in about 6 weeks, once in about 7 weeks, once in about 2 months, or once in about 6 months. In certain embodiments, the bevacizumab is repeatedly administered. In another embodiment of the invention, the bevacizumab is repeatedly administered once in about 7 days, once in about 2 weeks, once in about 3 weeks, once in about 4 weeks, once in about 2 months, once in about 3 months, once in about 4 months, once in about 5 months, or once in about 6 months.

EMBODIMENTS

E1. A method of inducing apoptosis of an endothelial cell in a tumor of a subject in need thereof comprising administering a VEGF antagonist to the subject, wherein the subject is administered with a vector which comprises a Fas-chimera gene operably linked to an endothelial cell specific promoter prior to the administration of the VEGF antagonist and wherein the responsiveness of the subject to the VEGF antagonist is increased after administration of the vector.

E2. A method of inducing apoptosis of an endothelial cell in a tumor of a subject in need thereof comprising:
  (i) administering a vector which comprises a Fas-chimera gene operably linked to an endothelial cell specific promoter, wherein the responsiveness of the subject to a VEGF antagonist is increased after administration of the vector, and
  (ii) administering the VEGF antagonist to the subject.

E3. A method of inducing apoptosis of an endothelial cell in a tumor of a subject in need thereof comprising:
  (i) administering a vector which comprises a Fas-chimera gene operably linked to an endothelial cell specific promoter,
  (ii) administering a VEGF antagonist to the subject, and
  (iii) measuring responsiveness of the subject to the VEGF antagonist, wherein the responsiveness of the subject is increased after the administration of the vector.

E4. The method of any one of embodiments E1 to E3, wherein the tumor size of the subject is reduced after the administration of the VEGF antagonist.

E5. A method of reducing the size of a tumor in a subject in need thereof comprising administering a VEGF antagonist to the subject, wherein the subject is administered with a vector which comprises a Fas-chimera gene operably linked to an endothelial cell specific promoter prior to the administration of the VEGF antagonist, wherein the responsiveness of the subject to the VEGF antagonist is increased after administration of the vector and before administration of the VEGF antagonist, and wherein the tumor size in the subject is reduced after administration of the VEGF antagonist.

E6. A method of reducing the size of a tumor in a subject in need thereof comprising:
  (i) administering a vector which comprises a Fas-chimera gene operably linked to an endothelial cell specific promoter, wherein the responsiveness of the subject to a VEGF antagonist is increased after the administration of the vector, and
  (ii) administering the VEGF antagonist to the subject, wherein the tumor size in the subject is reduced after administration of the VEGF antagonist.

E7. A method of reducing the size of a tumor in a subject in need thereof comprising:
  (i) administering a vector which comprises a Fas-chimera gene operably linked to an endothelial cell specific promoter,
  (ii) administering a VEGF antagonist to the subject; and
  (iii) measuring the responsiveness of the subject to the VEGF antagonist, wherein the responsiveness of the subject to the VEGF antagonist is increased after the administration of the vector.

E8. The method of any one of embodiments E4 to E7, wherein the tumor size is reduced compared to the tumor size of a subject who is not administered with the vector prior to the administration of the VEGF antagonist.

E9. The method of any one of embodiments E4 to E8, wherein the tumor size is measured by comparing the size of the tumor prior to the administration of the VEGF antagonist and the size of the tumor after the administration of the VEGF antagonist.

E10. A method of treating a disease or condition associated with tumor in a subject comprising administering a VEGF antagonist to a subject in need thereof, wherein the subject is administered with a vector which comprises a Fas-chimera gene operably linked to an endothelial cell specific promoter prior to the administration of the VEGF antagonist and wherein the responsiveness of the subject to the VEGF antagonist is increased after administration of the vector and before administration of the VEGF antagonist.

E11. A method of treating a disease or condition associated with tumor in a subject comprising
  (i) administering a vector which comprises a Fas-chimera gene operably linked to an endothelial cell specific promoter, wherein the responsiveness of the subject to a VEGF antagonist is increased after the administration of the vector, and
  (ii) administering the VEGF antagonist to the subject.

E12. A method of treating a disease or condition associated with tumor in a subject comprising
  (i) administering a vector which comprises a Fas-chimera gene operably linked to an endothelial cell specific promoter,
  (ii) administering a VEGF antagonist to the subject; and
  (iii) measuring responsiveness of the subject to the VEGF antagonist, wherein the responsiveness of the subject to the VEGF antagonist is increased after administration of the vector.

E13. The method of any one of embodiments E1 to E12, wherein the tumor of the subject is progressed after the administration of the vector.

E14. A method of identifying a candidate for a VEGF antagonist therapy comprising (i) measuring a tumor size of a subject who is diagnosed as having a tumor prior to administering a vector which comprises a Fas-chimera gene operably linked to an endothelial cell specific promoter to the subject and (ii) measuring progression of the tumor after the administration of the vector, wherein the subject is identified as a candidate after the tumor is progressed.

E15. A method of identifying a candidate for a VEGF antagonist therapy comprising (i) measuring a tumor size of a subject who is diagnosed as having a tumor prior to administering a vector which comprises a Fas-chimera gene operably linked to an endothelial cell specific promoter to the subject, (ii) measuring progression of the tumor after the administration of the vector, wherein the subject is identified as a candidate after the tumor is progressed, and (iii) instructing a healthcare provider to administer a VEGF antagonist to the subject.

E16. The method of any one of embodiments E13 to E15, wherein the tumor progression is measured by the growth of the tumor.

E17. The method of embodiment E16, wherein the growth of the tumor is measured by MRI.

E18. The method of any one of embodiments E1 to E17, wherein the tumor of the subject is a recurrent tumor that arose during treatment with the vector.

E19. The method of any one of embodiments E1 to E18, wherein the tumor of the subject is a metastatic tumor that arose during treatment with the vector.

E20. The method of any one of embodiments E13-E19, wherein the tumor progression is measured at least three weeks, at least four weeks, at least one month, at least five weeks, at least six weeks, at least seven weeks, at least eight weeks, at least nine weeks, at least ten weeks, at least 11 weeks, at least 12 weeks, at least 13 weeks, at least 14 weeks, at least 15 weeks, or at least 16 weeks after administration of the vector.

E21. The method of any one of embodiments E1 to E20, wherein the tumor size is measured at least one week, at least two weeks, at least three weeks, at least four weeks, at least five weeks, at least six weeks, at least seven weeks, or at least eight weeks prior to administration of the vector.

E22. The method of any one of embodiments E1 to E21, wherein the VEGF antagonist is repeatedly administered after identifying that the tumor of the subject is progressed.

E23. The method of embodiment E22, wherein the VEGF antagonist is repeatedly administered once in about 7 days, once in about ten days, once in about 2 weeks, once in about 3 weeks, once in about 4 weeks, once in about 2 months, once in about 3 months, once in about 4 months, once in about 5 months, or once in about 6 months.

E24. The method of embodiment E22, wherein the VEGF antagonist is repeatedly administered once in about two weeks.

E25. The method of any one of embodiments E1 to E24, wherein the vector is repeatedly administered after administering the VEGF antagonist.

E26. The method of embodiment E25, wherein the vector is repeatedly administered every day, once in about 2 days, once in about 3 days, once in about 4 days, once in about 5 days, once in about 6 days, once in about 7 days, once in about 2 weeks, once in about 3 weeks, once in about 4 weeks, once in about 5 weeks, once in about 6 weeks, once in about 7 weeks, once in about 8 weeks, once in about 9 weeks, once in about 2 months, once in about 3 months, once in about 4 months, once in about 5 months, or once in about 6 months.

E27. The method of any one of embodiments E1 to E26, wherein the vector is administered every 2 months and bevacizumab is administered every 2 weeks.

E28. The method of any one of embodiments E1 to E27, wherein the subject is in need of induced responsiveness to a VEGF antagonist.

E29. The method of any one of embodiments E1 to E27, wherein the subject is in need of improved responsiveness to a VEGF antagonist.

E30. The method of any one of embodiments E1 to E29, wherein the responsiveness of the subject to the VEGF antagonist is an anti-angiogenesis property of the VEGF antagonist.

E31. The method of any one of embodiments E1 to E30, wherein the responsiveness of the subject to the VEGF antagonist is an anti-tumor effect of the VEGF antagonist.

E32. The method of any one of embodiments E1 to E31, wherein the VEGF antagonist is an anti-VEGF antibody or a VEGF binding molecule.

E33. The method of embodiment E32, wherein the anti-VEGF antibody is a monoclonal antibody, a humanized antibody, a human antibody, a single chain antibody, or a chimeric antibody.

E34. The method of any one of embodiments E1 to E33, wherein the VEGF antagonist comprises Fab, F(ab)2, Fv, or scFv.

E35. The method of any one of embodiments E1 to E34, wherein the VEGF antagonist is an anti-VEGF receptor binding antibody or a VEGF receptor binding molecule.

E36. The method of any one of embodiments E1 to E35, wherein the VEGF antagonist is selected from bevacizumab, ranibizumab, VGX-100, r84, aflibercept, IMC-18F1, IMC-1C11, ramucirumab, and any combination thereof.

E37. The method of embodiment E36, wherein the VEGF antagonist is bevacizumab.

E38. The method of any one of embodiments E1 to E37, wherein the Fas-chimera gene product comprises a polypeptide comprising an extracellular domain of a TNF Receptor 1 (TNFR1) polypeptide fused to a transmembrane domain and an intracellular domain of a Fas polypeptide.

E39. The method of embodiment E38, wherein the extracellular domain of the TNFR1 comprises an amino acid sequence at least 70%, 80%, 90%, 95%, 96%, 97%, 98%, 99%, or 100% identical to SEQ ID NO: 4, wherein the extracellular domain of the TNFR1 is capable of binding to TNF-α.

E40. The method of embodiment E39, wherein the trans-membrane domain and the intracellular domain of the Fas polypeptide comprises an amino acid sequence at least 70%, 80%, 90%, 95%, 96%, 97%, 98%, 99%, or 100% identical to SEQ ID NO: 8, wherein the trans-membrane domain and the intracellular domain of the Fas polypeptide is capable of inducing Fas mediated apoptosis.

E41. The method of any one of embodiments E1 to E40, wherein the Fas-chimera gene comprises a first nucleotide sequence, which is at least 70%, 80%, 90%, 95%, 96%, 97%, 98%, 99%, or 100% identical to SEQ ID NO: 3, and a second nucleotide sequence, which is at least 70%, 80%, 90%, 95%, 96%, 97%, 98%, 99%, or 100% identical to SEQ ID NO: 7.

E42. The method of any one of embodiments E1 to E41, wherein the endothelial cell specific promoter comprises a PPE-1 promoter.

E43. The method of any one of embodiments E1 to E42, wherein the endothelial cell specific promoter further comprises an enhancer.

E44. The method of embodiment E43, wherein the enhancer comprises a nucleotide sequence at least 70%, 80%, 90%, 95%, 96%, 97%, 98%, 99%, or 100% identical to SEQ ID NO: 15 or SEQ ID NO: 16, wherein the enhancer induces an improved endothelial cell specificity compared to an endothelial cell specific promoter without the enhancer.

E45. The method of embodiment E44, wherein the enhancer comprises SEQ ID NO: 11 or SEQ ID NO: 12.

E46. The method of embodiment E45, wherein the enhancer further comprises SEQ ID NO: 13 or SEQ ID NO: 14.

E47. The method of any one of embodiments E1 to E46, wherein the endothelial cell specific promoter is a PPE-1-3X promoter.

E48. The method of embodiment E47, wherein the PPE-1-3X promoter comprises a nucleotide sequence at least 70%, 80%, 90%, 95%, 96%, 97%, 98%, 99%, or 100% identical to SEQ ID NO: 18, wherein the PPE-1-3X promoter is capable of directing the Fas-chimera gene expression in endothelial cells.

E49. The method of any one of embodiments E1 to E48, wherein the vector does not contain an E1 region of an adenovirus.

E50. The method of any one of embodiments E1 to E49, wherein the vector and the VEGF antagonist are administered concurrently or sequentially.

E51. The method of embodiment E50, wherein the vector is administered prior to the VEGF antagonist.

E52. The method of any one of embodiments E1 to E51, wherein the vector is administered at an effective amount of equal to or less than about $1 \times 10^{13}$, $9 \times 10^{12}$, $8 \times 10^{12}$, $7 \times 10^{12}$, $6 \times 10^{12}$, $5 \times 10^{12}$, $4 \times 10^{12}$, $3 \times 10^{12}$, $2 \times 10^{12}$, $1 \times 10^{12}$, $9 \times 10^{11}$, $8 \times 10^{11}$, $7 \times 10^{11}$, $6 \times 10^{11}$, $5 \times 10^{11}$, $4 \times 10^{11}$, $3 \times 10^{11}$, $2 \times 10^{11}$, $1 \times 10^{11}$, $9 \times 10^{10}$, $8 \times 10^{10}$, $7 \times 10^{10}$, $6 \times 10^{10}$, $5 \times 10^{10}$, $4 \times 10^{10}$, $3 \times 10^{10}$, $2 \times 10^{10}$, or $1 \times 10^{10}$ virus particles.

E53. The method of any one of embodiments E36 to E52, wherein bevacizumab is administered at an effective amount of less than about 15 mg/kg, 14 mg/kg, 13 mg/kg, 12 mg/kg, 11 mg/kg, 10 mg/kg, 9 mg/kg, 8 mg/kg, 7 mg/kg, 6 mg/kg, 5 mg/kg, 4 mg/kg, 3 mg/kg, 2 mg/kg, or 1 mg/kg.

E54. The method of any one of embodiments E36 to E53, wherein the vector is administered at an effective amount of $3 \times 10^{12}$ to 1 to $10^{13}$ virus particles and bevacizumab is administered at an effective amount of 5 mg/kg to 15 mg/kg.

E55. The method of any one of embodiments E32 to E54, wherein the anti-VEGF antibody or the VEGF binding molecule comprises at least one CDR selected from the group consisting of $V_H$ CDR1 (SEQ ID NO: 28), $V_H$ CDR2 (SEQ ID NO: 29), $V_H$ CDR3 (SEQ ID NO: 30), $V_L$ CDR1 (SEQ ID NO: 31), $V_H$ CDR2 (SEQ ID NO: 32), $V_H$ CDR3 (SEQ ID NO: 33), and any combination thereof.

E56. The method of embodiment E55, wherein the anti-VEGF antibody or the VEGF binding molecule comprises $V_H$ CDR1 (SEQ ID NO: 28), $V_H$ CDR2 (SEQ ID NO: 29), and $V_H$ CDR3 (SEQ ID NO: 30).

E57. The method of embodiment E55, wherein the anti-VEGF antibody or the VEGF binding molecule comprises $V_L$ CDR1 (SEQ ID NO: 31), $V_L$ CDR2 (SEQ ID NO: 32), and $V_L$ CDR3 (SEQ ID NO: 33).

E58. The method of embodiment E55, wherein the anti-VEGF antibody or VEGF binding molecule comprises $V_H$ CDR1 (SEQ ID NO: 28), $V_H$ CDR2 (SEQ ID NO: 29), $V_H$ CDR3 (SEQ ID NO: 30), $V_L$ CDR1 (SEQ ID NO: 31), $V_L$ CDR2 (SEQ ID NO: 32), and $V_L$ CDR3 (SEQ ID NO: 33).

E59. The method of any one of embodiments E1 to E58, wherein the subject is in need of a reduction of angiogenesis.

E60. The method of embodiment E59, wherein the vector and the VEGF antagonist reduce angiogenesis.

E61. The method of any one of embodiments E1 to E60, wherein the vector is an adenovirus vector.

E62. The method of embodiment E61, wherein the adenovirus vector is adenovirus serotype 5.

E63. The method of any one of embodiments E1 to E62, wherein the vector comprises, consists of, or consists essentially of SEQ ID NO: 19.

E64. The method of any one of embodiments E1 to E63, wherein the vector is an isolated virus having European Collection of Cell Cultures (ECACC) Accession Number 13021201.

E65. The method of any one of embodiments E1 to E64, wherein the promoter comprises a hypoxia response element.

E66. The method of any one of embodiments E1 to E65, wherein the vector is administered at an effective amount of about $1 \times 10^{11}$, about $1 \times 10^{12}$, about $1 \times 10^{13}$, or about $1 \times 10^{14}$ virus particles.

E67. The method of any one of embodiments E1 to E66, wherein the tumor is a brain tumor.

E68. The method of embodiment E67, wherein the brain tumor is glioblastoma multiforme.

BRIEF DESCRIPTION OF THE DRAWINGS/FIGURES

DETAILED DESCRIPTION OF THE INVENTION

I. Definitions

Figure 1:
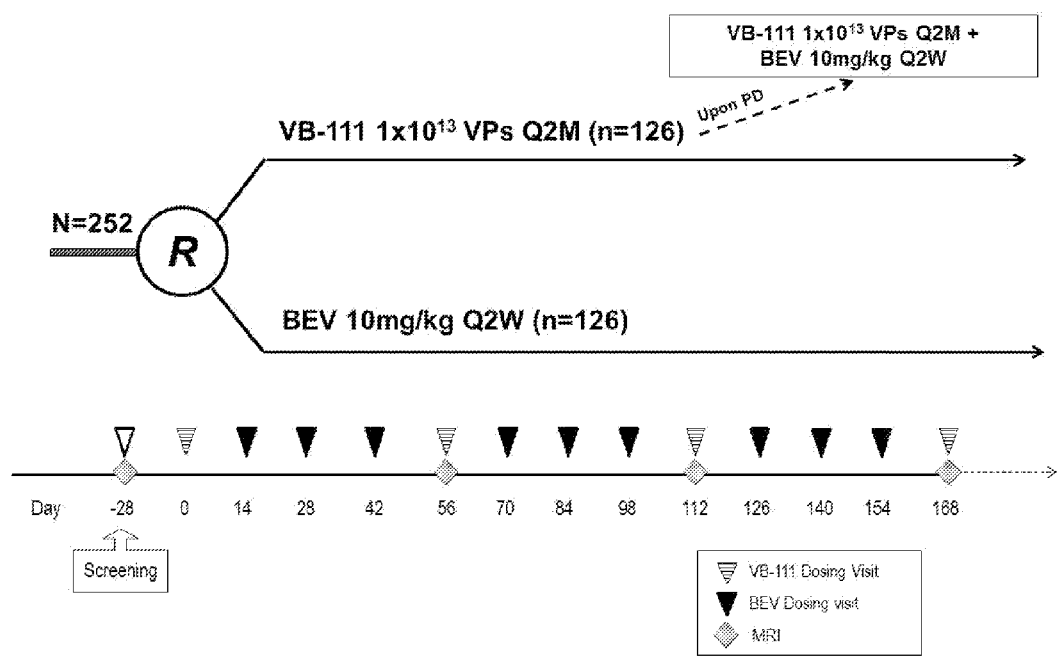
FIG. 1 shows a combination therapy regimen of an adenovirus comprising a FAS-chimera gene operably linked to an endothelial cell-specific promoter (e.g., VB-111) and bevacizumab (BEV). $1 \times 10^{13}$ VPs of VB-111 can be administered every eight weeks, and bevacizumab can be administered every two weeks. MRI assessment can be performed every eight weeks to assess the tumor progression.

Unless defined otherwise, all technical and scientific terms used herein have the same meaning as commonly understood by one of ordinary skill in the art to which this invention belongs. In case of conflict, the present application including the definitions will control. Unless otherwise required by context, singular terms shall include pluralities and plural terms shall include the singular. All publications, patents and other references mentioned herein are incorporated by reference in their entireties for all purposes as if each individual publication or patent application were specifically and individually indicated to be incorporated by reference.

Although methods and materials similar or equivalent to those described herein can be used in practice or testing of the present invention, suitable methods and materials are described below. The materials, methods and examples are illustrative only and are not intended to be limiting. Other features and advantages of the invention will be apparent from the detailed description and from the claims.

In order to further define this invention, the following terms and definitions are provided.

The term "about" is used herein to mean approximately, roughly, around, or in the regions of. When the term "about" is used in conjunction with a numerical range, it modifies that range by extending the boundaries above and below the numerical values set forth. In general, the term "about" is used herein to modify a numerical value above and below the stated value by a variance of 10 percent, up or down (higher or lower).

As used herein, "antibody" means an intact immunoglobulin, an antigen-binding fragment thereof, or an antigen-binding molecule. Antibodies of this invention can be of any isotype or class (e.g., M, D, G, E and A) or any subclass (e.g., G1-4, A1-2) and can have either a kappa (κ) or lambda (λ) light chain.

The term "effective amount" as used herein refers to an amount effective, at dosages and for periods of time necessary, to achieve a desired result. A desired result can be, for example, reduction or inhibition of neo-vascularization or angiogenesis in vitro or in vivo. An effective amount need not be a complete removal of neo-vascularization or angiogenesis.

As used herein, a "therapeutically effective amount" refers to an amount effective, at dosages and for periods of time necessary, to achieve a desired therapeutic result. A desired therapeutic result may be, e.g., lessening of symptoms, regression or stabilization of tumor size in radiological imaging, prolonged survival, improved mobility, and the like. A therapeutic result need not be a "cure." In some embodiments, a therapeutically effective amount is an amount or dosage that is necessary to prevent occurrence of a tumor.

As used herein, a "prophylactically effective amount" refers to an amount effective, at dosages and for periods of time necessary, to achieve the desired prophylactic result. In some embodiments, since a prophylactic dose is used in subjects prior to or at an earlier stage of disease, the prophylactically effective amount will be less than the therapeutically effective amount.

The term "polynucleotide" or "nucleotide" is intended to encompass a singular nucleic acid as well as plural nucleic acids, and refers to an isolated nucleic acid molecule or construct, e.g., messenger RNA (mRNA) or plasmid DNA (pDNA). In certain embodiments, a polynucleotide comprises a conventional phosphodiester bond or a non-conventional bond (e.g., an amide bond, such as found in peptide nucleic acids (PNA)).

As used herein, a "polynucleotide," "nucleotide," or "nucleic acid" can be used interchangeably and contain the nucleotide sequence of the full-length cDNA sequence, including the untranslated 5' and 3' sequences, the coding sequences, as well as fragments, epitopes, domains, and variants of the nucleic acid sequence. The polynucleotide can be composed of any polyribonucleotide or polydeoxyribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the polynucleotides can be composed of triple-stranded regions comprising RNA or DNA or both RNA and DNA. Polynucleotides may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

In the present invention, a polypeptide can be composed of amino acids joined to each other by peptide bonds or modified peptide bonds, i.e., peptide isosteres, and may contain amino acids other than the 20 gene-encoded amino acids (e.g. non-naturally occurring amino acids). The polypeptides of the present invention may be modified by either natural process, such as posttranslational processing, or by chemical modification techniques which are well known in the art. Such modifications are well described in basic texts and in more detailed monographs, as well as in a voluminous research literature. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, Proteins—Structure And Molecular Properties, 2nd Ed., T. E. Creighton, W. H. Freeman and Company, New York (1993); Posttranslational Covalent Modification of Proteins, B. C. Johnson, Ed., Academic Press, New York, pgs. 1-12 (1983); Seifter et al., *Meth Enzymol* 182:626-646 (1990); Rattan et al., *Ann NY Acad Sci* 663:48-62 (1992).)

The terms "fragment," "variant," "derivative" and "analog" when referring to any polypeptide or polynucleotide of the present invention include any polypeptides or polynucleotides which retain at least some activities, i.e., the ability to function as any naturally-occurring function of the polypeptide or polynucleotide. For example, a "fragment," "variant," "derivative" and "analog" of Tumor necrosis factor Receptor 1 (TNFR1) has some activities of the naturally occurring full-length TNFR1, e.g., the ability to bind to TNFR1 ligand, i.e., TNF-alpha or lymphotoxin. In another example, a "fragment," "variant," "derivative" and "analog" of a FAS polypeptide have some activities of a naturally-occurring full-length FAS polypeptide, e.g., the ability to induce apoptosis. In other examples, a "fragment," "variant," "derivative" and "analog" of an endothelial cell-specific promoter can induce endothelial cell-specific expression of a gene operably linked to the promoter. Additional non-limiting examples of the various fragments, variants, analogues, or derivatives of the TNFR1, FAS polypeptide, and endothelial cell-specific promoters are described below.

In the present invention, a "polypeptide fragment" or "protein fragment" refers to a short amino acid sequence of a polypeptide. Protein or polypeptide fragments may be "free-standing," or comprised within a larger polypeptide of which the fragment forms a part of region. Representative examples of polypeptide fragments of the invention, include, for example, fragments comprising about 5 amino acids, about 10 amino acids, about 15 amino acids, about 20 amino acids, about 30 amino acids, about 40 amino acids, about 50 amino acids, about 60 amino acids, about 70 amino acids, about 80 amino acids, about 90 amino acids, or about 100 amino acids.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, if an amino acid in a polypeptide is replaced with another amino acid from the same side chain family, the substitution is considered to be conservative. In another embodiment, a string of amino acids can be conservatively replaced with a structurally similar string that differs in order and/or composition of side chain family members.

The term "percent sequence identity" between two polynucleotide or polypeptide sequences refers to the number of identical matched positions shared by the sequences over a comparison window, taking into account additions or deletions (i.e., gaps) that must be introduced for optimal alignment of the two sequences. A matched position is any position where an identical nucleotide or amino acid is presented in both the target and reference sequence. Gaps presented in the target sequence are not counted since gaps are not nucleotides or amino acids. Likewise, gaps presented in the reference sequence are not counted since target sequence nucleotides or amino acids are counted, not nucleotides or amino acids from the reference sequence.

The percentage of sequence identity is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity. The comparison of sequences and determination of percent sequence identity between two sequences may be accomplished using readily available software both for online use and for download. Suitable software programs are available from various sources, and for alignment of both protein and nucleotide sequences. One suitable program to determine percent sequence identity is bl2seq, part of the BLAST suite of program available from the U.S. government's National Center for Biotechnology Information BLAST web site (blast.ncbi.nlm.nih.gov). Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at www.ebi.ac.uk/Tools/psa.

Different regions within a single polynucleotide or polypeptide target sequence that aligns with a polynucleotide or polypeptide reference sequence can each have their own percent sequence identity. It is noted that the percent sequence identity value is rounded to the nearest tenth. For example, 80.11, 80.12, 80.13, and 80.14 are rounded down to 80.1, while 80.15, 80.16, 80.17, 80.18, and 80.19 are rounded up to 80.2. It also is noted that the length value will always be an integer.

One skilled in the art will appreciate that the generation of a sequence alignment for the calculation of a percent sequence identity is not limited to binary sequence-sequence comparisons exclusively driven by primary sequence data. Sequence alignments can be derived from multiple sequence alignments. One suitable program to generate multiple sequence alignments is ClustalW2, available from www.clustal.org. Another suitable program is MUSCLE, available from www.drive5.com/muscle/. ClustalW2 and MUSCLE are alternatively available, e.g., from the EBI.

It will also be appreciated that sequence alignments can be generated by integrating sequence data with data from heterogeneous sources such as structural data (e.g., crystallographic protein structures), functional data (e.g., location of mutations), or phylogenetic data. A suitable program that integrates heterogeneous data to generate a multiple sequence alignment is T-Coffee, available at www.tcoffee.org, and alternatively available, e.g., from the EBI. It will also be appreciated that the final alignment used to calculated percent sequence identity may be curated either automatically or manually.

As used herein, the terms "linked," "fused," "fusion," "chimeric," and "chimera" are used interchangeably. These terms refer to the joining together of two more elements or components, by whatever means including chemical conjugation or recombinant means. An "in-frame fusion" refers to the joining of two or more open reading frames (ORFs) to form a continuous longer ORF, in a manner that maintains the correct reading frame of the original ORFs. Thus, the resulting recombinant fusion or chimeric protein is a single protein containing two or more segments that correspond to polypeptides encoded by the original ORFs (which segments are not normally so joined in nature.) Although the reading frame is thus made continuous throughout the fused segments, the segments may be physically or spatially separated by, for example, in-frame linker sequence.

The terms "heterologous" and "heterologous moiety" mean that a polynucleotide, polypeptide, or other moiety is derived from a distinct entity from that of the entity to which it is being compared. For instance, a heterologous polypeptide can be synthetic, or derived from a different species, different cell type of an individual, or the same or different type of cell of distinct individuals. In one aspect, a heterologous moiety can be a polypeptide fused to another polypeptide to produce a fusion polypeptide or protein. In another aspect, a heterologous moiety can be a non-polypeptide such as PEG conjugated to a polypeptide or protein.

In the context of polypeptides, a "linear sequence" or a "sequence" is an order of amino acids in a polypeptide in an amino to carboxyl terminal direction in which residues that neighbor each other in the sequence are contiguous in the primary structure of the polypeptide.

The term "expression" as used herein refers to a process by which a gene produces a biochemical, for example, an RNA or polypeptide. The process includes any manifestation of the functional presence of the gene within the cell including, without limitation, gene knockdown as well as both transient expression and stable expression. It includes without limitation transcription of the gene into messenger RNA (mRNA), transfer RNA (tRNA), small hairpin RNA (shRNA), small interfering RNA (siRNA) or any other RNA product and the translation of such mRNA into polypeptide(s). If the final desired product is biochemical, expression includes the creation of that biochemical and any precursors.

The term "complementarity determining region" (CDR) as used herein refers to the amino acid residues of an antibody which are responsible for binding to an antigen. The CDR regions of an antibody are found within the hypervariable region of both heavy and light chains of the antibody. Full length antibodies comprise three CDR regions in the heavy chain variable domain and three CDR regions in the light chain variable domain.

The term "repeatedly administered" as used herein refers to administration of a therapeutic agent on a repeated basis at defined, fixed intervals. The intervals of time between each administration may be altered during the course of the repeated administration and may be as long as 1 day, 2 days, 3 days, 4 days, 5 days, 6 days, 7 days, 2 weeks, 3 weeks, 4 weeks, 5 weeks, 6 weeks, 7 weeks, 2 months, 3 months, 4 months, 5 months, 6 months, 7 months, 8 months, 9 months, 10 months, 11 months, 1 year, or more.

The term "combination therapy" as used herein refers to the administration of two or more therapeutic modalities to treat a disease or condition. In one aspect of the present invention, combination therapy refers to the administration of a VEGF antagonist and a vector to a subject or a subject population in need thereof. In some embodiments, the combination therapy comprises administering the VEGF antagonist prior to administering the vector. In another embodiment, the combination therapy comprises administering the VEGF antagonist concomitantly with administration of the vector. In another embodiment, the combination therapy comprises administering the VEGF antagonist after administering the vector.

II. Nucleic Acid Constructs Comprising a Fas-Chimera Gene and an Endothelial Cell Specific Promoter The present invention is related to methods of inducing or improving responsiveness to a VEGF antagonist in a subject or a subject population comprising administering a vector and a VEGF antagonist. The gene encoding the FAS-chimera protein (or gene product), in the present invention can be linked to an endothelial cell-specific promoter, which directs expression of the FAS-chimera gene product in an endothelial cell. Expression of such a cytotoxic gene product is useful in a situation where excessive neo-vascularization or blood vessel growth is not desirable, e.g., in a tumor.

The present invention also provides a homogeneous population of a nucleic acid construct comprising a FAS-chimera gene operably linked to an endothelial cell-specific promoter.

A. FAS-Chimera

A FAS-chimera protein expressed by the nucleic acid construct of the invention comprises at least two "death receptor" polypeptides, each of the polypeptides is derived from a different protein. The first polypeptide of the FAS-chimera protein comprises a ligand binding domain of Tumor Necrosis Factor Receptor 1 (TNFR1). The second polypeptide of the FAS-chimera protein comprises an effector domain of a FAS polypeptide.

The ligand binding domain of TNFR1 can be any domain that binds to a TNFR1 ligand. In one embodiment, the TNFR1 ligand is TNF-α. In another embodiment, the TNFR1 ligand is lymphotoxin-α. The ligand binding domain of TNFR1 can be an extracellular domain of TNFR1 or any fragments, variants, derivatives, or analogues thereof. Non-limiting examples of the TNFR1 ligand binding domain are described below.

The effector domain of a FAS polypeptide useful for the invention comprises any FAS domains that form death-inducing signaling complex (DISC), thereby inducing apoptosis. In one embodiment, an effector domain of a FAS polypeptide comprises an intracellular domain, a transmembrane domain, or both. Non-limiting examples of FAS polypeptide effector domains are described below.

The TNFR1 and the FAS polypeptide can be linked by a peptide bond or by a linker. The linker connecting the TNFR1 ligand binding domain with the FAS effector domain can be a polypeptide linker or a non-peptide linker. For example, a linker for the FAS-chimera protein can comprise one or more glycine, serine, leucine, or any combinations thereof. In one embodiment, a linker useful for the invention comprises Ser-Leu. In another embodiment, a linker useful for the invention comprises (GGGS)n, (Denise et al. *J. Biol. Chem.* 277:35035-35043 (2002)), wherein n can be 0, 1, 2, 3, 4, 5, 6, 7, 8, 9, or 10 or more (SEQ ID NO: 27).

1. Tumor Necrosis Factor Receptor 1

The full-length human TNFR1 polypeptide is 455 amino acids in length and is also known as TNF-R1, Tumor necrosis factor receptor type I (TNFRI), TNFR-I, TNFRSF1A, TNFAR, p55, P60, or CD120a. Naturally-occurring human TNFR1 polypeptide is known to bind to TNF-α or homotrimeric lymphotoxin-α. Binding of TNF-α to the extracellular domain leads to homotrimerization of TNFR1, which then interacts specifically with the death domain of Tumor Necrosis Factor Receptor Type 1-Associated Death Domain Protein (TRADD). Various TRADD-interacting proteins such as TNF Receptor Associated Factors (TRAFS), Receptor-Interacting Serine/Threonine-Protein Kinase 1 (RIPK1), and Fas-Associated Protein with Death Domain (FADD) are recruited to the complex by their association with TRADD. The complex activates at least two distinct signaling cascades, apoptosis and NF-kappa-B signaling.

A 455 aa polypeptide sequence reported as a human TNFR1 polypeptide sequence has the identifier number P19438-1 in the UniProtKB database. This human TNFR1 polypeptide sequence is designated herein as isoform A and SEQ ID NO: 2. SEQ ID NO: 1 is a nucleotide sequence encoding SEQ ID NO: 2. A polypeptide sequence of 108 aa was reported as an isoform of the human TNFR1 polypeptide sequence and has the identifier number P19438-2 in the UniProtKB database. The 108 aa polypeptide corresponds to amino acids 1 to 108 of isoform A (SEQ ID NO: 2) and is designated herein as isoform B. Another variant of the human TNFR1 polypeptide having 232 aa was reported as the identifier number P19438-3 in the UniProtKB database. The 232 aa polypeptide corresponds to amino acids 1 to 232 of isoform A (SEQ ID NO: 2) and is designated herein as isoform C. Additional natural variants of human TNFR1 include, but are not limited to, the TNFR1 polypeptide of isoforms A, B, and C comprising one or more mutations selected from the group consisting of H51Q, C59R, C59S, C62G, C62Y, P75L, T79M, C81F, C99S, S115G, C117R, C117Y, R121P, R121Q, P305T, and any combinations thereof. Other known TNFR1 variants include the TNFR1 polypeptide of isoforms A, B, and C comprising L13LILPQ, K255E, S286G, R394L, 412:Missing, GPAA443-446APP, or any combinations thereof.

Table 1 shows the human wild-type TNFR1 amino acid sequence and a nucleotide sequence encoding the wild-type TNFR1.

TABLE 1

TNFR1 Sequences

| SEQ ID No. | Sequences |
|---|---|
| Amino acid sequence of TNFR1 (SEQ ID NO: 2) | MGLSTVPDLLLPLVLLELLVGIYPSGVIGLVPHLGDREKRDSVCPQGKYIHPQNNSICCT KCHKGTYLYNDCPGPGQDTDCRECESGSFTASENHLRHCLSCSKCRKEMGQVEISSCTVD RDTVCGCRKNQYRHYWSENLFQCFNCSLCLNGTVHLSCQEKQNTVCTCHAGFFLRENECV SCSNCKKSLECTKLCLPQIENVKGTEDSGTTVLLPLVIFFGLCLLSLLFIGLMYRYQRWK SKLYSIVCGKSTPEKEGELEGTTTKPLAPNPSFSPTPGFTPTLGFSPVPSSTFTSSSTYT PGDCPNFAAPRREVAPPYQGADPILATALASDPIPNPLQKWEDSAHKPQSLDTDDPATLY AVVENVPPLRWKEFVRRLGLSDHEIDRLELQNGRCLREAQYSMLATWRRRTPRREATLEL LGRVLRDMDLLGCLEDIEEALCGPAALPPAPSLLR |
| Nucleotide Sequence encoding TNFR1 (SEQ ID NO: 1) | Atgggcctctccaccgtgcctgacctgctgctgccgctggtgctcctggagctgttggtg Ggaatatacccctcagggggttattggactggtccctcacctaggggacagggagaagaga Gatagtgtgtgtccccaaggaaaatatatccaccctcaaaataattcgatttgctgtacc Aagtgccacaaaggaacctacttgtacaatgactgtccaggcccggggcaggatacggac Tgcagggagtgtgagagcggctccttcaccgcttcagaaaaccacctcagacactgcctc Agctgctccaaatgccgaaaggaaatgggtcaggtggagatctcttcttgcacagtggac Cgggacaccgtgtgtggctgcaggaagaaccagtaccggcattattggagtgaaaacctt Ttccagtgcttcaattgcagcctctgcctcaatgggaccgtgcacctctcctgccaggag Aaacagaacaccgtgtgcacctgccatgcaggtttctttctaagagaaaacgagtgtgtc Tcctgtagtaactgtaagaaaagcctggagtgcacgaagttgtgcctaccccagattgag Aatgttaagggcactgaggactcaggcaccacagtgctgttgcccctggtcatttctctt Ggtctttgccttttatccctcctcttcattggttttaatgtatcgctaccaacggtggaag Tccaagctctactccattgtttgtgggaaatcgacacctgaaaaagagggggagcttgaa Ggaactactactaagcccctggccccaaacccaagcttcagtcccactccaggcttcacc Cccaccctgggcttcagtcccgtgccagttccaccttcacctccagctccacctatacc Cccggtgactgtcccaactttgcggctccccgcagagaggtggcaccaccctatcagggg Gctgaccccatccttgcgacagccctcgcctccgaccccatcccaaccccttcagaag Tgggaggacagcgcccacaagccacagagcctagacactgatgaccccgcgacgctgtac Gccgtggtggagaacgtgcccccgttgcgctgaaggaattcgtgcggcgcctagggctg Agcgaccacgagatcgatcggctggagctgcagaacgggcgctgcctgcgcgaggcgcaa Tacagcatgctggcgacctggaggcggcgcacgccgcggcgcgaggccacgctggagctg Ctgggacgcgtgctccgcgacatggacctgctgggctgcctggaggacatcgaggaggcg ctttgcgggcccgccgccctcccgcccgcgcccagtcttctcaga |
| Amino acid sequence of a Ligand Binding Domain of TNFR1 (SEQ ID NO: 4) | MGLSTVPDLLLPLVLLELLVGIYPSGVIGLVPHLGDREKRDSVCPQGKYIHPQNNSICCT KCHKGTYLYNDCPGPGQDTDCRECESGSFTASENHLRHCLSCSKCRKEMGQVEISSCTVD RDTVCGCRKNQYRHYWSENLFQCFNCSLCLNGTVHLSCQEKQNTVCTCHAGFFLRENECV SCSNCKKSLECTKLCLP |
| Nucleotide sequence encoding a Ligand Binding Domain of TNFR1 (SEQ ID NO: 3) | atgggcctct ccaccgtgcc tgacctgctg ctgccgctgg tgctcctgga gctgttggtg ggaatatacc cctcagggt tattggactg gtccctcacc tagggacag ggagaagaga gatagtgtgt gtccccaagg aaaatatatc caccctcaaa ataattcgat ttgctgtacc aagtgccaca aaggaaccta cttgtacaat gactgtccag gcccggggca ggatacggac tgcagggagt gtgagagcgg ctccttcacc gcttcagaaa accacctcag acactgcctc agctgctcca aatgccgaaa ggaaatgggt caggtggaga tctcttcttg cacagtggac cgggacaccg tgtgtggctg caggaagaac cagtaccggc attattggag tgaaaacctt ttccagtgct tcaattgcag cctctgcctc aatgggaccg tgcacctctc tgccaggag aaacagaaca ccgtgtgcac ctgccatgca ggtttctttc taagagaaaa cgagtgtgtc tcctgtagta actgtaagaa aagcctggag tgcacgaagt tgtgcctacc a |

The mouse TNFR1 polypeptide sequence and its variants are also reported. The 454 aa mouse TNFR1 polypeptide has the identifier number P25118 in UniProtKB database. TNFR1 polypeptides known in other animals include, but are not limited to, rat (e.g., P22934 in the UniProtKB database), cow (e.g., O19131 in the UniProtKB database), pig (e.g., P50555 in the UniProtKB database), or horse (e.g., D1MH71 in the UniProtKB database).

The full-length TNFR1 can be cleaved into two chains, (1) TNF Receptor Superfamily Member 1A, membrane form (i.e., amino acids 22 to 455 corresponding to full-length TNFR1) and (2) TNF-binding protein 1 (TBPI) (i.e., amino acids 41 to 291 corresponding to full-length TNFR1). The full-length human TNFR1 polypeptide consists of a signal sequence (amino acids 1 to 21 of SEQ ID NO: 2), an extracellular domain (amino acids 22 to 211 of SEQ ID NO: 2), a trans-membrane domain (amino acids 212 to 234 of SEQ ID NO: 2), and a cytoplasmic domain (amino acids 235 to 455 of SEQ ID NO: 2). The TNFR1 extracellular domain comprises four cysteine repeat regions, TNFR-Cys1 (amino acids 43 to 82 corresponding to SEQ ID NO: 2), TNFR-Cys2 (amino acids 83 to 125 corresponding to SEQ ID NO: 2), TNFR-Cys3 (amino acids 126 to 166 corresponding to SEQ ID NO: 2), and TNFR-Cys4 (amino acids 167 to 196 corresponding to SEQ ID NO: 2).

As one of skill in the art will appreciate, the beginning and ending residues of the domains listed above can vary depending upon the computer modeling program used or the method used for determining the domain. As such, various functional domains of TNFR1 may vary from those defined above.

In one embodiment, a ligand binding domain of TNFR1 useful for the FAS-chimera protein comprises, consists essentially of, or consists of an extracellular domain of TNFR1, or any fragment, variant, derivative, or analogue thereof, wherein the extracellular domain of TNFR1, or any fragment, variant, derivative, or analogue thereof binds to TNF-α. In another embodiment, a ligand binding domain of TNFR1 comprises TNFR-Cys1; TNFR-Cys2; TNFR-Cys3; TNFR-Cys4; TNFR-Cys1 and TNFR-Cys2; TNFR-Cys1 and TNFR-Cys3; TNFR-Cys1 and TNFR-Cys4; TNFR-Cys2 and TNFR-Cys3; TNFR-Cys2 and TNFR-Cys4; TNFR-Cys3 and TNFR-Cys4; TNFR-Cys1, TNFR-Cys2, and TNFR-Cys3; TNFR-Cys1, TNFR-Cys2, and TNFR-Cys4; TNFR-Cys2, TNFR-Cys3, and TNFR-Cys4; or TNFR-Cys1, TNFR-Cys2, TNFR-Cys3, and TNFR-Cys4. In other embodiments, a ligand binding domain of TNFR1 in the FAS-chimera protein comprises TNF binding protein I. In yet other embodiments, a TNFR1 ligand binding domain of the FAS-chimera protein comprises, consists essentially of, or consists of an amino acid sequence at least 60%, 70%, 80%, 90%, 95%, 96%, 97%, 98%, 99%, or 100% identical to amino acids 22 to 190, amino acids 22 to 191, amino acids 22 to 192, amino acids 22 to 193, amino acids 22 to 194, amino acids 22 to 195, amino acids 22 to 196, amino acids 22 to 197, amino acids 22 to 198, amino acids 22 to 199, amino acids 22 to 200, amino acids 22 to 201, amino acids 22 to 202, amino acids 22 to 203, amino acids 22 to 204, amino acids 22 to 205, amino acids 22 to 206, amino acids 22 to 207, amino acids 22 to 208, amino acids 22 to 209, amino acids 22 to 210, or amino acids 22 to 211 of SEQ ID NO: 2, wherein the ligand binding domain binds to a TNFR1 ligand, e.g., TNF-α.

In other embodiments, the ligand binding domain of TNFR1 further comprises a signal peptide. One example of the suitable signal peptides is the signal peptide of TNFR1, e.g., amino acids 1 to 21 of SEQ ID NO: 2. In yet other embodiments, a ligand binding domain of the FAS-chimera gene product comprises, consists essentially of, or consists of an amino acid sequence at least 60%, 70%, 80%, 90%, 95%, 96%, 97%, 98%, 99%, or 100% identical to amino acids 1 to 190, amino acids 1 to 191, amino acids 1 to 192, amino acids 1 to 193, amino acids 1 to 194, amino acids 1 to 195, amino acids 1 to 196, amino acids 1 to 197, amino acids 1 to 198, amino acids 1 to 199, amino acids 1 to 200, amino acids 1 to 201, amino acids 1 to 202, amino acids 1 to 203, amino acids 1 to 204, amino acids 1 to 205, amino acids 1 to 206, amino acids 1 to 207, amino acids 1 to 208, amino acids 1 to 209, amino acids 1 to 210, or amino acids 1 to 211 of SEQ ID NO: 2, wherein the ligand binding domain binds to a TNFR1 ligand, e.g., TNF-α. In a specific embodiment, a TNFR1 ligand binding domain of the FAS-chimera protein comprises, consists essentially of, or consists of an amino acid sequence at least 60%, 70%, 80%, 90%, 95%, 96%, 97%, 98%, 99%, or 100% identical to SEQ ID NO: 4, wherein the ligand binding domain binds to a TNFR1 ligand, e.g., TNF-α.

In yet other embodiments, the ligand binding domain of TNFR1 is encoded by a nucleotide sequence at least 60%, 70%, 80%, 90%, 95%, 96%, 97%, 98%, 99%, or 100% identical to SEQ ID NO: 3.

In still other embodiments, a TNFR1 ligand binding domain of the FAS-chimera protein comprises, consists essentially of, or consists of an amino acid sequence at least 60%, 70%, 80%, 90%, 95%, 96%, 97%, 98%, 99%, or 100% identical to amino acids 22 to 108 of SEQ ID NO: 2 (TNFR1 isoform B), amino acids 22 to 232 of SEQ ID NO: 2 (TNFR1 isoform C), or amino acids 44 to 291 of SEQ ID NO: 2 (TBP1), wherein the ligand binding domain binds to a TNFR1 ligand, e.g., TNF-α.

2. FAS Polypeptide

The full-length human FAS polypeptide is 335 amino acids in length and is also known as Tumor Necrosis Factor Receptor Superfamily Member 6, Apo-1 antigen, Apoptosis-mediating surface antigen FAS, FASLG receptor, or CD95. Naturally occurring FAS polypeptide is a receptor for TNFSF6/FASLG. When the FAS polypeptide binds to the FAS ligand (FasL), the interaction between FAS and FasL results in the formation of the death-inducing signaling complex (DISC), which contains the FADD, caspase-8 and caspase-10. In some types of cells (type I), processed caspase-8 directly activates other members of the caspase family, and triggers the execution of apoptosis of the cell. In other types of cells (type II), the FAS-DISC starts a feedback loop that spirals into increasing release of proapoptotic factors from mitochondria and the amplified activation of caspase-8. FAS-mediated apoptosis may have a role in the induction of peripheral tolerance, in the antigen-stimulated suicide of mature cells or both.

A 335 aa polypeptide sequence reported as a human FAS polypeptide sequence has the identifier number P25445-1 in the UniProtKB database. This human FAS polypeptide sequence is designated herein as SEQ ID NO: 6. SEQ ID NO: 5 is a nucleotide sequence encoding SEQ ID NO: 6. The nucleotide sequence encoding the FAS polypeptide is also known as APT1, FAS1, or TNFRSF6. The full-length FAS polypeptide contains a signal peptide (amino acids 1 to 25 corresponding to SEQ ID NO: 6), an extracellular domain (amino acids 26 to 173 corresponding to SEQ ID NO: 6), a trans-membrane domain (amino acids 174 to 190 corresponding to SEQ ID NO: 6), and an intracellular (or cytoplasmic) domain (amino acids 191 to 335 corresponding to SEQ ID NO: 6). The intracellular domain contains a death domain (e.g., amino acids 230 to 314 corresponding to SEQ ID NO: 6).

As one of skill in the art will appreciate, the beginning and ending residues of the domains listed above may vary depending upon the computer modeling program used or the method used for determining the domain. As such, various functional domains of FAS may vary from those defined above. Table 2 shows the wild-type human FAS amino acid sequence and a nucleotide sequence encoding the FAS protein.

TABLE 2

FAS Sequences

| | Sequences |
|---|---|
| Amino acid sequence of human FAS protein (SEQ ID NO: 6) | MLGIWTLLPLVLTSVARLSSKSVNAQVTDINSKGLELRKTVTTVETQNLEGLHHDGQFCH KPCPPGERKARDCTVNGDEPDCVPCQEGKEYTDKAHFSSKCRRCRLCDEGHGLEVEINCT RTQNTKCRCKPNFFCNSTVCEHCDPCTKCEHGIIKECTLTSNTKCKEEGSRSNLGWLCLL LLPIPLIVWVKRKEVQKTCRKHRKENQGSHESPTLNPETVAINLSDVDLSKYITTIAGVM TLSQVKGFVRKNGVNEAKIDEIKNDNVQDTAEQKVQLLRNWHQLHGKKEAYDTLIKDLKK ANLCTLAEKIQTIILKDITSDSENSNFRNEIQSLV |
| Nucleotide sequence encoding human FAS sequence (SEQ ID NO: 5) | Atgctgggcatctggaccctcctacctctggttcttacgtctgttgctagattatcgtcc Aaaagtgttaatgcccaagtgactgacatcaactccaagggattggaattgaggaagact Gttactacagttgagactcagaacttggaaggcctgcatcatgatggccaattctgccat Aagccctgtcctccaggtgaaaggaaagctagggactgcacagtcaatggggatgaacca Gactgcgtgccctgccaagaagggaaggagtacacagacaaagcccattttcttccaaa Tgcagaagatgtagattgtgtgatgaaggacatggcttagaagtggaaataaactgcacc Cggacccagaataccaagtgcagatgtaaaccaaacttttttgtaactctactgtatgt Gaacactgtgacccttgcaccaaatgtgaacatggaatcatcaaggaatgcacactcacc Agcaacaccaagtgcaaagaggaaggatccagatctaacttggggtggctttgtcttctt Cttttgccaattccactaattgtttgggtgaagagaaaggaagtacagaaaacatgcaga Aagcacagaaaggaaaaccaaggttctcatgaatctccaacctttaaatcctgaaacagtg Gcaataaatttatctgatgttgacttgagtaaatatatcaccactattgctggagtcatg Acactaagtcaagttaaaggctttgttcgaaagaatggtgtcaatgaagccaaaatagat Gagatcaagaatgacaatgtccaagacacagcagaacagaaagttcaactgcttcgtaat Tggcatcaacttcatggaaagaaagaagcgtatgacacattgattaaagatctcaaaaaa Gccaatctttgtactcttgcagagaaaattcagactatcatcctcaaggacattactagt Gactcagaaaattcaaacttcagaaatgaaatccaaagcttggtctag |
| Amino acid sequence of an Effector Domain of FAS (SEQ ID NO: 8) | GSRSNLGWLCLLLLPIPLIVWVKRKEVQKTCRKHRKENQGS HESPTLNPETVAINLSDVDLSKYITTIAGVMTLSQVKGFVR KNGVNEAKIDEIKNDNVQDTAEQKVQLLRNWHQLHGKKEAY DTLIKDLKKANLCTLAEKIQTIILKDITSDSENSNFRNEIQ SLV |
| Nucleotide sequence encoding an Effector Domain of FAS (SEQ ID NO: 7) | Aggatccagatctaacttggggtggctttgtcttcttcttttgccaattccactaatt Gtttgggtgaagagaaaggaagtacagaaaacatgcagaaagcacagaaaggaaaacc Aaggttctcatgaatctccaaccttaaatcctgaaacagtggcaataaatttatctga Tgttgacttgagtaaatatatcaccactattgctggagtcatgacactaagtcaagtt Aaaggctttgttcgaaagaatggtgtcaatgaagccaaaatagatgagatcaagaatg Acaatgtccaagacacagcagaacagaaagttcaactgcttcgtaattggcatcaact Tcatggaaagaaagaagcgtatgacacattgattaaagatctcaaaaaagccaatctt Tgtactcttgcagagaaaattcagactatcatcctcaaggacattactagtgactcag aaaattcaaacttcagaaatgaaatccaaagcttggtctag |

The mouse FAS polypeptide sequence and its variants are also reported. The 327 aa mouse FAS polypeptide has the identifier number P25446 in UniProtKB database. FAS polypeptides known in other animals include, but are not limited to, Old World monkey (e.g., Q9BDN4 in the UniProtKB database), Rhesus monkey (e.g., Q9BDP2 in the UniProtKB database), rat (e.g., Q63199 in the UniProtKB database), or cow (e.g., P51867 in the UniProtKB database).

Based on the sequence variation in the FAS polypeptide, a person of ordinary skill in the art can identify sequence variations in the effector domain of the FAS polypeptide. For example, natural variants of the FAS effector domains can include one or more substitutions or mutations of C178R, L180F, P183L, I184V, T198I, Y232C, T241K, T241P, V249L, R250P, R250Q, G253D, G253S, N255D, A257D, I259R, D260G, D260V, D260Y, I262S, N264K, T270I, T270K, E272G, E272K, L278F, K299N, T305I, I310S, or any combinations thereof.

In one embodiment, an effector domain of the FAS polypeptide useful for the invention comprises a death domain of the FAS polypeptide. In another embodiment, an effector domain of the FAS polypeptide comprises, consists essentially of, or consists of an amino acid sequence at least 60%, 70%, 80%, 90%, 95%, 96%, 97%, 98%, 99%, or 100% identical to amino acids 230 to 314 of SEQ ID NO: 6. In other embodiments, an effector domain of the FAS polypeptide comprises an intracellular domain of the FAS polypeptide. In yet other embodiments, an effector domain of the FAS polypeptide comprises an amino acid sequence at least 60%, 70%, 80%, 90%, 95%, 96%, 97%, 98%, 99%, or 100% identical to amino acids 185 to 335, amino acids 186 to 335, amino acids 187 to 335, amino acids 188 to 335, amino acids 189 to 335, amino acids 190 to 335, amino acids 191 to 335, amino acids 192 to 335, amino acids 193 to 335, amino acids 194 to 335, amino acids 195 to 335, amino acids 196 to 335, amino acids 197 to 335, amino acids 198 to 335, or amino acids 199 to 335 of SEQ ID NO: 6.

In still other embodiments, the effector domain of the FAS polypeptide further comprises a trans-membrane domain of the FAS polypeptide. In yet other embodiments, an effector domain of the FAS polypeptide comprises an amino acid sequence at least about 60%, 70%, 80%, 90%, 95%, 96%, 97%, 98%, 99%, or 100% identical to amino acids 174 to 335 of SEQ ID NO: 6. In some embodiments, an effector domain of the FAS polypeptide further comprises about ten, about nine, about eight, about seven, about six, about five, about four, about three, about two, or about one amino acid from the C-terminal portion of the FAS extracellular domain. In certain embodiments, an effector domain of the FAS polypeptide comprises an amino acid sequence at least 60%, 70%, 80%, 90%, 95%, 96%, 97%, 98%, 99%, or 100% identical to amino acids 179 to 335, amino acids 178 to 335, amino acids 177 to 335, amino acids 176 to 335, amino acids 175 to 335, amino acids 174 to 335, amino acids 173 to 335, amino acids 172 to 335, amino acids 171 to 335, amino acids 170 to 335, amino acids 169 to 335, amino acids 168 to 335, amino acids 167 to 335, amino acids 166 to 335, amino acids 165 to 335, amino acids 164 to 335, or amino acids 163 to 335 of SEQ ID NO: 6, wherein the effector domain forms a death-inducing signaling complex (DISC), activates caspase 8, or induces apoptosis.

In some embodiments, an effector domain of the FAS polypeptide comprises, consists essentially of, or consists of an amino acid sequence at least 70%, 80%, 90%, 95%, 96%, 97%, 98%, 99%, or 100% identical to SEQ ID NO: 8, wherein the effector domain forms a death-inducing signaling complex (DISC), activates caspase 8, or induces apoptosis.

In other embodiments, an effector domain of the FAS polypeptide is encoded by a nucleotide sequence at least 60%, 70%, 80%, 90%, 95%, 96%, 97%, 98%, 99%, or 100% identical to SEQ ID NO: 7.

In one embodiment, the FAS-chimera gene product for the invention comprises, consists essentially of, or consists of an amino acid sequence at least 70%, 80%, 90%, 95%, 96%, 97%, 98%, 99%, or 100% identical to SEQ ID NO: 10, wherein the FAS-chimera gene product induces apoptosis. In another embodiment, the FAS-chimera gene product is encoded by a nucleotide sequence at least 60%, 70%, 80%, 90%, 95%, 96%, 97%, 98%, 99%, or 100% identical to SEQ ID NO: 9, wherein the FAS-chimera gene product induces apoptosis.

B. Endothelial Cell-Specific Promoter

The nucleic acid construct comprising a FAS-chimera gene further comprises one or more expression control elements useful for regulating the expression of an operably linked FAS-chimera gene. The expression control elements include, but are not limited to, promoters, secretion signals, and other regulatory elements.

The nucleic acid construct useful for the present invention utilizes an endothelial cell-specific promoter to direct expression of the FAS-chimera protein in an endothelial cell, thereby inducing apoptosis of the endothelial cell.

For the purpose of the present invention, an endothelial cell-specific promoter can contain one or more cis-regulatory elements, which improve the endothelial cell-specificity of the promoters compared to the promoter without the cis-regulatory elements. In one example, the cis-regulatory element comprises an enhancer. In another aspect, the cis-regulatory element comprises a hypoxia response element. In other examples, the cis-regulatory element comprises both an enhancer and a hypoxia response element.

In one embodiment, a cis-regulatory element useful for the invention comprises a nucleotide sequence at least 60%, 70%, 80%, 90%, 95%, 96%, 97%, 98%, 99%, or 100% identical to SEQ ID NO: 11 or SEQ ID NO: 12 (the complementary sequence of SEQ ID NO: 11), wherein the cis-regulatory element improves endothelial cell specificity of a promoter compared to a promoter without the cis-regulatory element. The cis-regulatory element can further comprise an additional nucleotide sequence at least 60%, 70%, 80%, 90%, 95%, 96%, 97%, 98%, 99%, or 100% identical to SEQ ID NO: 13 or SEQ ID NO: 14 (the complementary sequence of SEQ ID NO: 13).

In another embodiment, a cis-regulatory element for the invention comprises a nucleotide sequence at least 60%, 70%, 80%, 90%, 95%, 96%, 97%, 98%, 99%, or 100% identical to SEQ ID NO: 13 or SEQ ID NO: 14 (the complementary sequence of SEQ ID NO: 13), wherein the cis-regulatory element improves endothelial cell specificity of a promoter compared to a promoter without the cis-regulatory element. The cis-regulatory element can further comprise an additional nucleotide sequence at least 60%, 70%, 80%, 90%, 95%, 96%, 97%, 98%, 99%, or 100% identical to SEQ ID NO: 11 or SEQ ID NO: 12 (the complementary sequence of SEQ ID NO: 11).

In other embodiments, a cis-regulatory element for the invention comprises a nucleotide sequence at least 60%, 70%, 80%, 90%, 95%, 96%, 97%, 98%, 99%, or 100% identical to SEQ ID NO: 15 or SEQ ID NO: 16 (the complementary sequence of SEQ ID NO: 15), wherein the cis-regulatory element improves endothelial cell specificity of a promoter compared to a promoter without the cis-regulatory element. In yet other embodiments, a cis-regulatory element for the nucleic acid construct comprises SEQ ID NO: 7 or any fragments, variants, derivatives, or analogs thereof, wherein the fragments, variants, derivatives, or analogs improve endothelial cell specificity of a promoter compared to a promoter without the cis-regulatory element.

In some embodiments, a cis-regulatory element for the invention comprises a nucleotide sequence at least 60%, 70%, 80%, 90%, 95%, 96%, 97%, 98%, 99%, or 100% identical to SEQ ID NO: 22 or SEQ ID NO: 23, wherein the cis-regulatory element improves endothelial cell specificity of a promoter compared to a promoter without the cis-regulatory element. In yet other embodiments, a cis-regulatory element for the nucleic acid construct comprises SEQ ID NO: 22 or SEQ ID NO: 23 or any fragments, variants, derivatives, or analogs thereof, wherein the fragments, variants, derivatives, or analogs improve endothelial cell specificity of a promoter compared to a promoter without the cis-regulatory element.

In other embodiments, a cis-regulatory element for the invention comprises a nucleotide sequence at least 60%, 70%, 80%, 90%, 95%, 96%, 97%, 98%, 99%, or 100% identical to SEQ ID NO: 24 or SEQ ID NO: 25, wherein the cis-regulatory element improves endothelial cell specificity of a promoter compared to a promoter without the cis-regulatory element. In yet other embodiments, a cis-regulatory element for the nucleic acid construct comprises SEQ ID NO: 24 or SEQ ID NO: 25 or any fragments, variants, derivatives, or analogs thereof, wherein the fragments, variants, derivatives, or analogs improve endothelial cell specificity of a promoter compared to a promoter without the cis-regulatory element.

Table 3 shows various cis-regulatory element sequences useful for the invention.

TABLE 3

Endothelial Cell-Specific Cis-regulatory Elements and Promoters

| SEQ ID NOs | Sequences |
|---|---|
| SEQ ID NO: 11 | ctggagggtg actttgcttc tggagccagt acttcatact tttcatt |
| SEQ ID NO: 12 | aatgaaaagt atgaagtact ggctccagaa gcaaagtcac cctccag |
| SEQ ID NO: 13 | gtacttcata cttttcattc caatggggtg actttgcttc tgga |
| SEQ ID NO: 14 | tccagaagca aagtcacccc attggaatga aagtatgaa gtac |
| SEQ ID NO: 15 | 3X element<br>ctccagaagcaaagtcacccattggaatgaaaagtatgaagtacaatgaaaagtatgaagt<br>actggctccagaagcaaagtcaccctccagaagcaaagtcacccattggaatgaaaagtat<br>gaagtac |
| SEQ ID NO: 16 | 3x element (Complementary Sequence of SEQ ID NO: 15)<br>gtacttcatactttcattccaatggggtgactttgcttctggagggtgactttgcttctgg<br>agccagtacttcatactttcattgtacttcatactttcattccaatggggtgactttgct<br>tctggag |
| SEQ ID NO: 17 | PPE-1 Promoter<br>gtacgtgtacttctgatcggcgatactagggagataaggatgtgcctgacaaaaccacattg<br>ttgttgttatcattattatttagttttccttccttgctaactcctgacggaatctttctcac<br>ctcaaatgcgaagtactttagtttagaaaagacttggtggaaggggtggtggtggaaaagta<br>gggtgatcttccaaactaatctggttccccgcccgccccagtagctgggattcaagagcgaa<br>gagtggggatcgtccccttgtttgatcagaaagacataaaaggaaaatcaagtgaacaatga<br>tcagcccacctccaccccaccccctgcgcgcgcacaatacaatctatttaattgtacttc<br>atacttttcattccaatggggtgactttgcttctggagaaactcttgattcttgaactctgg<br>ggctggcagctagcaaaaggggaagcgggctgctgctctctgcaggttctgcagcggtctct<br>gtctagtgggtgttttcttttcttagccctgcccctggattgtcagacggcgggcgtctgc<br>ctctgaagttagccgtgatttcctctagagccgggtcttatctctggctgcacgttgcctgt<br>gggtgactaatcacacaataacattgtttagggctggaatgaagtcagagctgtttacccc<br>actctataggggttcaatataaaaaggcggcggagaactgtccgagtcagaagcgttcctgc<br>accggcgctgagagcctgacccggtctgctccgctgtccttgcgcgctgcctcccggctgcc<br>cgcgacgctttcgccccagtggaagggccacttgctgcggccgc |
| SEQ ID NO: 18 | PPE-1-3X promoter<br>gtacgtgtacttctgatcggcgatactagggagataaggatgtgcctgacaaaaccacattg<br>ttgttgttatcattattatttagttttccttccttgctaactcctgacggaatctttctcac<br>ctcaaatgcgaagtactttagtttagaaaagacttggtggaaggggtggtggtggaaaagta<br>gggtgatcttccaaactaatctggttccccgcccgccccagtagctgggattcaagagcgaa<br>gagtggggatcgtccccttgtttgatcagaaagacataaaaggaaaatcaagtgaacaatga<br>tcagcccacctccaccccaccccctgcgcgcgcacaatacaatctatttaattgtacttc<br>atacttttcattccaatggggtgactttgcttctggagaaactcttgattcttgaactctgg<br>ggctggcagctagcctccagaagcaaagtcaccccattggaatgaaaagtatgaagtacaat<br>gaaaagtatgaagtactggctccagaagcaaagtcaccctccagaagcaaagtcacccatt<br>ggaatgaaaagtatgaagtacgctagcaaaaggggaagcgggctgctgctctctgcaggttc<br>tgcagcggtctctgtctagtgggtgttttcttttcttagccctgcccctggattgtcagac<br>ggcgggcgtctgcctctgaagttagccgtgatttcctctagagccgggtcttatctctggct<br>gcacgttgcctgtgggtgactaatcacacaataacattgtttagggctggaatgaagtcaga<br>gctgtttaccccactctataggggttcaatataaaaaggcggcggagaactgtccgagtca<br>gaagcgttcctgcaccggcgctgagagcctgacccggtctgctccgctgtccttgcgcgctg<br>cctcccggctgcccgcgacgctttcgccccagtggaagggccacttgctgcggccgc |
| SEQ ID NO: 22 | ggtgactttg cttctggag |
| SEQ ID NO: 23 | ctccagaagcaaagtcacc |
| SEQ ID NO: 24 | gtacttcata cttttcatt |
| SEQ ID NO: 25 | aatgaaaagtatgaagtac |
| SEQ ID NO: 26 | Hypoxia Response element<br>gcacgt |

A cis-regulatory element for the present invention can be linked to a promoter upstream or downstream of the promoter or inserted between the two nucleotides in the promoter. The endothelial cell-specific promoter for the present invention can utilize any promoters known in the art. For example, suitable promoters which can be utilized for the present invention include the endothelial-specific promoters: preproendothelin-1 (PPE-1 promoter), US 2010/0282634, published Nov. 11, 2010; and WO 2011/083464, published Jul. 14, 2011); the PPE-1-3X promoter (U.S. Pat. Nos. 7,579,327, 8,071,740, 8,039,261, US2010/0282634, US 2007/0286845, WO 2011/083464, and WO2011/083466); the TIE-1 (S79347, S79346) and the TIE-2 (U53603) promoters [Sato T N, Proc Natl Acad Sci USA 1993 Oct. 15; 90(20):9355-8], the Endoglin promoter [Y11653; Rius C, Blood 1998 Dec. 15; 92(12):4677-90], the von Willerbrand factor [AF152417; Collins C J Proc Natl Acad Sci USA 1987 July; 84(13):4393-7], the KDR/flk-1 promoter [X89777, X89776; Ronicke V, Circ Res 1996 August; 79(2):277-85], The FLT-1 promoter [D64016 AJ224863; Morishita K, J Biol Chem 1995 Nov. 17; 270(46):27948-53], the Egr-1 promoter [AJ245926; Sukhatme V P, Oncogene Res 1987 September-October; 1(4):343-55], the E-selectin promoter [Y12462; Collins T J Biol Chem 1991 Feb. 5; 266(4):2466-73], The endothelial adhesion molecules promoters: ICAM-1 [X84737; Horley K J EMBO J 1989 October; 8(10):2889-96], VCAM-1 [M92431; Iademarco M F, J Biol Chem 1992 Aug. 15; 267(23): 16323-9], PECAM-1 [AJ313330 X96849; CD31, Newman P J, Science 1990 Mar. 9; 247(4947): 1219-22], the vascular smooth-muscle-specific elements: CArG box X53154 and aortic carboxypeptidase-like protein (ACLP) promoter [AF332596; Layne M D, Circ Res. 2002; 90: 728-736] and Aortic Preferentially Expressed Gene-1 [Yen-Hsu Chen J. Biol. Chem, Vol. 276, Issue 50, 47658-47663, Dec. 14, 2001], all of which are incorporated herein by reference in their entireties.

In one embodiment, a promoter linked to the endothelial cell-specific element comprises a nucleotide sequence at least 60%, 70%, 80%, 90%, 95%, 96%, 97%, 98%, 99%, or 100% of SEQ ID NO: 17, wherein the promoter linked to the element induces endothelial cell-specificity to the gene operably linked to the promoter. In another embodiment, a promoter linked to the endothelial cell-specific element comprises a fragment, a variant, a derivative, or an analog of a wild-type PPE-1 promoter, wherein said fragment, variant, derivative, or analog thereof induces endothelial cell-specificity to the gene operably linked to the promoter. In one example, the endothelial cell-specific element can be inserted between nucleotide residues 442 and 449 corresponding to SEQ ID NO: 17.

In further embodiments, an endothelial cell-specific promoter comprises a hypoxia responsive element. A hypoxia responsive element (HRE) is located on the antisense strand of the endothelin-1 promoter. This element is a hypoxia-inducible factor-1 binding site that is required for positive regulation of the endothelin-1 promoter (of the human, rat and murine gene) by hypoxia. Hypoxia is a potent signal, inducing the expression of several genes including erythropoietin (Epo), VEGF, and various glycolytic enzymes. The core sequence (8 base pairs) is conserved in all genes that respond to hypoxic conditions and the flanking regions are different from other genes. The ET-I hypoxia responsive element is located between the GAT A-2 and the AP-1 binding sites. In one example, a hypoxia response element comprises SEQ ID NO: 26, a fragment, a variant, a derivative, or an analog thereof.

In other embodiments, an endothelial cell-specific promoter useful for the invention comprises, consists essentially of, or consists of a nucleotide sequence at least 60%, 70%, 80%, 90%, 95%, 96%, 97%, 98%, 99%, or 100% of SEQ ID NO: 18, wherein the promoter linked to the cis-regulatory element induces endothelial cell-specificity to the gene operably linked to the promoter. In another embodiment, an endothelial cell-specific promoter comprises a fragment, a variant, a derivative, or an analog of SEQ ID NO: 18, wherein said fragment, variant, derivative, or analog thereof induces endothelial cell-specificity to the gene operably linked to the promoter.

Additional variations of the endothelial cell-specific promoters can be found at WO2011/083464, WO2011/083466, and WO2012/052423, which are incorporated herein by reference in their entireties.

The present invention also provides a novel promoter sequence comprising a nucleotide sequence SEQ ID NO: 17. In one example, the promoter further comprises an endothelial cell-specific cis-regulatory element. In one example, the endothelian cell-specific cis-regulatory element comprises SEQ ID NO: 11, SEQ ID NO: 12, SEQ ID NO: 13, SEQ ID NO: 14, SEQ ID NO: 15, SEQ ID NO: 16, SEQ ID NO: 22, SEQ ID NO: 23, SEQ ID NO: 24, SEQ ID NO: 25, SEQ ID NO: 26 or any fragments, derivatives, variants, or analogs thereof, wherein the fragments, derivatives, variants, or analogs thereof improve endothelial cell-specificity of the promoter compared to a promoter without the cis-regulatory element. In another example, the promoter comprises a nucleotide sequence of SEQ ID NO: 18. The invention includes a nucleic acid construct comprising the novel promoter and a heterologous nucleotide sequence. In one embodiment, the heterologous nucleic acid sequence comprises a nucleotide sequence encoding a FAS-chimera protein described herein. In another embodiment, the heterologous nucleotide sequence comprises an adenovirus sequence.

C. Vector

The invention also provides a vector comprising the nucleic acid construct, which comprises a FAS-chimera gene operably linked to an endothelial cell-specific promoter. For the purposes of this invention, numerous vector systems may be employed. For example, various viral gene delivery systems that can be used in the practice of this aspect of the invention include, but are not limited to, an adenoviral vector, an alphavirus vector, an enterovirus vector, a pestivirus vector, a lentiviral vector, a baculoviral vector, a herpesvirus vector, an Epstein Barr viral vector, a papovaviral vector, a poxvirus vector, a vaccinia viral vector, an adeno-associated viral vector and a herpes simplex viral vector.

In another embodiment, a vector comprising a FAS-chimera gene operably linked to an endothelial cell-specific promoter is an adenovirus. For example, the adenovirus can be any one or more of human adenovirus species A (serotypes 12, 18, and 31), B (serotpyes 3, 7, 11, 14, 16, 21, 34, 35, 50, and 55), C (serotypes 1, 2, 5, 6, and 57), D (8, 9, 10, 13, 15, 17, 19, 20, 22-30, 32, 33, 36-39, 42-49, 51, 53, 54, and 56), E (serotype 4), F (serotype 40 and 41), or G (serotype 52). In a particular embodiment, the adenovirus for the invention is human adenovirus serotype 5. In some embodiments, the adenovirus useful for gene therapy is a recombinant non-replicating adenovirus, which does not contain an E1 region and an E3 region. In certain embodiments, the adenovirus for the invention is a conditionally replicating adenovirus, which does not contain an E3 region, but contains an E1 region.

In one embodiment, the vector comprises, consists essentially of, or consists of SEQ ID NO: 19. In another embodiment, the adenovirus vector is an isolated virus having European Collection of Cell Cultures (ECACC) Accession Number 13021201.

D. Biological Deposits

Biological deposits were made with the European Collection of Cell Cultures (ECACC) located at Health Protection Agency Culture Collections, Health Protection Agency, Microbiology Services, Porton Down, Salisbury, SP4 0JG, UK, pursuant to the Budapest Treaty and pursuant to 37 C.F.R. § 1.808. Samples of the deposited materials will become available to the public upon grant of a patent. The invention described and claimed herein is not to be limited by the scope of the strain deposited, since the deposited embodiment is intended only as an illustration of the invention.

| Strain | ECACC Accession No. | Date Deposited |
|---|---|---|
| VB-111 | 13021201 | Feb. 12, 2013 |

III. VEGF Antagonists

VEGF, vascular endothelial growth factor, is an endothelial cell-specific mitogen and an inducer of angiogenesis. The term VEGF encompasses the members of the VEGF gene family: VEGF-A, VEGF-B, VEGF-C, and VEGF-D. VEGF-A is considered the prototype member of the VEGF gene family. Through alternative exon splicing, VEGF-A exists in four different isoforms: $VEGF_{121}$, $VEGF_{165}$, $VEGF_{189}$, and $VEGF_{206}$. The four VEGF-A isoforms are 121, 165, 189, and 206 amino acids in length (respectively) after signal sequence cleavage.

Once expressed, VEGF is secreted extracellularly where it binds to the extracellular region of a VEGF receptor (VEGFR). There are two primary VEGFRs, VEGFR-1 or VEGFR-2, both of which are receptor tyrosine kinases. A third VEGFR, VEGFR-3, is a related receptor tyrosine kinase that only binds VEGF-C and VEGF-D. Upon binding to VEGF, the VEGFRs signal downstream events that lead to endothelial cell proliferation and angiogenesis. VEGF-C and VEGF-D are known to regulate lymphatic angiogenesis.

The VEGF gene contains nucleotide sequences that are highly homologous to those of hypoxia-inducible factor-1 (HIF-1). These HIF-1 like sequences enable induction of VEGF gene expression under hypoxic conditions. Thus, under low oxygen conditions, such as within a tumor microenvironment, VEGF gene expression is induced. The production of high levels of VEGF within a tumor bed results in increased VEGFR signaling and thus endothelial cell growth and angiogenesis. The formation of new blood vessels within the tumor provides blood and oxygen to the growing tumor.

Due to the prominent role of VEGF in angiogenesis and tumor growth and development, VEGF antagonists are studied as potential cancer therapeutic agents. VEGF antagonists can prevent VEGF activity by binding directly to VEGF and blocking its interaction with a VEGFR. This reduces signaling from the VEGFR and downstream events, thereby causing a reduction in angiogenesis. In one embodiment, a VEGF antagonist useful for the invention is an anti-VEGF antibody or a VEGF binding molecule. In another embodiment, an anti-VEGF antibody or VEGF-binding molecule is a monoclonal antibody, a humanized antibody, a human antibody, a single chain antibody, or a chimeric antibody. In another embodiment, an anti-VEGF antibody or VEGF-binding molecule for the therapy comprises Fab, $F(ab)_2$, Fv, or scFv.

Another type of VEGF antagonist that can reduce or inhibit VEGF activity is a molecule binding to a VEGFR and thus blocking VEGFR interaction with VEGF. This interference of receptor/ligand binding prevents VEGFR signaling and reduces angiogenesis and endothelial cell proliferation. In one embodiment, the VEGF antagonist is an anti-VEGFR antibody or VEGFR-binding molecule. In another embodiment, the anti-VEGFR antibody or VEGFR-binding molecule is a monoclonal antibody, a humanized antibody, a human antibody, a single chain antibody, or a chimeric antibody. In another embodiment, the anti-VEGFR antibody or VEGFR-binding molecule comprises Fab, $F(ab)_2$, Fv, or scFv.

VEGF antagonists that bind to VEGF or VEGFR can inhibit VEGF activity by similar mechanisms of action in that they prevent receptor/ligand interaction, VEGFR signaling, and downstream signaling events such as endothelial cell proliferation and angiogenesis. Thus, in one embodiment, the VEGF antagonist is selected from the group consisting of bevacizumab (U.S. Pat. No. 7,169,901, incorporated herein by reference in its entirety), ranibizumab (U.S. Pat. No. 7,297,334, incorporated herein by reference in its entirety), VGX-100 (U.S. Pat. No. 7,423,125, incorporated herein by reference in its entirety), r84 (U.S. Pat. No. 8,034,905, incorporated herein by reference in its entirety), aflibercept (U.S. Pat. No. 5,952,199, incorporated herein by reference in its entirety), IMC-18F1 (U.S. Pat. No. 7,972,596, incorporated herein by reference in its entirety), IMC-1C11 (PCT/US2000/02180, incorporated herein by reference in its entirety), and ramucirumab (U.S. Pat. No. 7,498,414, incorporated herein by reference in its entirety). A VEGF binding molecule includes other forms of antibody derived molecules, e.g., a monobody, diabody, minibody, or any chimeric proteins comprising at least one CDR of a VEGF binding antibody, e.g., bevacizumab.

In one embodiment, the anti-VEGF antibody or VEGF binding molecule comprises at least one CDR selected from the group consisting of $V_H$ CDR1 (SEQ ID NO: 28), $V_H$ CDR2 (SEQ ID NO: 29), $V_H$ CDR3 (SEQ ID NO: 30), $V_L$ CDR1 (SEQ ID NO: 31), $V_L$ CDR2 (SEQ ID NO: 32), $V_L$ CDR3 (SEQ ID NO: 33), and any combination thereof. See Table 4.

TABLE 4

Amino Acid Sequences of Complementarity Determining Regions

| CDR | Sequence |
|---|---|
| $V_H$ CDR1 (SEQ ID NO: 28) | GYTFTNYGMN |
| $V_H$ CDR2 (SEQ ID NO: 29) | WINTYTGEPTYAADFKR |
| $V_H$ CDR3 (SEQ ID NO: 30) | YPHYYGSSHWYFDV |
| $V_L$ CDR1 (SEQ ID NO: 31) | SASQDISNYLN |
| $V_L$ CDR2 (SEQ ID NO: 32) | FTSSLHS |
| $V_L$ CDR3 (SEQ ID NO: 33) | QQYSTVPWT |

In another embodiment, the anti-VEGF antibody or the VEGF binding molecule comprises CDR1 (SEQ ID NO: 28), CDR2 (SEQ ID NO: 29), or CDR3 (SEQ ID NO: 30) of the heavy chain variable region ($V_H$) of bevacizumab. For example, an anti-VEGF antibody or VEGF binding molecule comprises CDR1 and CRD2 of $V_H$, CDR1 and CDR3 of $V_H$, CDR2 and CDR3 of $V_H$, or CDR1, CDR2, or CDR3 of $V_H$. In other embodiments, the anti-VEGF antibody or the VEGF binding molecule comprises CDR1 (SEQ ID NO: 31), CDR2 (SEQ ID NO: 32), or CDR3 (SEQ ID NO: 33) of the light chain variable region ($V_L$) of bevacizumab. For example, an anti-VEGF antibody or VEGF-binding molecule comprises CDR1 and CDR2 of $V_L$, CDR1 and CDR3 of $V_L$, CDR2 and CDR3 of $V_L$, or CDR1, CDR2, and CDR3 of $V_L$. In some embodiments, an anti-VEGF antibody or VEGF binding molecule comprises $V_H$ of bevacizumab. In certain embodiments, an anti-VEGF antibody or VEGF binding molecule comprises $V_L$ of bevacizumab.

In another aspect of the present invention, the anti-VEGF antibody or VEGF binding molecule comprises $V_H$ CDR1 (SEQ ID NO: 28), $V_H$ CDR2 (SEQ ID NO: 29), $V_H$ CDR3 (SEQ ID NO: 30), $V_L$ CDR1 (SEQ ID NO: 31), $V_L$ CDR2 (SEQ ID NO: 32), and $V_L$ CDR3 (SEQ ID NO: 33).

IV. Treatment Methods Using Adenovirus Expressing Fas-Chimera Protein and a VEGF Antagonist One embodiment of the present invention provides methods of inducing or improving responsiveness to a VEGF antagonist in a subject or a subject population in need thereof comprising administering a vector expressing a FAS chimera protein in combination with a VEGF antagonist.

In one aspect, the present invention includes a method of inhibiting or reducing angiogenesis to a subject or subject population in need of comprising (i) identifying a subject or subject population to be a candidate for improved responsiveness to a VEGF antagonist treatment and (ii) administering a vector encoding a Fas chimera protein and the VEGF antagonist to the subject or the subject population, wherein the subject or subject population has improved responsiveness to a VEGF antagonist after the administration of the vector.

In another aspect, the present invention includes a method of inhibiting or reducing angiogenesis to a subject or a subject population in need of induced or improved responsiveness to a VEGF antagonist comprising administering a vector encoding a Fas chimera protein and the VEGF antagonist to the subject or the subject population, wherein the subject or the subject population has improved responsiveness to a VEGF antagonist after the administration of the vector.

In other aspects, identifying a subject or a subject population to be a candidate for improved responsiveness to a VEGF antagonist comprises (a) administering a VEGF antagonist alone, (b) measuring responsiveness to the VEGF antagonist, (c) administering a vector encoding a Fas chimera protein, (d) administering the VEGF antagonist, (e) measuring responsiveness to the VEGF antagonist in (d), and (f) comparing the responsiveness in (b) with the responsiveness in (d). The subject or the subject population demonstrating a higher responsiveness in (e) than (b) can be identified as a subject in need of induced or improved responsiveness to the VEGF antagonist. The subject or the subject population demonstrating an equal responsiveness between (b) and (e) or a higher responsiveness in (b) than (e) can be identified as a non-candidate and can be excluded from further therapy.

In one embodiment, the invention is directed to a method of inducing apoptosis of an endothelial cell in a tumor of a subject in need thereof comprising administering a VEGF antagonist to the subject, wherein the subject is administered with a vector which comprises a Fas-chimera gene operably linked to an endothelial cell specific promoter prior to the administration of the VEGF antagonist and wherein the responsiveness of the subject to the VEGF antagonist is increased after administration of the vector. In another embodiment, the invention provides a method of inducing apoptosis of an endothelial cell in a tumor of a subject in need thereof comprising: (i) administering a vector which comprises a Fas-chimera gene operably linked to an endothelial cell specific promoter, wherein the responsiveness of the subject to a VEGF antagonist is increased after administration of the vector, and (ii) administering the VEGF antagonist to the subject. In other embodiments, the invention includes a method of inducing apoptosis of an endothelial cell in a tumor of a subject in need thereof comprising (i) administering a vector which comprises a Fas-chimera gene operably linked to an endothelial cell specific promoter, (ii) administering a VEGF antagonist to the subject, and (iii) measuring responsiveness of the subject to the VEGF antagonist, wherein the responsiveness of the subject is increased after the administration of the vector. In yet other embodiments, the tumor size of the subject is reduced after the administration of the VEGF antagonist.

In certain embodiments, the invention provides a method of reducing the size of a tumor in a subject in need thereof comprising administering a VEGF antagonist to the subject, wherein the subject is administered with a vector which comprises a Fas-chimera gene operably linked to an endothelial cell specific promoter prior to the administration of the VEGF antagonist, wherein the responsiveness of the subject to the VEGF antagonist is increased after administration of the vector and before administration of the VEGF antagonist, and wherein the tumor size in the subject is reduced after administration of the VEGF antagonist. In some embodiments, the invention provides a method of reducing the size of a tumor in a subject in need thereof comprising: (i) administering a vector which comprises a Fas-chimera gene operably linked to an endothelial cell specific promoter, wherein the responsiveness of the subject to the VEGF antagonist is increased after the administration of the vector, and (ii) administering a VEGF antagonist to the subject, wherein the tumor size in the subject is reduced after administration of the VEGF antagonist. The present invention also includes a method of reducing the size of a tumor in a subject in need thereof comprising: (i) administering a vector which comprises a Fas-chimera gene operably linked to an endothelial cell specific promoter, (ii) administering a VEGF antagonist to the subject; and (iii) measuring the responsiveness of the subject to the VEGF antagonist, wherein the responsiveness of the subject to the VEGF antagonist is increased after the administration of the vector. In other embodiments, the tumor size is reduced compared to the tumor size of a subject who is not administered with the vector prior to the administration of the VEGF antagonist. In yet other embodiments, the tumor size is measured by comparing the size of the tumor prior to the administration of the VEGF antagonist and the size of the tumor after the administration of the VEGF antagonist.

In certain embodiments, the invention includes a method of treating a disease or condition associated with tumor in a subject comprising administering a VEGF antagonist to a subject in need thereof, wherein the subject is administered with a vector which comprises a Fas-chimera gene operably linked to an endothelial cell specific promoter prior to the administration of the VEGF antagonist and wherein the responsiveness of the subject to the VEGF antagonist is increased after administration of the vector and before administration of the VEGF antagonist. The invention is also directed to a method of treating a disease or condition associated with tumor in a subject comprising (i) administering a vector which comprises a Fas-chimera gene operably linked to an endothelial cell specific promoter, wherein the responsiveness of the subject to a VEGF antagonist is increased after the administration of the vector, and (ii) administering the VEGF antagonist to the subject. In some embodiments, the invention provides a method of treating a disease or condition associated with tumor in a subject comprising (i) administering a vector which comprises a Fas-chimera gene operably linked to an endothelial cell specific promoter, (ii) administering a VEGF antagonist to the subject; and (iii) measuring responsiveness of the subject to the VEGF antagonist, wherein the responsiveness of the subject to the VEGF antagonist is increased after administration of the vector. In other embodiments, the tumor of the subject is progressed after the administration of the vector.

In some embodiments, the invention includes a method of identifying a candidate for a VEGF antagonist therapy comprising (i) measuring a tumor size of a subject who is diagnosed as having a tumor prior to administering a vector which comprises a Fas-chimera gene operably linked to an endothelial cell specific promoter to the subject and (ii) measuring progression of the tumor after the administration of the vector, wherein the subject is identified as a candidate after the tumor is progressed. In other embodiments, the invention provides a method of identifying a candidate for a VEGF antagonist therapy comprising (i) measuring a tumor size of a subject who is diagnosed as having a tumor prior to administering a vector which comprises a Fas-chimera gene operably linked to an endothelial cell specific promoter to the subject, (ii) measuring progression of the tumor after the administration of the vector, wherein the subject is identified as a candidate after the tumor is progressed, and (iii) instructing a healthcare provider to administer a VEGF antagonist to the subject. In certain aspects, the tumor progression is measured by the growth of the tumor. In some embodiments, clinical progression is assessed by clinical deterioration in the patients neurological signs and symptoms such as muscle weakness and mental status.

In a particular embodiment, the growth of the tumor is measured by MRI. In other embodiments, the tumor of the subject is a recurrent tumor that arose during treatment with the vector. In yet other embodiments, the tumor of the subject is a metastatic tumor that arose during treatment with the vector.

The term "subject" or "individual" or "animal" or "patient" or "mammal," is meant any subject, particularly a mammalian subject, having or being expected to have increased or improved responsiveness to a VEGF antagonist. In some embodiments, the subject is meant any subject previously non-responsive to a VEGF antagonist, but becomes responsive to the VEGF antagonist after exposure to the vector. In one embodiment, the subject is a human. In another embodiment, the subject is a cancer patient.

The phrase "subject or subject population in need of induced or improved responsiveness to a VEGF antagonist" as used herein indicates that the subject or the subject population has been identified as a candidate or candidates for the combination therapy. The subject or subject population can be identified as being a candidate or candidates for the combination therapy prior to the administration of the vector or the VEGF antagonist.

In certain embodiments, identifying a candidate for the combination therapy comprises measuring various characteristics of tumor angiogenesis, for example, reduction in size of the tumor, inhibition of tumor growth, reduction in angiogenesis, reduction in neo-vascularization, or any known characteristics of angiogenesis.

In one aspect, the subject or the subject population in need of improved or induced responsiveness to a VEGF antagonist has a tumor or a metastasis thereof, wherein the VEGF antagonist and the vector treat, decrease, or reduce the size of a tumor or a metastasis thereof. In another aspect, the subject or the subject population in need of improved or induced responsiveness to a VEGF antagonist needs angiogenesis inhibition, wherein the vector and the VEGF antagonist treat, decrease, prevent, or reduce angiogenesis. In other aspects, the subject or the subject population in need of improved or induced responsiveness to a VEGF antagonist has cancer, wherein the vector and the VEGF antagonist treat cancer.

In certain aspects, once the subject or the subject population is identified as a candidate, the VEGF antagonist is administered prior to administering the vector, concomitantly with administration of a vector, or after administration of a vector. In other aspects, after a subject or a subject population is identified as a candidate, the vector is administered prior to the VEGF antagonist for at least one day earlier, at least two days earlier, at least three days earlier, at least four days earlier, at least five days earlier, at least six days earlier, at least seven days earlier, at least nine days earlier, at least 10 days earlier, at least two weeks earlier at least three weeks earlier, at least four weeks earlier, at least one month earlier, at least two months earlier, or more.

In one embodiment of the present invention, the invention includes a method of stabilizing a disease or disorder associated with cancer. In some embodiments, the invention includes a method of stabilizing a disease or disorder associated with metastatic colorectal cancer (mCRC), advanced nonsquamous non-small cell lung cancer (NSCLC), metastatic renal cell carcinoma (mRCC), glioblastoma multiforme (GBM), Müllerian cancer, ovarian cancer, peritoneal cancer, fallopian tube cancer, or uterine papillary serousspects, the present invention reduces the volume of malignant peritoneal fluid, e.g., ascites, reduces pain to the subject, prolongs survival of the subject, or any combinations thereof. The tumor that can be reduced, inhibited, or treated with the combination of the vector and the VEGF antagonist can be a solid tumor, a primary tumor, or a metastatic tumor. The term "metastatic" or "metastasis" refers to tumor cells that are able to establish secondary tumor lesions in another parts or organ.

A "solid tumor" includes, but is not limited to, sarcoma, melanoma, carcinoma, or other solid tumor cancer. "Sarcoma" refers to a tumor which is made up of a substance like the embryonic connective tissue and is generally composed of closely packed cells embedded in a fibrillar or homogeneous substance. Sarcomas include, but are not limited to, chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" refers to a tumor arising from the melanocytic system of the skin and other organs. Melanomas include, for example, acra-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, metastatic melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma viflosum.

Additional cancers that may be inhibited or treated include, for example, Leukemia, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, premalignant skin lesions, testicular cancer, lymphomas, thyroid cancer, papillary thyroid cancer, neuroblastoma, neuroendocrine cancer, esophageal cancer, genitourinary tract cancer, malignant hypercalcemia, cervical cancer, endometrial cancer, adrenal cortical cancer, prostate cancer, Müllerian cancer, ovarian cancer, peritoneal cancer, fallopian tube cancer, or uterine papillary serous carcinoma.

In other embodiments, the subject has had up to three, up to two, or up to one previous line of chemotherapy. In yet other embodiments, the subject has not had more than 3 prior lines of chemotherapy for recurrent cancer.

In certain embodiments, the invention provides a method for inducing or improving responsiveness to a vascular endothelial growth factor (VEGF) antagonist in a subject or a subject population in need thereof, comprising administering a vector which comprises a Fas-chimera gene operably linked to an endothelial cell specific promoter, and the VEGF antagonist to the subject or the subject population, wherein the responsiveness to the VEGF antagonist is induced or improved after the administration of the vector compared to the responsiveness to the VEGF antagonist without the administration of the vector.

In certain embodiments, once the subject or the subject population is identified as a candidate, the method further comprises administering repeated doses of the VEGF antagonist and the vector.

The dose of the vector administered as part of the present invention can be measured in virus particles (VPs). In one embodiment, the dose of the vector in the combination therapy with bevacizumab is lower than the dose that is used for the therapy without bevacizumab (e.g., a therapy using the vector alone). For example, an effective amount of the vector in the combination therapy with bevacizumab includes, but is not limited to equal to or less than about $1\times10^{13}$, $9\times10^{12}$, $8\times10^{12}$, $7\times10^{12}$, $6\times10^{12}$, $5\times10^{12}$, $4\times10^{12}$, $3\times10^{12}$, $2\times10^{12}$, $1\times10^{12}$, $9\times10^{11}$, $8\times10^{11}$, $7\times10^{11}$, $6\times10^{11}$, $5\times10^{11}$, $4\times10^{11}$, $3\times10^{11}$, $2\times10^{11}$, $1\times10^{11}$, $9\times10^{10}$, $8\times10^{10}$, $7\times10^{10}$, $6\times10^{10}$, $5\times10^{10}$, $4\times10^{10}$, $3\times10^{10}$, $2\times10^{10}$, or $1\times10^{10}$ virus particles.

In one embodiment, the vector is administered at an effective amount of at least about $1\times10^{11}$ virus particles. In another embodiment, the vector is administered at an effective amount of at least about $1\times10^{12}$ virus particles. In another embodiment, the vector is administered at an effective amount of at least about $1\times10^{13}$ virus particles. In another embodiment, the vector is administered at an effective amount of at least about $1\times10^{14}$ virus particles. In other embodiments, the vector is administered at an effective amount of at least about $1\times10^{7}$, $1\times10^{8}$, $1\times10^{9}$, $1\times10^{10}$, or $5\times10^{10}$ virus particles.

The dose of the VEGF antagonist (e.g., bevacizumab) can be measured in mg/kg body weight. In one aspect, the dose of bevacizumab in the combination therapy with the vector is lower than the dose of bevacizumab without the vector (e.g., a therapy using bevacizumab alone). Non-limiting examples of an effective amount of bevacizumab include equal to or less than about 15 mg/kg, 14 mg/kg, 13 mg/kg, 12 mg/kg, 11 mg/kg, 10 mg/kg, 9 mg/kg, 8 mg/kg, 7 mg/kg, 6 mg/kg, 5 mg/kg, 4 mg/kg, 3 mg/kg, 2 mg/kg, or 1 mg/kg.

In a specific embodiment, the vector is administered at an effective amount of $3\times10^{12}$ to $1\times10^{13}$ VPs and bevacizumab is administered at an effective amount of 5 mg/kg to 15 mg/kg.

The present invention provides methods of inducing or improving responsiveness to VEGF antagonists comprising administering a vector and a VEGF antagonist. The regimen used for administering the vector and the VEGF antagonist comprises repeated administration of the vector and the bevacizumab. In one embodiment, the vector is repeatedly administered every day, once in about 2 days, once in about 3 days, once in about 4 days, once in about 5 days, once in about 6 days, once in about 7 days, once in about 2 weeks, once in about 3 weeks, once in about 4 weeks, once in about 5 weeks, once in about 6 weeks, once in about 7 weeks, once in about 2 months, or once in about 6 months. In another embodiment the bevacizumab is repeatedly administered once in about 7 days, once in about 2 weeks, once in about 3 weeks, once in about 4 weeks, once in about 2 months, once in about 3 months, once in about 4 months, once in about 5 months, or once in about 6 months. In a particular embodiment, the vector is administered every 2 months and bevacizumab is administered every 2 weeks.

V. Pharmaceutical Compositions

Also provided in the invention is a pharmaceutical composition comprising a vector expressing a FAS-chimera protein used in the methods of the invention. The pharmaceutical composition can be formulated for administration to mammals, including humans. The pharmaceutical compositions used in the methods of this invention comprise pharmaceutically acceptable carriers, including, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. In one embodiment, the composition is formulated by adding saline.

The compositions of the present invention may be administered by any suitable method, e.g., parenterally (e.g., includes subcutaneous, intravenous, intramuscular, intra-articular, intra-synovial, intrasternal, intrathecal, intrahepatic, intralesional and intracranial injection or infusion techniques), intraventricularly, orally, by inhalation spray, topically, rectally, nasally, buccally, vaginally or via an implanted reservoir. As described previously, the composition comprising a nucleic acid construct which comprises a FAS-chimera gene in an endothelial cell and thereby induces apoptosis of the endothelial cell. Accordingly, the composition can inhibit, reduce, or decrease the size of a tumor or a metastasis thereof by inhibiting neo-vascularization and/or angiogenesis of the tumor endothelial cells. Likewise, the VEGF antagonist used in combination with the nucleic acid construct inhibit neo-vascularization and/or angiogenesis through direct inhibition of VEGF activity. Therefore, in one embodiment, the combination therapy is delivered systemically or locally. For systemic or local delivery, the pharmaceutical formulation containing the nucleic acid construct, the adenovirus, or the homogeneous population of the adenovirus can utilize a mechanical device such as a needle, cannula or surgical instruments.

Sterile injectable forms of the compositions used in the methods of this invention may be aqueous or oleaginous suspension. These suspensions may be formulated according to techniques known in the art using suitable dispersing or wetting agents and suspending agents. The sterile, injectable preparation may also be a sterile, injectable solution or suspension in a non-toxic parenterally acceptable diluent or solvent, for example as a suspension in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Parenteral formulations may be a single bolus dose, an infusion or a loading bolus dose followed with a maintenance dose. These compositions may be administered at specific fixed or variable intervals, e.g., once a day, or on an "as needed" basis.

Certain pharmaceutical compositions used in the methods of this invention may be orally administered in an acceptable dosage form including, e.g., capsules, tablets, aqueous suspensions or solutions. Certain pharmaceutical compositions also may be administered by nasal aerosol or inhalation. Such compositions may be prepared as solutions in saline, employing benzyl alcohol or other suitable preservatives, absorption promoters to enhance bioavailability, and/or other conventional solubilizing or dispersing agents.

An effective amount of the chemotherapeutic agent is available in the art. In one aspect, for example, an effective amount of bevacizumab can be at least about 1 mg/kg, 2 mg/kg, 3 mg/kg, 4 mg/kg, or 5 mg/kg.

EXAMPLES

Example 1

Construction and Cloning of the Viral Vector

The vector was constructed using a backbone containing most of the genome of adenovirus type 5, as well as partial homology to an adaptor plasmid, which enables recombination.

The E1 early transcriptional unit was deleted from the backbone plasmid, and further modified by deleting the pWE25 and the Amp resistance selection marker site.

The adaptor plasmid, containing sequences of the Ad5, CMV promoter, MCS, and SV40 polyA was modified to delete deleting the CMV promoter, and the PPE-1 promoter and Fas-c fragment were inserted by restriction digestion. The modified PPE-1 promoter (PPE-1-3X, SEQ ID NO: 18) and the Fas-chimera transgene (Fas-c, SEQ ID NO: 9) were utilized for construction of the adenoviral vector. The PPE-1-(3X)-Fas-c element (2115 bp) was constructed from the PPE-1-(3X)-luc element. This element contains the 1.4 kb of the murine preproendothelin PPE-1-(3X) promoter, the Luciferase gene, the SV40 polyA site and the first intron of the murine ET-1 gene, originated from the pEL8 plasmid (8848 bp) used by Harats et al (Harats D. et al., JCI, 1995). The PPE-3-Luc cassette was extracted from the pEL8 plasmid using the BamHI restriction enzyme. The Luciferase gene was substituted by the Fas-c gene [composed of the extra cellular and intra membranal domains of the human TNF-R1 (Tumor Necrosis Factor Receptor 1, SEQ ID NO: 4) and of the Fas (p55) intracellular domain (SEQ ID NO: 8) (Boldin et al, JBC, 1995)] to obtain the PPE-1-3x-Fas-c cassette.

PPE-1 (3x)-Fas-c Plasmid—The cassette was further introduced into the backbone plasmid by restriction digestion, resulting with the PPE-1 (3x)-Fas-c plasmid.

Adaptor-PPE-1(3x)-Fas-c Plasmid—The PPE-1-3x-Fas-c element was extracted from the first generation construct PPE-1-3x-Fas-c plasmid, and was amplified with designated PCR primers introducing SnaB1 and EcoR1 restriction sites at the 5'-and-3'-end respectively. These sites were used to clone the PPE-Fas-c fragment into the adaptor plasmid digested with SnaB1 and EcoR1, resulting in the adaptor-PPE-1-3x-Fas-c used for transfection of the host cells (for example, PER.C6 cells).

Example 2

Administration of Bevacizumab to Patients Previously Treated with Ad5-PPE-1-3X-Fas-c OBJECTIVES: The objectives of this study are: (i) to evaluate the safety, tolerability, and efficacy of single and multiple doses of VB-111 ($1 \times 10^{12}$, $3 \times 10^{12}$, $1 \times 10^{13}$ viral particles [VP]) in patients with recurrent glioblastoma multiforme (GBM); (ii) to evaluate the distribution of VB-111 after single and multiple IV infusions and the level of antibodies to the adenovirus vector; and (iii) to evaluate the safety, tolerability, and efficacy of combination treatment of multiple doses of VB-111 ($3 \times 10^{12}$, or $1 \times 10^{13}$ viral particles) together with bevacizumab in patients with recurrent GBM. An example of such a treatment regimen is shown in FIG. 1.

VB-111 and bevacizumab are both anti-angiogenic agents that target the tumor vasculature. However, they do so based on two distinct MOAs: Bevacizumab antagonizes VEGF while VB-111 directly disrupts the angiogenic vessels.

Patient Selection
Inclusion Criteria

Subjects must have a histologically confirmed diagnosis of glioblastoma multiforme or gliosarcoma. Subjects with recurrent disease whose diagnostic pathology confirmed glioblastoma multiforme or gliosarcoma will not need re-biopsy;

Measurable disease by RANO criteria (see Screening, Day −21-0); see also Table 8 in Example 4;

Subjects ≥18 years of age;

Disease progression or recurrence following standard of care treatment with temozolomide and radiation;

An interval of at least 4 weeks between prior surgical resection and study enrollment;

An interval of at least 12 weeks between prior radiotherapy or at least 4 weeks from prior chemotherapy, and enrollment in this protocol;

Recovered to Grade 1 or less from the toxic effects of any earlier intervention;

Karnofsky performance status of at least 60%;

Adequate renal, liver, and bone marrow function according to the following criteria:

Absolute neutrophil count ≥1500 cells/ml
Platelets ≥125,000 cells/ml
Total bilirubin within upper limit of normal (ULN)
Aspartate aminotransferase (AST)≤2.5×institutional ULN
Creatinine less than or equal to the ULN or creatinine clearance ≥50 mL/min for patients with creatinine levels above normal limits. (creatinine clearance calculated by the Cockcroft-Gault formula, see Appendix II).

PT, PTT (in seconds) prolonged beyond >20% of the upper limits of normal.

Subjects must be treated with corticosteroids on day 0. Subjects already administering steroids must be on a stable dose for at least 1 week prior to entry with no anticipation of a need to increase the steroid dose throughout the study;

Ability to understand and willingness to sign a written informed consent document;

Males and females of childbearing potential must utilize a standard contraception method throughout the course of the trial.

Cohorts 1 and 2 Additional Eligibility Criteria:
Subjects without major mass effect of tumor (defined as <5 mm shift, no herniation).

Cohorts 3-4 Additional Eligibility Criteria for Further Dosing:

Subject received VB-111 at least 2 months ago, and remains without evidence of disease progression for at least 2 months after dosing. Note: Subjects that received the first dose more than 2 months prior to approval of this multiple dose amendment, may be eligible to receive the 2nd dose later than 2 months after the first dose, provided they remain with stable disease. Subjects who progressed later than 2 months after the baseline dose may be eligible for the compassionate use protocol VB-111-122-CU. Subjects who progress earlier than 2 months post dosing will discontinue the study.

Subjects who experienced a VB-111 drug related adverse event, and are scheduled for a repeat dose, the repeat dose will be delayed until the severity of the event is no more than CTCAE Grade 1.

Subjects who experienced a prolongation of PTT and are scheduled for a repeat dose, the repeat dose will be delayed until the PTT has normalized returned to within 20% of the baseline value, whether any positive LAC or APLA test has normalized or not. Subjects with clinically significant thrombotic or bleeding events related to a prolonged PTT should not receive additional doses of VB-111.

Exclusion Criteria

Prior anti-angiogenic therapy including VEGF sequestering agents (ie bevacizumab, aflibercept, etc) or VEGFR inhibitors (cedirinib, pazopanib, sunitinib, sorafenib, etc);

Prior stereotactic radiotherapy;

Pregnant or breastfeeding subjects;

Concomitant medication that may interfere with study results; e.g. immunosuppressive agents other than corticosteroids;

Active infection;

Evidence of CNS haemorrhage CTCAE grade 2 or above on baseline MRI;

Expected to have surgery during study period;

Subjects who suffered from an acute cardiac event within the last 12 months;

Subjects with active vascular disease, either myocardial or peripheral (i.e. acute coronary syndrome, cerebral stroke, transient ischemic attack or arterial thrombosis or symptomatic peripheral vascular disease within the past 3 months);

Subjects with known proliferative and/or vascular retinopathy;

Subjects with known liver disease (alcoholic, drug/toxin induced, genetic, or autoimmune);

Subjects with known active second malignancy;

Subjects testing positive to one of the following viruses: HIV, HBV and HCV;

Subjects that have undergone major surgery within the last 4 weeks before enrollment;

Subjects may not have received any other investigational agent within 4 weeks before enrollment;

Uncontrolled intercurrent illness including, but not limited to ongoing or active infection, symptomatic congestive heart failure, unstable angina pectoris, cardiac arrhythmia, or psychiatric illness/social situations that would limit compliance with study requirements.

Bevacizumab-Specific Exclusion Criteria

Inadequately controlled hypertension (defined as systolic blood pressure >150 mmHg and/or diastolic blood pressure >100 mmHg) within 28 days of first study treatment;

Prior history of hypertensive crisis, hypertensive encephalopathy, reverse posterior leukoencephalopathy syndrome (RPLS);

Prior history of gastrointestinal perforation or abscess;

Clinically significant (i.e. active) cardiovascular disease, for example cerebrovascular accidents ≤6 months prior to study enrollment, myocardial infarction ≤6 months prior to study enrollment, unstable angina, New York Heart Association (NYHA) Grade II or greater congestive heart failure (CHF), or serious cardiac arrhythmia uncontrolled by medication or potentially interfering with protocol treatment;

History or evidence upon physical/neurological examination of central nervous system disease (e.g. seizures) unrelated to cancer or potentially interfering with protocol treatment (unless adequately controlled by medication);

Significant vascular disease (e.g., aortic aneurysm requiring surgical repair or recent arterial thrombosis) within 6 months prior to start of study treatment. Any previous venous thromboembolism >NCI common toxicity criteria adverse event (CTCAE) Grade 3;

History of pulmonary hemorrhage/hemoptysis≥grade 2 (defined as ≥2.5 mL bright red blood per episode) within 1 month of first study treatment;

History or evidence of inherited bleeding diathesis or significant coagulopathy at risk of bleeding (i.e. in the absence of therapeutic anticoagulation);

Current or recent (within 10 days of study enrollment) use of aspirin (>325 mg/day), clopidogrel (>75 mg/day) or equivalent. Prophylactic use of anticoagulants is allowed;

Surgical procedure (including open biopsy, surgical resection, wound revision, or any other major surgery involving entry into a body cavity) or significant traumatic injury within 28 days prior to first study treatment, or anticipation of need for major surgical procedure during the course of the study;

Minor surgical procedure, e.g. stereotactic biopsy, within 7 days of first study treatment; placement of a vascular access device, within 2 days of first study treatment;

History of intracranial abscess within 6 months prior to first study treatment;

History of active gastrointestinal bleeding within 6 months prior to first study treatment;

Serious, non-healing wound, active ulcer, or untreated bone fracture;

Known hypersensitivity to any component of bevacizumab or any of the study drugs.

Proteinuria at screening as demonstrated by either:
Urine protein: creatinine (UPC) ratio ≥1.0 at screening OR
Urine dipstick for proteinuria ≥2+ (patients discovered to have ≥2+ proteinuria on dipstick urinalysis at baseline should undergo a 24 hour urine collection and must demonstrate ≤1 g of protein in 24 hours to be eligible)

Treatment Plan

This will be a prospective, open label, dose escalating, multi-center, Phase 1/2 study, measuring the safety, tolerability, distribution, and efficacy of single or multiple doses of intravenously administered VB-111 in patients with recurrent GBM.

Dose Cohorts

VB-111 will be administered as a single intravenous infusion of $1\times10^{12}$ (Cohort 1) or $3\times10^{12}$ VP (Cohort 2), or multiple intravenous infusions consisting of an initial infusion of $3\times10^{12}$ followed by subsequent infusions of $1\times10^{13}$ (Cohort 3) or multiple intravenous infusions of $1\times10^{13}$ (Cohort 4).

Eligible, consenting patients will be enrolled into one of four sequential dosing cohorts as follows:

TABLE 5

Dosing Plan

| Cohort | VB-111 (vp) | Patients No. |
|---|---|---|
| 1 | $1 \times 10^{12}$ Single Dose | 3-6 |
| 2 | $3 \times 10^{12}$ Single Dose | 3-6 |
| 3 | $3 \times 10^{12}$ Initial Dose + $1 \times 10^{13}$ Repeat Dose | Minimum of 3 Maximum of 29 |
| 4 | $1 \times 10^{13}$ Multiple Doses | Maximum of 49 |
| 3-4 EXT | $1 \times 10^{13}$ (Q2 months) + 10 mg/kg bevacizumab (Q2 weeks) | Maximum of 29 |

The study will be conducted according to the Simon's 2 step method. Up to 90 subjects are anticipated to enroll in this study, with up to 29 subjects in Cohort 3, and up to 49 subjects in Cohort 4.

Step one will include the first 10 evaluable patients at the $1\times10^{13}$ VP dose level or MTD.

For efficacy analysis, evaluable patients will be defined as those who received at least one repeat dose of $1\times10^{13}$ VPs or of MTD, or patients who progressed sooner than 2 months after an initial dose of $1\times10^{13}$ VPs.

A subject will be considered to have a response if s/he is either alive and progression free at 6 months or has at least a partial tumor response according to Rano criteria within 6 months post dosing. If less than 2 responses are observed in the step 1 subjects, step 2 will be halted, otherwise, an additional 19 subjects will enroll in step 2.

Dose Escalation and Dose-Limiting Toxicity

Toxicities will be graded according to the NCI common toxicity criteria Version 4.0. Dose limiting toxicity (DLT) is any grade 3 or higher toxicity judged drug-related that does not respond to maximal medical therapy.

Cohorts 1 & 2:

Three subjects were enrolled sequentially to receive $1\times10^{12}$ (cohort 1) and observed for 28 days for DLT monitoring. No DLTs occurred in cohort 1 and the study proceeded with cohort 2.

Three subjects were enrolled sequentially to receive $3\times10^{12}$ (cohort 2) and observed for 28 days for DLT. No DLTs were reported in cohort 2 and the study proceeded to cohort 3.

Cohort 3:

Study subjects were initially enrolled into this cohort to receive a single dose. Upon approval of Protocol Version 6.0, subjects remaining stable began to receive bi-monthly doses of VB-111 following establishment of safety with repeat doses at a rate of $1\times10^{13}$ VPs.

Cohort 4:

Study subjects will be enrolled sequentially into the multiple dose cohort 4 and will receive VB-111 at $1\times10^{13}$ VPs every 2 months.

Cohorts 3-4 EXT:

Upon disease progression, subjects will receive a combination of VB-111 and bevacizumab. The first subjects receiving this combination treatment will be monitored for DLTs according to the following:

Stage 1: A minimum of 3 subjects will receive bi-monthly doses of VB-111 ($3\times10^{12}$ VPs) and bi-weekly bevacizumab (10 mg/Kg).

Stage 2: A minimum of 3 subjects will receive bi-monthly doses of VB-111 ($1\times10^{13}$ VPs) and bi-weekly bevacizumab (10 mg/Kg).

Refer to Monitoring for Dose Limiting Toxicities below for details on DLT monitoring in Cohorts 3-4.

Monitoring for Dose Limiting Toxicities:

Monitoring for DLTs was performed to establish safety at the beginning of each dose level escalation (Cohorts 1-4; $1\times10^{12}$-$1\times10^{13}$ VPs). No DLTS were observed in this study to date, therefore, the study has proceeded as planned.

For Cohort 3-4 EXT:

Stage 1: Upon each local IRB approval of this protocol amendment (7.0), the first three subjects who progress after receiving at least one dose of $1\times10^{13}$ VPs (initial or repeat) will receive a combination of a reduced dose of VB-111 ($3\times10^{12}$ VPs) and bevacizumab (10 mg/kg). These subjects will be monitored for DLTs following this first combination dose.

[Since a minimum of 2 months is required between doses of VB-111, if a subject progresses before 2 months, the subject will begin treatment with bevacizumab (10 mg/kg) every 2 weeks and at 2 months from the last dose of VB-111, the subject will receives the $3\times10^{12}$ VPs dose of VB-111.]

Among the first 3 subjects enrolled, if 1 DLT is observed within 4 weeks following the initial combination dose, 3 additional subjects will receive a combination dose, and safety will be reassessed.

If two out of six subjects who have received a combination dose of VB-111 ($3\times10^{12}$ VPs) and bevacizumab (10 mg/kg) experience a DLT, dosing in the Cohort 3-4 EXT shall stop and all progressed subjects will be followed for long term follow up and survival.

If no DLTs are observed or only 1 DLT is observed in 6 patients, further dosing will escalate to Stage 2 levels: VB-111 ($1\times10^{13}$ VPs) and bevacizumab (10 mg/kg), see below.

Three subjects were enrolled sequentially and received $3\times10^{12}$ VPs and bevacizumab (10 mg/kg) and observed for 28 days for DLTs. No DLTS were observed in this study to date, therefore, the study proceeded as planned to Stage 2 combination therapy: VB-111 ($1\times10^{13}$ VPs) and bevacizumab (10 mg/kg), see below.

Stage 2:

DLT monitoring will be performed for a minimum of 3 subjects for 4 weeks from the first combination dose of VB-111 ($1\times10^{13}$ VPs) and bevacizumab (10 mg/Kg).

Among the first 3 subjects enrolled at Stage 2 dosing, if 1 DLT is observed within 4 weeks following the initial combination dose, 3 additional subjects receive a combination dose, and safety will be reassessed.

If two out of six subjects who have received a combination dose of VB-111 ($1\times10^{13}$ VPs) and bevacizumab (10 mg/kg) experience a DLT, all future doses in the Cohort 3-4 EXT shall be reduced to VB-111 at $3\times10^{12}$ VPs and bevacizumab (10 mg/kg).

If no DLTs are observed or only 1 DLT is observed in 6 patients, all future Cohort 3-4 EXT dosing will proceed as planned: VB-111 ($1\times10^{13}$ VPs) and bevacizumab (10 mg/kg).

In order to allow sufficient time to monitor for DLTs, scheduling of combination doses will require prior approval from VBL.

Three subjects were enrolled sequentially and received $1\times10^{13}$ VPs and bevacizumab (10 mg/kg) and observed for 28 days for DLTs. No DLTS were observed in this study to date, therefore, all subjects proceeded to receive combined therapy of VB-111 ($1\times10^{13}$ VPs) and bevacizumab (10 mg/kg).

Study Visits

Screening, Day −21-0

Prospective patients will be screened within 3 weeks of enrollment. As a patient is screened, he/she will be given a Patient Identification Number (PIN) by the site study coordinator, which will be recorded in a patient screening log, and will be assessed for eligibility according to the protocol selection criteria. Patients who meet the eligibility criteria will be offered a choice of participation. The PIN consists of the center-number (e.g. 01) plus the patient number in sequential order (e.g. 001, 002, 003, etc.), so the full PIN for center 1 will be 01001, 01002, etc.

Patients will be informed of the advantages, risks and constraints of the study and will be asked to sign an informed consent form.

Patients will then be evaluated by medical history, physical examination and laboratory assessment including ECG. The screening procedures will also include recording the patient's height, weight, date of birth, sex and race.

Medical History: A routine medical history and physical examination will be carried out within 4 weeks prior to enrollment. Baseline laboratory evaluations are to be conducted within 4 weeks prior to start of protocol therapy and at the baseline visit prior to initiation of therapy. Medical history will focus on previous and/or known illnesses, including possible known infections, such as HBV, HIV, HCV, or other infections within the last month, cardiac disease, and liver disease. Medications taken on a regular basis, including those taken in the last month will be recorded. Chemotherapy and radiotherapy and/or immune suppressive treatments taken in the previous 12 weeks will be recorded, as well as surgeries done within this time period. Women are asked for pregnancy and breastfeeding status.

Karnofsky Performance Status (KPS) and ECOG should be performed at Screening.

Physical Examination:

Physical Examination will focus on tumor organs and tumor measurements, according to RANO criteria, as well as the following: Head and neck; Eyes; Lungs; Heart; Abdomen; Joints; Peripheral circulation; Skin; and Neurologic.

Physical Examination should include collection of height and weight (at screening visit only).

ECG: A standard 12-lead electrocardiogram with rhythm strip should be performed.

Laboratory Analyses: Blood: Blood will be collected at a fasting state and analyzed for the following:

Hematology: complete blood count with INR, PT and activated PTT

Chemistry: electrolytes, creatinine and blood urea, bilirubin, alkaline phosphatase, ALT and AST; calcium, total protein, and albumin, Virus infection tests: HIV, HBV and HCV A serum pregnancy test will be conducted in female patients with childbearing potential Urine: Routine urinalysis will be collected and analyzed with microscopic examination on positives Vital Signs: The vital signs (supine systolic and diastolic blood pressure, peripheral heart rate, temperature, respiration rate) will be recorded at screening.

Tumor Measure: Contrast and non-contrast brain MRI imaging will be done at screening and within 72 hours of the baseline visit to assess extent of cancer. If there are less than 2 weeks between screening and baseline visits, only 1 MRI will be required.

Pregnancy: Eligible female subjects will be informed of special restrictions with regards to pregnancy and breast feeding throughout the study period. Both male and female subjects will commit to use one standard contraceptive method on a regular basis throughout the study period starting from screening. Both men and women should not attempt pregnancy and women should not be pregnant or breast-feeding while participating in this study. If sexually active, both men and women should use an effective method of birth control from the screening visit and for up to one year after treatment. Barrier contraceptives (condoms or diaphragms) with spermicide, intrauterine devices, hormonal contraceptives (Depo-Provera, Norplant), oral contraceptive pills, and complete abstinence are examples of effective methods.

Final Patient Selection: The final decision about the eligibility of the patient to be enrolled is to be made after all screening evaluations are available. All inclusion and exclusion criteria MUST be met. The reason for all screen failures will be captured via the Screening Log.

Baseline (Study Drug Administration), Day 0

VB-111 will be administered as an outpatient. Once the subject is found eligible, he/she will be appointed to arrive at the clinic within 3 weeks from screening in a fasting state until 30 minutes following study drug administration.

Prior to dosing (D0): On the day of admission to the site, each subject will be verified for eligibility according to inclusion/exclusion criteria (where applicable) and then tested within 24 hours prior to dosing for the following evaluations.

Laboratory Analyses (According to the Operation Manual):

Blood samples will be collected for the following evaluations:
Hematology: hemoglobin, complete blood count with differential, INR, PT and activated PTT;
Chemistry: electrolytes, creatinine and blood urea nitrogen, bilirubin, alkaline phosphatase, ALT and AST, calcium, total protein and albumin;
Antibody, biodistribution (VB-111 adenovirus DNA levels) and transgene expression determination.
Angiogenic Biomarker/Cytokine samples:
Levels of von Willebrand factor (vWF) and TNFα (optional).
In addition, blood samples for TNF, sTNFRI, sTNFRII, VEGF, FGF, IL-6, IL-8, E-selectin, ICAM-1
Urine will be collected for the following evaluations:
Routine urine analysis
Cohorts 1-2 only: Biodistribution (VB-111 adenovirus DNA levels)

Vital Signs: Vital signs (supine, systolic and diastolic blood pressure, peripheral heart rate, body temperature, respiration rate) will be recorded 15 minutes prior to dosing.

Anti-Pyretic Treatment: To avoid fever following study drug administration, all patients will receive 1000 mg of acetaminophen starting 1-2 hours prior to dosing followed by 500 mg PRN 24 hours.

Corticosteroid Treatment: To reduce potential edema response during drug administration, dexamethasone treatment will be administered:

Initial dose with VB-111: 10 mg will be administered 30 minutes prior to dosing, followed by 4 mg×2/day for 14 days post dosing. Subsequent doses with VB-111: 10 mg will be administered 30 minutes prior to dosing, followed by 4 mg×2/day for 3 days post dosing. Further corticosteroid treatment will be administered at Investigator's discretion. If subjects begin the study already on steroids, all efforts should be made by the Investigator not to change the steroid dose within 5 days of disease assessment, unless clinically warranted. A decision to continue the steroids or to begin tapering after this period of time is at the discretion of the Investigator.

Study Drug Administration: Drug preparation and Infusion will be done according to the operation manual. Maximum time for drug in saline is 1.5 hours at room temperature. The vials should be opened in a biological safety cabinet. VB-111 will be infused to the patient at the relevant dosage according to the patient's weight, according to the Operations Manual. For patients less than 50 Kg of weight, a dose of $3\times10^{12}$ or $1\times10^{13}$ VPs will be reduced by 30%. VB-111 should be administered at 1 ml/minute or 3 ml/minute ($1\times10^{13}$ VPs only). A regular meal will be allowed 0.5 hour after dosing. As previously planned, the first three subjects who received a repeat dose of $1\times10^{13}$ VPs (following a previous dose of $3\times10^{12}$ VPs from cohort 3 or an initial dose of $1\times10^{13}$ VPs in cohort 4) were monitored in an in-patient setting for an 8 hour period after their infusions. No infusion rate-related adverse events were reported.

Up to 6 hours following Drug Administration, Day 0:

Laboratory Analyses:
Biodistribution: Blood sample will be collected for VB-111 adenovirus DNA level expression determinations at the following time points:
0 (Prior to dosing, see above)
At end of infusion
3±0.5 hours
6±0.5 hours
Cohorts 1-2 only: Urine samples will be collected for VB-111 adenovirus DNA levels determinations:
0 (prior to dosing, see above)
Between 0-3 hours
Between 3-6 hours
Angiogenic Biomarker/Cytokine Samples: Blood samples will be collected at 6 hours post dose for:
Levels of von Willebrand factor (vWF) and TNFα (optional).
In addition, blood samples for TNF, sTNFRI, sTNFRII, VEGF, FGF, IL-6, IL-8, E-selectin, ICAM-1
Vital Signs: The vital signs (systolic and diastolic blood pressure, peripheral heart rate, body temperature, respiration rate) will be recorded at 30 and 60 minutes after dosing and at 4 and 6 hours post dosing, and/or upon disappearance of any adverse event, whichever comes first.

Adverse Events: Full supportive measures will be employed for all patients with an adverse event. All adverse events occurring following drug administration will be documented in the case report forms (CRFs), together with the intensity, the therapeutic measures applied, the outcome and the relationship to the investigational drug. Related adverse events will be followed through resolution. Unrelated adverse events will be followed through resolution or end of study.

Concomitant Medications: There is no restriction on concomitant medication, besides the drugs listed in the exclusion criteria. However, VB-111 should not be mixed with other drugs. All concomitant medication administered during the study will be documented from baseline throughout participation or Early Termination visit.

Other Laboratory Analyses: Laboratory samples drawn in response to a clinically significant event will be documented as unscheduled laboratory evaluations. In the event of clinically relevant abnormal laboratory values, the tests will be followed-up until the values have returned to within normal range and/or an adequate explanation of the abnormality is found. All such laboratory investigations will be performed at the study site, except for distribution assessments, which will be sent to an Independent Central Laboratory. Should any of these results require confirmation, re-testing will be performed in the same hospital laboratory where possible. Laboratory accreditation certificates and normal reference ranges must be provided for each hospital laboratory.

Follow Up for Cohorts 1 & 2

On Days 4±1, 7±1, 14±2, 28±3, 56±3, 84±3, 112±3, 140±3, 168±7/Early termination, each patient will be required to return to the clinic in a fasting state, for the following evaluations.

Vital signs: Vital signs (supine systolic and diastolic blood pressure, peripheral heart rate, body temperature, respiration rate) will be recorded.

Laboratory Analyses: Blood sample will be collected for the following evaluations:
  Antibody, biodistribution (VB-111adenovirus DNA levels) and transgene expression determination.
  Hematology: hemoglobin, complete blood count, INR, PT, and activated PTT
  Chemistry: electrolytes, creatinine and blood urea nitrogen, bilirubin, alkaline phosphatase, ALT and AST, calcium, total protein and albumin Laboratory samples drawn in response to a clinically significant event will be documented as unscheduled laboratory evaluations.
  Urine samples will be collected for:
  Routine urinalysis
  VB-111 adenovirus DNA levels determinations
  ECG: ECG will be performed on Day 28 and Day 168/early withdrawal visit (if prior to Day 28).

Tumor Measurement: Post study surveillance will include MRI scans every 2 months until 1 year post dosing, and then every 3 months until 2 years post dosing, or until progression. Additionally, Vital signs will be recording at these time points.

Post discontinuation follow-up period: Patients who progress and/or discontinue the study will be followed up by a telephone contact every 2 months for survival.

Follow Up for Cohorts 3 and 4: Day 4 Following D0 Dose, Days 56 and 112 (i.e. Days 4, 60 and 116)

As of the date of approval of this amendment (Amendment 11), the Day 4 visit is no longer required for any subjects in this trial. Prior to the approval of this amendment, the following clinic visit was performed (italics):

On the 4th day following dose at D0, D56 and D112, each patient will be required to return to the clinic in a fasting state for the following evaluations:

Vital signs: Vital signs (supine systolic and diastolic blood pressure, peripheral heart rate, body temperature, respiration rate) will be recorded.

Laboratory Analyses: Blood samples will be collected for the following evaluations:
  Hematology: hemoglobin, complete blood count with differential, INR, PT and activated PTT: In the case of PTT prolongation above ULN, please refer to Section 6.2 Dose Delay/Modification for further instructions.
  Chemistry: electrolytes, creatinine and blood urea nitrogen, bilirubin, alkaline phosphatase, ALT and AST, calcium, total protein and albumin;
  Antibody, biodistribution (VB-111 adenovirus DNA levels) and transgene expression determination.
  Angiogenic Biomarker/Cytokine samples:
    Levels of von Willebrand factor (vWF) and TNFα (optional).
    In addition, blood samples for TNF, sTNFRI, sTNFRII, VEGF, FGF, IL-6, IL-8, E-selectin, ICAM-1
  Urine will be collected for the following evaluations:
  Routine urinalysis Adverse Events: At the follow up visit, the patient will be questioned about possible adverse events which may have occurred from the day of last visit. All adverse events will be documented in the case report forms (CRFs), together with the intensity, the therapeutic measures applied, the outcome and the relationship to the investigational drug. Related adverse events will be followed through resolution. Unrelated adverse events will be followed through resolution or end of study.

Concomitant Medications: At the follow up visit to the investigator, the patient will be questioned about possible medications which may have been taken from the day of last visit. All concomitant medications will be recorded with generic name, indication, dosage, units, frequency, start and stop dates.

Following the analysis of the first 6 subjects participating in Cohort 3 and the first 6 subjects participating in Cohort 4, it will be determined if this visit (Day 4 following Days 56 and 112), can be eliminated for each Cohort.

A Safety follow up telephone contact should be performed 14 days following the second dose (Day 56) visit for the first 3-6 subjects in each Cohorts 3 and 4 to ensure no DLTs have occurred.

Follow Up for Cohorts 3 and 4: Safety Telephone Contact Every Other Month in Between Dosing Visits As of the date of approval of this amendment (Version 7.0), the Days 28 and 84 visits to the clinic are no longer required for any subjects in this trial. A telephone call should be made every other month in between dosing visits (days 28, 84, 140, etc.) to the subject to inquire about AEs and changes in medication.

Prior to the approval of this amendment, the following clinic visit was performed:

One month following the first two infusions (i.e. at D28 and Day 84), each patient will be required to return to the clinic in a fasting state, for the following evaluations:

Vital signs: Vital signs (supine systolic and diastolic blood pressure, peripheral heart rate, body temperature, respiration rate) will be recorded.

Laboratory Analyses: Blood sample will be collected for the following evaluations:
  Hematology: hemoglobin, complete blood count, INR, PT, and activated PTT: In the case of PTT prolongation above ULN, please refer to Section 6.2 Dose Delay/ Modification for further instructions.

Chemistry: electrolytes, creatinine and blood urea nitrogen, bilirubin, alkaline phosphatase, ALT and AST, calcium, total protein and albumin Antibody, biodistribution (VB-111 adenovirus DNA levels) and transgene expression determination.

Angiogenic Biomarker/Cytokine samples:
Levels of von Willebrand factor (vWF) and TNFα (optional).
In addition, blood samples for TNF, sTNFRI, sTNFRII, VEGF, FGF, IL-6, IL-8, E-selectin, ICAM-1

Laboratory samples drawn in response to a clinically significant event will be documented as unscheduled laboratory evaluations.

Urine sample will be collected for: Routine urinalysis

Tumor Measurement: Subjects will be assessed for response using contrast and non-contrast brain magnetic resonance imaging (MRI) with assessment based on the RANO criteria.

Adverse Events: At the follow up visit to the investigator, the patient will be questioned about possible adverse events which may have occurred from the day of last visit. Full supportive measures will be employed for all patients with an adverse event. All adverse events will be documented in the case report forms (CRFs), together with the intensity, the therapeutic measures applied, the outcome and the relationship to the investigational drug. Related adverse events will be followed through resolution. Unrelated adverse events will be followed through resolution or end of study.

Concomitant Medications: At the follow up visit to the investigator, the patient will be questioned about possible medications which may have been taken from the day of last visit. All concomitant medications will be recorded with generic name, indication, dosage, units, frequency, start and stop dates.

Further VB-111 Administration Cohorts 3 and 4 (Every 2 Months Following Initial Dose: Day 56, Day 112, Day 168, Month 8, Etc.)

On the day of admission to the site, each subject will be re-verified for eligibility according to inclusion/exclusion criteria (where applicable) and then tested within 24 hours prior to dosing. Subjects without evidence of progressive disease will be considered for further dosing.

This visit and VB-111 dosing will be repeated every 2 months until disease progression.

The following assessments will be performed:

Tumor Measure: Subjects will be assessed for response using contrast and non-contrast brain magnetic resonance imaging (MRI) with assessment based on the RANO criteria. MRI imaging will be done up to 72 hours prior to dosing to assess extent of cancer.

Physical Exam: Physical Examination will focus on tumor organs and tumor measurements, according to RANO criteria, as well as the following: Head and neck; Eyes; Lungs; Heart; Abdomen; Joints; Peripheral circulation; Skin; and Neurologic.

ECG (Day 56 Only): A standard 12-lead electrocardiogram with rhythm strip should be performed.

Laboratory Analyses (according to the operation manual): Blood sample will be collected for the following evaluations:
Hematology: hemoglobin, complete blood count with differential, INR, PT and activated PTT: In the case of PTT prolongation above ULN, please refer to Section 6.2 Dose Delay/Modification for further instructions.
Chemistry: electrolytes, creatinine and blood urea nitrogen, bilirubin, alkaline phosphatase, ALT and AST, calcium, total protein and albumin;

Antibody, biodistribution (VB-111 adenovirus DNA levels) and transgene expression determination.

Angiogenic Biomarker/Cytokine samples will be collected prior to dosing and 6 hours post dosing only when the patient is observed for a minimum of 6 hours post dose (at the Investigator's discretion):
Levels of von Willebrand factor (vWF) and TNFα (optional).
In addition, blood samples for TNF, sTNFRI, sTNFRII, VEGF, FGF, IL-6, IL-8, E-selectin, ICAM-1

Serum pregnancy test

Urine will be collected for the following evaluation: Routine urine analysis

Vital Signs: Vital signs (supine, systolic and diastolic blood pressure, peripheral heart rate, body temperature, respiration rate) will be recorded 15 minutes prior to dosing.

Anti-Pyretic Treatment: To avoid fever following study drug administration, all patients will receive 1000 mg of acetaminophen 1-2 hours prior to dosing followed by 500 mg every 4 hours for 24 hours.

Corticosteroid Treatment: To reduce potential edema response during drug administration, dexamethasone treatment will be administered: Subsequent doses with VB-111: 10 mg will be administered 30 minutes prior to dosing, followed by 4 mg×2/day for 3 days post dosing. Further corticosteroid treatment will be administered at Investigator's discretion. If subjects begin the study already on steroids, all efforts should be made by the Investigator not to change the steroid dose within 5 days of disease assessment, unless clinically warranted. A decision to continue the steroids or to begin tapering after this period of time is at the discretion of the Investigator.

Study Drug Administration: Infusion will be done according to the operation manual. Prior to infusion, the saline should be brought to room temperature. The vials should be opened in a biological safety cabinet and injected into normal saline for infusion according to the operation manual. The final solution for administration should be administrated not more than 90 minutes after preparation. VB-111 will be infused to the patient at the relevant dosage according to the patient's weight, as detailed in the Operations Manual. For patients less than 50 Kg of weight, a dose of $3 \times 10^{12}$ or $1 \times 10^{13}$ VPs will be reduced by 30%. The intravenous infusions of diluted VB-111 should be administered at 1 ml/minute or 3 mL/minute ($1 \times 10^{13}$ VPs only). A regular meal will be allowed 0.5 hour after dosing.

Adverse Events: Full supportive measures will be employed for all patients with an adverse event. All adverse events occurring following drug administration will be documented in the case report forms (CRFs), together with the intensity, the therapeutic measures applied, the outcome and the relationship to the investigational drug. Related adverse events will be followed through resolution. Unrelated adverse events will be followed through resolution or end of study.

Concomitant Medications: There is no restriction on concomitant medication, besides the drugs listed in the exclusion criteria. However, VB-111 should not be mixed with other drugs. All concomitant medication administered during the study will be documented from baseline until the Day 168 or Early Termination visit.

Other Laboratory Analyses: Laboratory samples drawn in response to a clinically significant event will be documented as unscheduled laboratory evaluations. In the event of clinically relevant abnormal laboratory values, the tests will be followed-up until the values have returned to within normal range and/or an adequate explanation of the abnormality is found. All such laboratory investigations will be performed at the study site, except for distribution assessments, which will be sent to an Independent Central Laboratory. Should any of these results require confirmation, re-testing will be performed in the same hospital laboratory where possible. Laboratory accreditation certificates and normal reference ranges must be provided for each hospital laboratory.

Up to 6 Hours Following Further Drug Administration:

As of the date of approval of this amendment (Amendment 11), the 6 hour observation period is no longer required for any subjects in this trial.

Prior to the approval of this amendment, the following visit schedule was followed (italics):

Laboratory Analyses: Biodistribution: Blood sample will be collected for VB-111 adenovirus DNA level expression determinations at the following time points:
0 (Prior to dosing, see above)
At end of infusion
3±0.5 hours
6±0.5 hours
Angiogenic Biomarker/Cytokine Samples: Blood samples will be collected at 6 hours post dose for:
Levels of von Willebrand factor (vWF) and TNFα (optional).
In addition, blood samples for TNF, sTNFRI, sTNFRII, VEGF, FGF, IL-6, IL-8, E-selectin, ICAM-1

Vital Signs: The vital signs (systolic and diastolic blood pressure, peripheral heart rate, body temperature, respiration rate) will be recorded at 30 and 60 minutes after dosing and at 4 and 6 hours post dosing, and/or upon disappearance of any adverse event, whichever comes first.

Adverse Events: Full supportive measures will be employed for all patients with an adverse event. All adverse events occurring following drug administration will be documented in the case report forms (CRFs), together with the intensity, the therapeutic measures applied, the outcome and the relationship to the investigational drug. Related adverse events will be followed through resolution. Unrelated adverse events will be followed through resolution or end of study.

Concomitant Medications: There is no restriction on concomitant medication, besides the drugs listed in the exclusion criteria. However, VB-111 should not be mixed with other drugs. All concomitant medication administered during the study will be documented from baseline until the Day 168 or Early Termination visit.

Other Laboratory Analyses: Laboratory samples drawn in response to a clinically significant event will be documented as unscheduled laboratory evaluations. In the event of clinically relevant abnormal laboratory values, the tests will be followed-up until the values have returned to within normal range and/or an adequate explanation of the abnormality is found. All such laboratory investigations will be performed at the study site, except for distribution assessments, which will be sent to an Independent Central Laboratory. Should any of these results require confirmation, re-testing will be performed in the same hospital laboratory where possible. Laboratory accreditation certificates and normal reference ranges must be provided for each hospital laboratory.

Upon Disease Progression: Cohort 3-4 Extension

VB-111+Bevacizumab Administration Cohorts 3 and 4 (Every 2 Months Following Disease Progression)

At the time the subject experiences disease progression (any remaining stable subjects from cohort 3 and all subjects from cohort 4), the subject will be asked to participate in an extension phase of this trial, which will administer VB-111 and bevacizumab as a combination therapy. VB-111 ($3 \times 10^{12}$ or $1 \times 10^{13}$ VPs—see Dose Limiting Toxicities above) will be administered bi-monthly and bevacizumab will be administered bi-weekly.

Subjects will be informed of the advantages, risks and constraints of the study and will be asked to sign an informed consent form. Then subjects will be evaluated to ensure they meet the study criteria. Refer to Section 3.0 for Inclusion and Exclusion criteria, including bevacizumab specific exclusion criteria.

Since a minimum of 2 months is required between doses of VB-111, if a subject progresses before 2 months, the subject will begin treatment with bevacizumab (10 mg/kg) every 2 weeks and at 2 months from the last dose of VB-111, the subject will receive the first combination dose.]

The following assessments will be performed:

Tumor Measure; Subjects will be assessed for response using contrast and non-contrast brain magnetic resonance imaging (MRI) with assessment based on the RANO criteria. MRI imaging will be done up to 72 hours prior to dosing to assess extent of cancer.

Physical Exam: Physical Examination will focus on tumor organs and tumor measurements, according to RANO criteria, as well as the following: Head and neck; Eyes; Lungs; Heart; Abdomen; Joints; Peripheral circulation; Skin; and Neurologic.

ECG (to be performed every 6 months from the initial combination dose.

A standard 12-lead electrocardiogram with rhythm strip should be performed.

Laboratory Analyses (according to the operation manual): Blood sample will be collected for the following evaluations:
Hematology: hemoglobin, complete blood count with differential, INR, PT and activated PTT: In the case of PTT prolongation above ULN, please refer to Section 6.2 Dose Delay/Modification for further instructions.
Chemistry: electrolytes, creatinine and blood urea nitrogen, bilirubin, alkaline phosphatase, ALT and AST, calcium, total protein and albumin;
Antibody, biodistribution (VB-111 adenovirus DNA levels) and transgene expression determination.
Angiogenic Biomarker/Cytokine samples are collected prior to dosing and 6 hours post dosing only when the patient is observed for a minimum of 6 hours post dose (at the Investigator's discretion):
Levels of von Willebrand factor (vWF) and TNFα (optional).
In addition, blood samples for TNF, sTNFRI, sTNFRII, VEGF, FGF, IL-6, IL-8, E-selectin, ICAM-1
Serum pregnancy test
Urine will be collected for the following evaluation:
Routine urine analysis
Dipstick for proteinuria Vital Signs: Vital signs (supine, systolic and diastolic blood pressure, peripheral heart rate, body temperature, respiration rate) will be recorded 15 minutes prior to dosing.

Anti-Pyretic Treatment: To avoid fever following study drug administration, all patients will receive 1000 mg of acetaminophen 1-2 hours prior to dosing followed by 500 mg every 4 hours for 24 hours.

Corticosteroid Treatment: To reduce potential edema response during drug administration, dexamethasone treatment will be administered: Subsequent doses with VB-111: 10 mg will be administered 30 minutes prior to dosing, followed by 4 mg×2/day for 3 days post dosing. Further corticosteroid treatment will be administered at Investigator's discretion. If subjects begin the study already on steroids, all efforts should be made by the Investigator not to change the steroid dose within 5 days of disease assessment, unless clinically warranted. A decision to continue the steroids or to begin tapering after this period of time is at the discretion of the Investigator.

Bevacizumab Administration:

Bevacizumab will be administered by infusion at a dose of 10 mg/kg before VB-111 on dosing days. The rate of infusion shall be according to the package insert for bevacizumab: The initial bevacizumab dose should be delivered over 90 minutes as an IV infusion following chemotherapy. If the first infusion is tolerated, the second infusion may be administered over 60 minutes. If the 60-minute infusion is tolerated, all subsequent infusions may be administered over 30 minutes.

Study Drug Administration:

Infusion will be done according to the operation manual. Prior to infusion, the saline should be brought to room temperature. The vials should be opened in a biological safety cabinet and injected into normal saline for infusion according to the operation manual. The final solution for administration should be administered not more than 90 minutes after preparation. VB-111 will be infused to the patient at the relevant dosage according to the patient's weight, as detailed in the Operations Manual. For patients less than 50 Kg of weight, a dose of $3\times10^{12}$ or $1\times10^{13}$ VPs will be reduced by 30%. The intravenous infusions of diluted VB-111 should be administered at 1 ml/minute or 3 mL/minute ($1\times10^{13}$ VPs only).

Up to 8 Hours Following the Initial Combination of VB-111 and Bevacizumab:

Laboratory Analyses: Biodistribution: Blood sample will be collected for VB-111 adenovirus DNA level expression determinations at the following time points:

0 (Prior to dosing, see above)

At end of infusion

3±0.5 hours

6±0.5 hours

Angiogenic Biomarker/Cytokine Samples: Blood samples will be collected at 6 hours post dose for:

Levels of von Willebrand factor (vWF) and TNFα (optional).

In addition, blood samples for TNF, sTNFRI, sTNFRII, VEGF, FGF, IL-6, IL-8, E-selectin, ICAM-1

Vital Signs: The vital signs (systolic and diastolic blood pressure, peripheral heart rate, body temperature, respiration rate) will be recorded at 30 and 60 minutes after dosing and at 4 and 6 hours post dosing, and/or upon disappearance of any adverse event, whichever comes first.

Adverse Events: Full supportive measures will be employed for all patients with an adverse event. All adverse events occurring following drug administration will be documented in the case report forms (CRFs), together with the intensity, the therapeutic measures applied, the outcome and the relationship to the investigational drug. Related adverse events will be followed through resolution. Unrelated adverse events will be followed through resolution or end of study.

Concomitant Medications: There is no restriction on concomitant medication, besides the drugs listed in the exclusion criteria. However, VB-111 should not be mixed with other drugs. All concomitant medication administered during the study will be documented from baseline throughout participation or Early Termination visit.

Other Laboratory Analyses: Laboratory samples drawn in response to a clinically significant event will be documented as unscheduled laboratory evaluations. In the event of clinically relevant abnormal laboratory values, the tests will be followed-up until the values have returned to within normal range and/or an adequate explanation of the abnormality is found. All such laboratory investigations will be performed at the study site, except for distribution assessments, which will be sent to an Independent Central Laboratory. Should any of these results require confirmation, re-testing will be performed in the same hospital laboratory where possible. Laboratory accreditation certificates and normal reference ranges must be provided for each hospital laboratory.

Follow Up Cohort 3-4 Extension Phase:

Bi-Weekly Treatment with Bevacizumab

Bevacizumab will be administered according to standard of care practices bi-weekly. During the visits to the clinic to receive this treatment, the subject should be seen by the Investigator to assess safety.

Bevacizumab Administration

Bevacizumab will be administered by infusion at a dose of 10 mg/kg according to standard of care practices.

Adverse Events: Full supportive measures will be employed for all patients with an adverse event. All adverse events occurring following drug administration will be documented in the case report forms (CRFs), together with the intensity, the therapeutic measures applied, the outcome and the relationship to the investigational drug. Related adverse events will be followed through resolution. Unrelated adverse events will be followed through resolution or end of study.

Concomitant Medications: There is no restriction on concomitant medication, besides the drugs listed in the exclusion criteria. However, VB-111 should not be mixed with other drugs. All concomitant medication administered during the study will be documented from baseline throughout participation or Early Termination visit.

Other Laboratory Analyses: Laboratory samples drawn in response to a clinically significant event will be documented as unscheduled laboratory evaluations. In the event of clinically relevant abnormal laboratory values, the tests will be followed-up until the values have returned to within normal range and/or an adequate explanation of the abnormality is found. All such laboratory investigations will be performed at the study site, except for distribution assessments, which will be sent to an Independent Central Laboratory. Should any of these results require confirmation, re-testing will be performed in the same hospital laboratory where possible. Laboratory accreditation certificates and normal reference ranges must be provided for each hospital laboratory.

28 Days Following Initial Combination Treatment

One month following the initial combination treatment, each patient will be required to return to the clinic in a fasting state, for the following evaluations:

Vital signs: Vital signs (supine systolic and diastolic blood pressure, peripheral heart rate, body temperature, respiration rate) will be recorded.

Laboratory Analyses: Blood sample will be collected for the following evaluations:

Hematology: hemoglobin, complete blood count, INR, PT, and activated PTT: In the case of PTT prolongation above ULN, please refer to Section 6.2 Dose Delay/Modification for further instructions.

Chemistry: electrolytes, creatinine and blood urea nitrogen, bilirubin, alkaline phosphatase, ALT and AST, calcium, total protein and albumin Laboratory samples drawn in response to a clinically significant event will be documented as unscheduled laboratory evaluations.

Urine sample will be collected for:
Routine urinalysis
Dipstick for Proteinuria
No dose modifications for grade 1/2 events
Grade 3- (UPC>3.5, urine collection >3.5 g/24 hr, or dipstick 4+): Hold bevacizumab treatment until ≤Grade 2, as determined by either UPC ratio ≤3.5 or 24 hr collection ≤3.5 g
Grade 4 (nephrotic syndrome): Discontinue bevacizumab Adverse Events: At the follow up visit to the investigator, the patient will be questioned about possible adverse events which may have occurred from the day of last visit. Full supportive measures will be employed for all patients with an adverse event. All adverse events will be documented in the case report forms (CRFs), together with the intensity, the therapeutic measures applied, the outcome and the relationship to the investigational drug. Related adverse events will be followed through resolution. Unrelated adverse events will be followed through resolution or end of study.

Concomitant Medications: At the follow up visit to the investigator, the patient will be questioned about possible medications which may have been taken from the day of last visit. All concomitant medications will be recorded with generic name, indication, dosage, units, frequency, start and stop dates.

Study Completion/Early Termination

Subjects in Cohorts 3 and 4 will continue to receive VB-111 every 2 months, provided that they continue to be stable. Once subjects experience disease progression, they may receive combination treatment with VB-111 or they will return to the clinic for a final study visit. In addition, if subjects withdraw consent or it is determined by the Investigator that the subject should not continue in the study, the subject will return for an Early Termination Visit. Subjects will continue to be followed every 2-3 months as part of their Standard of Care follow up. VBL may request data on these subjects (e.g. MRI scans, other anti-cancer treatments).

Subjects who are no longer seen for standard of care visits at the site should be contacted by telephone every 2-3 months to follow up on survival and for information regarding further treatment for glioblastoma. Follow up will continue until the patient expires.

Duration of Study

Cohorts 1-2: Each patient will be administered with a single injection of VB-111 and will be followed with regularly scheduled visits and evaluations for a period of 6 months after dosing or until progression or study withdrawal and then followed for survival by a post study follow-up telephone contact every 2 months. Additionally, surveillance MRIs will be performed every 2 months until 1 year post dosing, and then every 3 months until 2 years post dosing, Patients can decide to withdraw from study at any time. Patients who withdraw prior to day 168±7 should be requested to return to the clinic for an early termination visit and should still be contacted and questioned about AEs. (Patients who withdraw after day 168 will not be considered early terminations.) All AEs, irrespective of whether related or not to the disease, will be documented in the patient's record and CRF.

Cohorts 3 and 4: Subjects will be screened 3 weeks before the initial dose (D0) and will receive VB-111 every 2 months through disease progression. Following disease progression, routine Standard of Care will be performed; patients will be followed for disease status updates and survival every 2-3 months.

Exploratory Assessments

Optional Biopsy Samples; Biopsies of brain tissue (preferably fresh frozen samples) may be collected for further testing by VBL as part of a clinically indicated procedure at any time in the study. If a sample of brain tissue is collected, a blood sample for transgene analysis should be collected on the same day.

Circulating Endothelial Cells (CECs); Optionally, CECs may be collected and analyzed as a biomarker for angiogenesis via Flow Cytometry at any time in the study, if the subject consents and the site has local capability to perform such testing.

Additional Exploratory Testing: Samples collected for plasma, serum, tissue throughout the study will be stored by VBL or its designee for up to 15 years for exploratory testing to better understand the impact, potential response and toxicity of VB-111.

Expected Adverse Events/Dose Modifications

Expected Adverse Events

Pre-Clinical Studies

VB-111 caused minimal toxicity in preclinical toxicology studies in mice. Mild anemia, mild thrombocytopenia, mild leukocytosis, splenomegaly, and bone marrow hyperplasia were observed. Transient liver enzyme elevations with no correlation with clinical pathology were also observed.

Adenovirus Vectors and Anti-Angiogenic Agents

The administration of adenovirus vectors systemically has been well tolerated. Flu-like symptoms (fever, fatigue, rigors, nausea, and/or vomiting) are the most common adverse events. The majority of intravenously injected adenovirus particles are sequestered by the liver, which in turn causes an inflammatory response characterized by acute transaminitis and vascular damage.

The administration of anti-angiogenic agents systemically has also been well tolerated. The major predicted adverse effects have been wound healing disorders, bleeding and thromboembolic events. Hypertension and proteinuria have also been reported with antiangiogenic therapy.

Expected Adverse Events with Bevacizumab

Gastrointestinal (GI) perforation

Serious and sometimes fatal GI perforation occurs at a higher incidence in bevacizumab-treated patients compared to controls The incidences of GI perforation ranged from 0.3% to 2.4% across clinical studies Discontinue bevacizumab in patients with GI perforation Surgery and Wound Healing Complications The incidence of wound healing and surgical complications, including serious and fatal complications, is increased in bevacizumab-treated patients Do not initiate bevacizumab for at least 28 days after surgery and until the surgical wound is fully healed. The appropriate interval between termination of bevacizumab and subsequent elective surgery required to reduce the risks of impaired wound healing/wound dehiscence has not been determined Discontinue bevacizumab at least 28 days prior to elective surgery and in patients with wound healing complications requiring medical intervention Hemorrhage Severe or fatal hemorrhage, including hemoptysis, GI bleeding, hematemesis, central nervous system hemorrhage, epistaxis, and vaginal bleeding, occurred up to 5-fold more frequently in patients receiving bevacizumab. Across indications, the incidence of grade ≥3 hemorrhagic events among patients receiving bevacizumab ranged from 1.2% to 4.6%

Do not administer bevacizumab to patients with serious hemorrhage or recent hemoptysis (≥½ tsp of red blood)

Discontinue bevacizumab in patients with serious hemorrhage (ie, requiring medical intervention)

Additional Serious Adverse Events

Additional serious and sometimes fatal adverse events with increased incidence in the bevacizumab-treated arm vs control included Non-GI fistula formation (≤0.3%)
Arterial thromboembolic events (grade ≥3, 2.6%)
Proteinuria (nephrotic syndrome, <1%)

Additional serious adverse events with increased incidence in the bevacizumab-treated arm vs control included Hypertension (grade 3-4, 5%-18%)
Reversible posterior leukoencephalopathy syndrome (RPLS) (<0.1%)

Infusion reactions with the first dose of bevacizumab were uncommon (<3%), and severe reactions occurred in 0.2% of patients Inform females of reproductive potential of the risk of ovarian failure prior to starting treatment with bevacizumab Most common adverse reactions observed in bevacizumab patients at a rate >10% and at least twice the control arm rate were epistaxis, headache, hypertension, rhinitis, proteinuria, taste alteration, dry skin and rectal hemorrhage.

Dosing Delays/Dose Modification

For subjects participating in multiple dose cohorts, dosing may be delayed in the following situations:

Subjects who experienced a VB-111 drug related adverse event, and are scheduled for a repeat dose, the repeat dose will be delayed until the severity of the event is no more than CTCAE Grade 1.

Subjects who experienced a prolongation of aPTT and are scheduled for a repeat dose, the repeat dose will be delayed until the PTT has returned to within 20% of the baseline value, whether any positive LAC or APLA test has normalized or not. Borderline cases may be discussed with the sponsor on a case by case basis.

Subjects with clinically significant thrombotic or bleeding events related to a prolonged PTT should not receive additional doses of VB-111.

In case of PTT prolongation above ULN, blood should be drawn for lupus anticoagulant (LAC) and for anti-phospholipid antibody (IgG and IgM for beta-2-GP-1 and anticardiolipin). Patients with prolonged aPTT should not receive VB-111 until the abnormal laboratory values return to within 20% of the baseline value, whether any positive LAC or APLA test has normalized or not. If repeat test for LAC/APLA remains positive, it must be repeated every 12 weeks (from the initial positive test) until it returns to normal.

During DLT monitoring. To comply with protocol restrictions regarding 14 day observation periods between patients Patients will be assigned to Cohort 3 (single or multiple doses of $3\times10^{12}$ VPs) or Cohort 4 (multiple doses of $1\times10^{13}$ VPs). No dose modification will be permitted for this trial. However, VB-111 will be infused to the patient at the relevant dosage according to the patient's weight, as detailed in the Operations Manual. For patients less than 50 Kg of weight, a dose of $3\times10^{12}$ or $1\times10^{13}$ VPs will be reduced by 30%. The intravenous infusions of diluted VB-111 should be administered at 1 ml/minute or 3 mL/minute ($1\times10^{13}$ VPs only).

Correlative/Special Studies

Distribution: For distribution assessment, blood samples will be collected from all patients according to the operation manual. Testing of these samples for Adenovirus and VB-111 transgene level determination will be conducted at the maximal tolerated dose group or the highest dose cohort. Distribution will be assessed by determination of levels of viral DNA and transgene by Q-PCR and Q-RT-PCR respectively in the blood, at pre-determined time points following dosing. Samples will be collected for all patients at all pre-defined time points. Samples found with non-detectable levels of viral DNA following dosing will not be tested for levels of the transgene and will not be evaluated for later time points.

Antibodies: Serum samples will be collected for analysis of levels of antibodies to the adenovirus according to the Operation Manual.

Procedures for Handling Blood Samples: Refer to the Operation Manual for instructions for a full description on Procedures for Safety Samples and Procedures for Q-PCR and Q-RT-PCR Determination.

Measurement of Effect

Tumor response will be assessed, using contrast and non-contrast brain magnetic resonance imaging (MRI) with assessment based on the RANO criteria, until progression of disease (local and central independent radiology review). For patients who do not progress or die, PFS will be censored at the time of initiation of alternative anticancer therapy, date of last radiologic assessment, or time of last contact.

Definitions

Response and progression will be evaluated in this study using the new international criteria proposed by the Response Assessment in Neuro-Oncology (RANO) Working Group [JCO, Updated Response Assessment Criteria for High-Grade Gliomas: Response Assessment in Neuro-Oncology (RANO) Working Group, in press] Note: Lesions are either measurable or non-measurable using the criteria provided below. The term "evaluable" in reference to measurability will not be used because it does not provide additional meaning or accuracy.

Measurable Disease: Measurable disease is defined as bidimensionally contrast-enhancing lesions with clearly-defined margins by MRI, with two perpendicular diameters of at least 10 mm, visible on 2 or more axial slices which are preferably at most 5 mm apart with 0 mm skip. In the event the MRI is performed with thicker slices, the size of a measurable lesion at baseline should be two times the slice thickness. In the event there are inter-slice gaps, this also needs to be considered in determining the size of measurable lesions at baseline.

Measurement of tumor around a cyst or surgical cavity is problematic. In general, such lesions should be considered non-measurable unless there is a nodular component measuring at least 10 mm in diameter. The cystic or surgical cavity should not be measured in determining response.

All tumor measurements must be recorded in millimeters (or decimal fractions of centimeters).

Non-measurable Disease: This is defined as either unidimensionally measurable lesions, masses with margins not clearly defined, or lesions with maximal perpendicular diameters <10 mm.

Target Lesions: All measurable lesions up to a maximum of five lesions should be identified as target lesions and recorded and measured (sum of the products of the perpendicular diameters) at baseline. Target lesions should be selected on the basis of their size (lesions with the longest diameters) and their suitability for accurate repeated measurements by imaging techniques. Occasionally, the largest lesions may not be suitable for reproducible measurements and the next largest lesions which can be measured reproducibly should be selected.

Non-target Lesions: For patients with recurrent disease who have multiple lesions of which only one or two are increasing in size, the enlarging lesions should be considered the target lesions for evaluation of response. The other lesions will be considered non-target lesions and should also be recorded.

Rarely, unequivocal progression of a non-target lesion requiring discontinuation of therapy, or development of a new contrast-enhancing lesion may occur even in the setting of stable disease (SD) or partial response (PR) in the target lesions. These changes would qualify as progression.

Non-target lesions also include measurable lesions that exceed the maximum number of 5. Measurements of these lesions are not required but the presence or absence of each should be noted throughout follow-up.

Guidelines for Evaluation of Measurable Disease

All measurements should be taken and recorded in metric notation using a ruler or calipers. All baseline evaluations should be performed within 72 hours before the beginning of the treatment.

Conventional MRI is required, CT is not acceptable. The same method of assessment and the same technique should be used to characterize each identified and reported lesion at baseline and during follow-up.

These techniques should be performed with cuts of 10 mm or less in slice thickness contiguously. The MRIs will be evaluated both locally and centrally by a core lab.

Response Criteria

Evaluation of Target Lesions: Complete Response (CR): Requires all of the following:
Complete disappearance of all enhancing measurable and non-measurable disease sustained for at least 4 weeks
No new lesions
Stable or improved non-enhancing (T2/FLAIR) lesions
Patients must be off corticosteroids
Stable or improved clinically
Partial Response (PR): Requires all of the following:
≥50% decrease compared to baseline in the sum of products of perpendicular diameters of all measurable enhancing lesions sustained for at least 4 weeks
No progression of non-measurable disease
No new lesions
Stable or improved non-enhancing (T2/FLAIR) lesions on same or lower dose of corticosteroids compared to baseline scan
The corticosteroid dose at the time of the scan evaluation should be no greater than the dose at time of the baseline scan
Stable or improved clinically
Stable Disease (SD): Requires all of the following:
Does not qualify for complete response, partial response, or progression
Stable non-enhancing (T2/FLAIR) lesions on same or lower dose of corticosteroids compared to baseline scan. In the event that the corticosteroid dose has been increased, the last scan considered to show stable disease will be the scan obtained when the corticosteroid dose was equivalent to the baseline dose
Stable clinically
Progression: Defined by any of the following:
≥25% increase in the sum of products of perpendicular diameters of enhancing lesions compared to the smallest tumor measurement obtained either at baseline (if no decrease) or best response, on stable or increasing doses of corticosteroids
Significant increase in T2/FLAIR non-enhancing lesion on stable or increasing doses of corticosteroids compared to baseline scan or best response following initiation of therapy, not due to co-morbid events (e.g. radiation therapy, demyelination, ischemic injury, infection, seizures, post-operative changes, or other treatment effects).
Any new lesion
Clear clinical deterioration not attributable to other causes apart from the tumor (e.g. seizures, medication side effects, complications of therapy, cerebrovascular events, infection, etc.) or changes in corticosteroid dose
Failure to return for evaluation due to death or deteriorating condition
Clear progression of non-measurable disease
If there is uncertainty regarding whether there is progression, the patient may continue on treatment and remain under close observation. If subsequent evaluations suggest that the patient is progressing, the date of progression should be the time point at which this issue was initially raised.

These RANO Response Criteria are also summarized in the following table:

TABLE 6

Summary of the RANO Response Criteria

| | CR | PR | SD | PD# |
|---|---|---|---|---|
| T1-Gd + | None | ≥50% decrease | <50% decrease-<25% increase | ≥25% increase* |
| T2/FLAIR | Stable or decrease | Stable or decrease | Stable or decrease | Increase* |
| New Lesion | None | None | None | Present* |
| Corticosteroids | None | Stable or decrease | Stable or decrease | NA |
| Clinical Status | Stable or increase | Stable or increase | Stable or increase | Decrease* |
| Requirement for Response | All | All | All | Any* |

CR = complete response; PR = partial response; SD = stable disease; PD = progressive disease
Progression occurs when any of the criteria with * is present
NA: Increase in corticosteroids alone will not be taken into account in determining progression in the absence of persistent clinical deterioration Confirmatory Measurement/Duration of Response
Confirmation To be assigned a status of PR or CR, changes in tumor measurements must be confirmed by repeat assessments that should be performed 4 weeks after the criteria for response are first met.

Duration of Overall Response

The duration of overall response is measured from the time measurement criteria are met for CR or PR (whichever is first recorded) until the first date that recurrent or progressive disease is objectively documented (taking as reference for progressive disease the smallest measurements recorded since the treatment started).

The duration of overall CR is measured from the time measurement criteria are first met for CR until the first date that recurrent disease is objectively documented.

Duration of Stable Disease

Stable disease is measured from the start of the treatment until the criteria for progression are met, taking as reference the smallest measurements recorded since the treatment started.

Statistical Considerations

Study Design

Objectives: To evaluate the safety, tolerability, and efficacy of single and multiple doses of VB 111 ($1\times10^{12}$, $3\times10^{12}$, $1\times10^{13}$ viral particles [VPs]) in patients with recurrent GBM; to evaluate the distribution of VB-111 after single and multiple IV infusions and the level of antibodies to the adenovirus vector and transgene Up to 90 subjects are anticipated to enroll in this study, with up to 29 subjects at the $3\times10^{12}$ VP dose level, and up to 49 subjects at the $1\times10^{13}$ VP dose level. Cohorts 1-2 will enroll up to 6 patients in each. Cohort 3 will be conducted according to the Simon's 2 step method.

Step one will include the first 10 evaluable patients at the $1\times10^{13}$ VP dose level or MTD.

For efficacy analysis, evaluable patients will be defined as those who received at least one repeat dose of $1\times10^{13}$ VPs or of MTD, or patients who progressed sooner than 2 months after an initial dose of $1\times10^{13}$ VPs (from cohort 3 or 4).

A subject will be considered to have a response if s/he is either alive and progression free at 6 months or has at least a partial tumor response according to Rano criteria within 6 months post dosing. If less than 2 responses are observed in the step 1 subjects, step 2 will be halted, otherwise, an additional 19 subjects will enroll in step 2.

Cohort 4 will enroll up to 49 subjects.

It is anticipated that at least 29 patients enrolled in Cohorts 3 or 4 will be evaluable after enrolling into Cohort 3-4 EXT. Based on historical information, it is anticipated that this sample will allow preliminary assessment of safety and efficacy of this regimen for the treatment of recurrent GBM.

The following study stopping rules for halting the study will be applied:
  If 3 out of 6 subjects in the Cohorts 1 & 2 experience drug related DLT (or 5 out of 9 or 6 out of 12);
  If 2 of the subjects in Cohort 1 experience a DLT;
  If ANY death occurs within two weeks after the product is given, except death due to disease progression or clearly unrelated to study drug. Enrollment will be temporarily suspended for an ad hoc, emergency IDMC meeting to review the case and make a recommendation if enrolment can be reinstated.

Safety and Tolerability Endpoints

To evaluate the safety and tolerability of single and multiple doses of VB-111 ($1\times10^{12}$, $3\times10^{12}$, $1\times10^{13}$ VPs) the following safety endpoints will be assessed throughout the study:
  Adverse events will be recorded on an ongoing basis for the whole duration of the study. Adverse events will be assessed for seriousness, relatedness to study drug, and severity (According to CTCAE 4.0).
  Vital signs will be recorded at screening, prior to each dosing, 30 and 60 minutes, 4 and 6 hours after the first dosing and at all follow up visits.
  Physical examinations will be conducted in Cohorts 1-2 at screening, baseline, Days 14, 28, 56, 84, 112, 140 and Day 168. In Cohorts 3-4, a physical exam will be conducted at screening/baseline, before each dosing, and the study completion/early termination.
  12-lead ECG will be obtained in Cohorts 1-2 at screening, prior to dosing, Day 28 and Day 168 (or ET). In Cohorts 3-4, an ECG will be obtained at screening/baseline, the Day 56 visit, and the study completion/early termination visit.
  Safety laboratory assessment (blood hematology, chemistry, and urinalysis) will be conducted at screening, prior to dosing, and at all patient visits.

Primary Efficacy Endpoint: To evaluate the efficacy of single or multiple doses of VB-111 ($1\times10^{12}$, $3\times10^{12}$, $1\times10^{13}$ VPs) in recurrent GBM subjects, 6 months progression free survival (PFS) will be assessed, defined as proportion of subjects who are progression free at 6 months from enrollment. In another aspect, overall survival will be assessed as the primary efficacy endpoint and 6-months PFS will be assessed as a secondary efficacy endpoint. Overall survival is defined as the time from enrollment until death from any cause. Patients will be followed for survival status after completion or removal from the study for progression or toxicity, and will be included in the PFS and OS analyses.

Secondary Efficacy Endpoints: To evaluate the efficacy of single or multiple doses of VB-111 ($1\times10^{12}$, $3\times10^{12}$, $1\times10^{13}$ VPs), or multiple doses of VB-111 together with bevacizumab in recurrent GBM subjects the following secondary efficacy endpoints will be assessed:
  In one aspect, secondary efficacy endpoints will be assessed by Overall survival (OS): Overall survival is defined as the time from enrollment until death from any cause. Patients will be followed for survival status after completion or removal from the study for progression or toxicity, and will be included in the PFS and OS analyses.
  In another aspect, secondary efficacy endpoints will be assessed by Progression Free Survival (PFS): Progression free survival is defined as the time from enrollment until objective tumor progression, assessed according to Response Assessment in Neuro-Oncology (RANO) Working Group (see details in section 8.3.1).
  Progression Free Survival at 6 months (PFS-6) is defined as the proportion of subjects who are progression free at 6 months from enrollment
  Event free survival (EFS): Event-free survival is defined as measurement from the date of enrollment until termination of treatment due to toxicity, disease progression, relapse, or death from any cause.
  Tumor response: based on MRI, assessed according to Response Assessment in Neuro-Oncology (RANO) Working Group (see details in section 8.3.1)

Power and Sample Size Considerations

In one embodiment, the primary efficacy endpoint is Overall Survival. Using data presented in Friedman et al., "Bevacizumab alone and in combination with irinotecan in recurrent glioblastoma," J. Clin Oncol. 27(28):4733-40 (2009), OS in the bevacizumub group at 12 months is 25%. Based on preliminary data, it is expected that the 12 month overall survival rate in the VB-111 group will be approximately 50% (hazard ratio=0.5). Assuming a proportional hazards model, a sample size of 45 patients in the VB-111 group generating approximately 23 events, a 0.05 level two-sided Logrank test will have 80% power to detect a difference of survival curves. The final analysis will compare Kaplan Meier survival curves of BEV (based on Friedman et al data) vs. VB-111 survival data using the Log-rank Test (Piantadosi 2005).

Alternatively, this study will assess efficacy endpoints using a two-stage Simon design. In this study response is defined by either 6 months PFS or at least a partial tumor response. With a minimum of 10 patients and a maximum of 29 patients the null hypothesis that the true proportion of PFS-6 is at most 10% vs the alternative hypothesis that the 6 month PFS is at least 30%:
H0: PFS-6<=10%
H1: PFS-6>=30%

This has a significance level of 5% when the true proportion is 10% and 80% power when the true proportion is at least 30%.

Unless toxicity is encountered or the study is stopped at the interim analysis, this study anticipates accruing between 3-6 subjects in Cohort 1, 3-6 subjects in Cohort 2, up to 29 subjects in Cohort 3 and up to 49 subjects in Cohort 4.

It is anticipated that at least 29 patients enrolled in Cohorts 3 or 4 will be evaluable after enrolling into Cohort 3-4 EXT. Based on historical information, it is anticipated that this sample will allow preliminary assessment of safety and efficacy of this regimen for the treatment of recurrent GBM.

Statistical Methods

All data collected will be summarized and presented. Continuous variables will be described as the mean, median, standard deviation and range of n observations. Categorical data will be described with contingency tables including frequency and percent. Individual subject listings will be generated and presented.

Confidence intervals will be calculated at the (two-sided) 95% level of confidence (except for the primary efficacy and safety endpoints, which will be 99% and 95% (one-sided) respectively.

All patients meeting the eligibility criteria who have signed a consent form and have received VB-111 will be considered evaluable for safety analysis.

Statistical descriptions and analyses will be carried out using SAS statistical analysis software (SAS Institute, Inc., Cary, N.C., USA).

Demographic Parameters

Demographic parameters including sex, age, height and weight will be summarized overall and by treatment group.

Safety and Toxicity Analyses

Adverse events monitoring and clinical findings will be used to assess safety.

AEs will be categorized by SOC and Preferred Terms using the MedDRA dictionary. The incidence of AEs as well as the severity and relationship to study drug will be presented. As per NCI CTCAE Version 4.0, the term toxicity is defined as adverse events that are classified as either possibly, probably, or definitely related to study treatment. The maximum grade for each type of toxicity will be recorded for each patient and will be used for reporting. Frequency tables will be reviewed to determine toxicity patterns. In addition, all adverse event data graded as 3, 4, or 5 and classified as either "unrelated or unlikely to be related" to study treatment in the event of an actual relationship developing will be reviewed.

Serious adverse events will be similarly summarized.

Infusional adverse events will also be summarized by both the investigator's and the sponsor's assessment of causality.

The number and proportion of patients who have one or more AEs will be presented as well.

Clinical findings will include evaluation of physical examinations, vital signs and laboratory test results, concomitant medications, and withdrawals/terminations. These findings will be summarized by dose group. Continuous variables will be described as the mean, median, standard deviation, and range of n observations. Categorical data will be described with contingency tables including frequency and percent.

Efficacy Analyses

Overall survival (OS) is defined as the time from the first date of study treatment until the date of subject death from any cause. For subjects who have not died, survival data will be censored at the subject's last known alive date. The Kaplan-Meier method will be used to estimate the distribution and median OS for subjects treated at the MTD level.

Progression Free Survival (PFS) is defined as the time from the first date of study treatment to documented disease progression, or to death from any cause whichever occurs earlier. Tumor response and disease progression will be assessed by the investigator according to RANO criteria. The proportion of subjects who have 6 months PFS will be presented for each treatment group. For patients who do not progress or die, PFS will be censored at the time of initiation of alternative anticancer therapy, date of last tumor assessment, or time of last contact. The Kaplan-Meier method will be used to estimate the distribution and median PFS for subjects treated at the $3 \times 10^{12}$ and $1 \times 10^{13}$ VPs levels, or multiple doses of VB-111 together with bevacizumab.

Event Free Survival is defined as measurement from the date of enrollment until termination of treatment due to toxicity, disease progression, relapse, or death from any cause. The Kaplan-Meier method will be used to estimate the distribution and median of event free survival for subjects treated at the MTD level.

Tumor Response is defined according the RANO Response criteria. See Section 8.3 for definitions of Complete Response, Partial Response, Stable Disease and Progression. Tumor response will be assessed at Screening, prior to dosing, Days 14, 28, 56, 84, 112, 140 (Cohorts 1-2 only) and 168 and every 2 months thereafter, using contrast and non-contrast brain magnetic resonance imaging (MRI). The frequency and percentage of tumor response will be presented by timepoint and treatment group. For Cohorts 3-4, and the extension, tumor response will be assessed at Screening, prior to dosing, Days 28, 56, 84, 112, and every 2 months thereafter. Following this protocol amendment (Version 7.0), scans will be performed every 2 months from initial dose.

Biodistribution

The Biodistribution of VB-111 in blood will be presented.

Number of Patients Planned to be Enrolled

Based on the study design it is estimated that a maximum of 90 eligible (3-6 in each of cohorts 1 and 2, up to 29 in cohort 3, and up to 49 in Cohort 4) with recurrent GBM cancer are needed, 29 evaluable patients are required for efficacy assessment.

Criteria for Termination of the Trial

The sponsor reserves the right to terminate the study early for administrative (e.g. center not complying with GCP) or safety reasons as described under 4.2.

Procedure for Accounting for Missing, Unused and Spurious Data

Missing data will be indicated in the listings, but excluded from all descriptive analyses. All data will be listed, including otherwise unused data. Spurious data will be identified as such, wherever possible.

Selection of Patients to be Included in the Analyses

The Full Analysis Set will consist of all patients enrolled who receive study medication. The biodistribution subset will consist of all patients for whom a VB-111 profile is obtained.

Interim Analyses:

An interim analysis will be performed after enrollment of 10 evaluable patients (as defined above) who have reached day 168 time point (6 months) or have discontinued prior to that, The results of the interim analysis will determine whether the remainder of the patients will be enrolled into cohort 4 in order to complete the study.

Example 3

Methods:

VB-111 was administered as a single intravenous infusion at escalating doses from $1\times10^{12}$ (cohort 1) to $3\times10^{12}$ (cohort 2) viral particles (VPs), followed by repeat doses of $3\times10^{12}$ or $1\times10^{13}$ every 2 months (cohorts 3-4). Assessments included safety, pharmacokinetics, tumor response according to RANO criteria and overall survival.

Results:

Twenty eight patients aged 26-74 years at 3 medical centers in the US received up to 8 repeat doses of VB-111. The median overall survival was 360 [range: 70-574] and 266 days [range: 28-664] for patients receiving at least one dose of $1\times10^{13}$ VPs (high dose) vs subjects who received lower doses, respectively (p NS). Progression free survival was 87 vs 55 days for patients who received high dose and for lower doses, respectively (p=0.01). Median follow-up was 232 days. Three patients had a partial response (PR) at 82, 86 and 408 days post initial VB-111 dosing. Twenty one of the patients who progressed after VB-111 treatment received bevacizumab off study; 7 of the 15 evaluable patients (47%) had a PR compared to a 30% expected PR rate according to literature. VB-111 was safe and well tolerated, 53 adverse events were reported, 14 were classified as possibly related to VB-111. All events were of CTCAE grade 1-2 except one grade 3 pulmonary embolism (PE). There were no study related deaths. One patient developed peri-tumoral edema post dosing, which resolved with corticosteroid therapy. Events occurring in more than 10% of the patients included headache and fatigue.

As this study continued, additional subjects with progressive disease were treated with bevacizumab and the study data were recalculated accordingly. Twenty three of the subjects who had progressive disease (PD) on VB-111 treatment received bevacizumab off study; 6 of the 15 evaluable subjects (40%) had a partial response (PR) compared to 30% expected according to literature. The data are provided in the Table below.

TABLE 7

Post-VB-111 Response to bevacizumab

| Subject ID | Exposure to bevacizumab | Best Response* |
|---|---|---|
| 60-001 | Yes | PD |
| 60-002 | Yes | PD |
| 60-003 | Yes | SD |
| 60-004 | Yes | SD |
| 60-005 | Yes | PR |
| 61-001 | Yes | Unknown |
| 61-002 | Yes | Unknown |
| 61-003 | Yes | SD |
| 61-004 | Yes | Unknown |
| 61-005 | Yes | Unknown |
| 62-002 | No | N/A |
| 62-003 | Yes | PR |
| 62-004 | Yes | PR |
| 62-005 | Yes | Unknown |
| 62-006 | Yes | SD |
| 62-007 | Yes | PD |
| 62-008 | Unknown | Unknown |
| 62-009 | Yes | Unknown |
| 62-010 | Subject still stable on VB-111 | |
| 62-011 | Yes | PD |
| 62-012 | Yes | Unknown |
| 62-013 | Yes | PR |
| 62-014 | Unknown | Unknown |
| 62-015 | Yes | SD |
| 62-016 | Yes | PR |
| 62-017 | Yes | PR |
| 62-018 | Yes | Unknown |
| 62-019 | Subject still stable on VB-111 | |

*PD, progressive disease; PR, partial response; SD, stable disease

Figure 2:
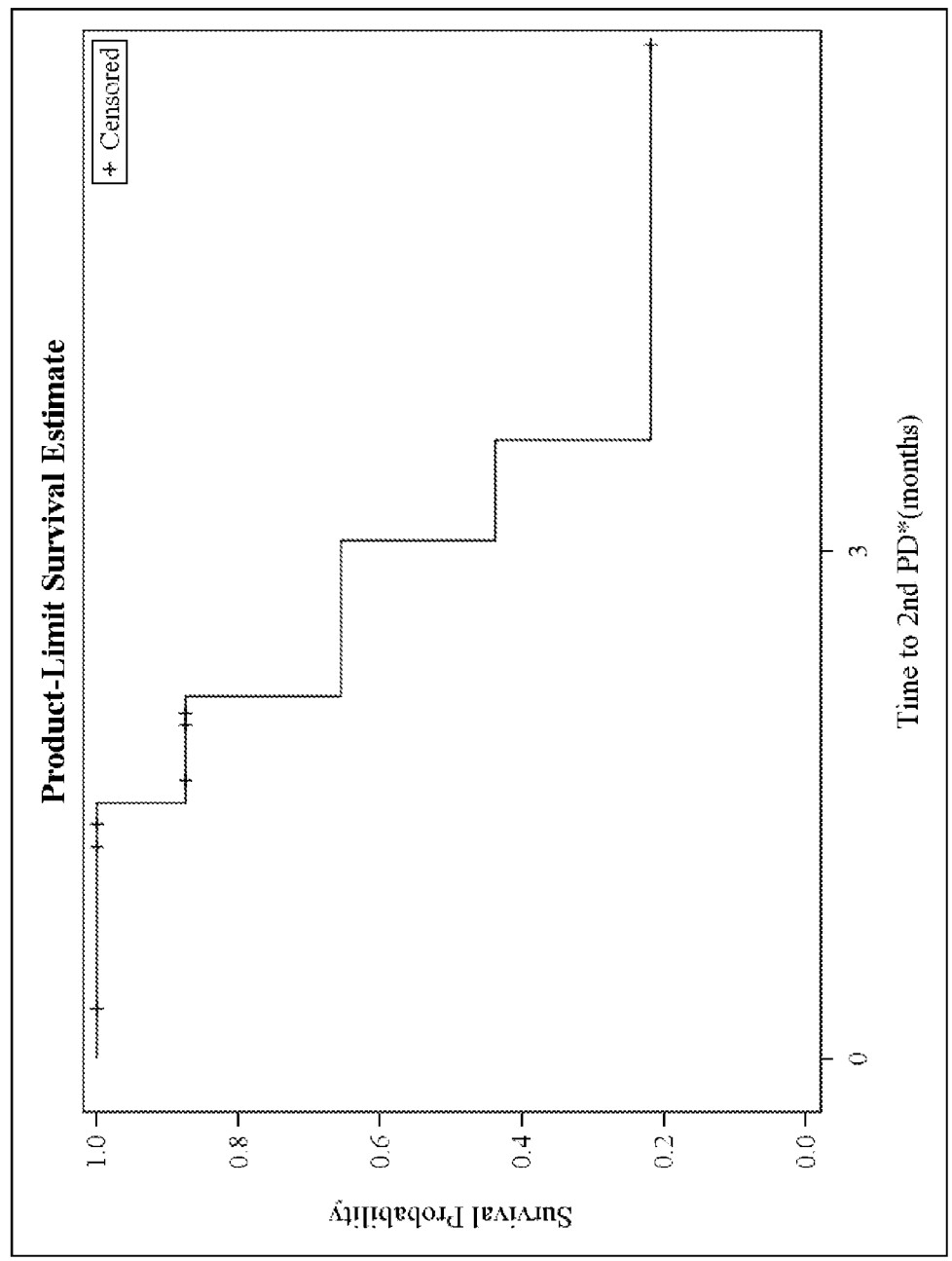
FIG. 2 shows the time for glioblastima disease progression from first relapse to second relapse in patients receiving a combination therapy regimen of an adenovirus comprising a FAS-chimera gene operably linked to an endothelial cell-specific promoter (e.g., VB-111) and bevacizumab (BEV).
Figure 3:
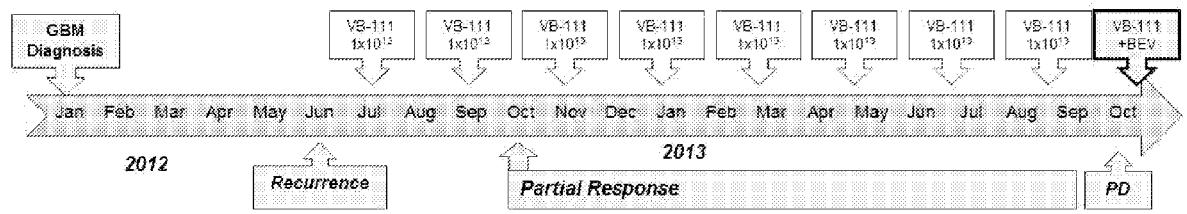
FIG. 3 shows an example of a patient who was treated with a combination regimen of an adenovirus comprising a FAS-chimera gene operably linked to an endothelial cell-specific promoter (e.g., VB-111) and bevacizumab (BEV) upon glioblastoma disease progression.

Additional patients were subsequently added to the study and the data were recalculated accordingly. Forty six patients aged 27-76 years at 4 medical centers in the US and Israel received up to 13 repeat doses of VB-111. Of these, 30 patients received the high dose ($1\times10^{13}$ VPs). There were 22 related adverse events, 19 CTCAE grade 1-2; grade 3 included pulmonary embolism, peri-tumoral edema and DVT. The median overall survival was 360 [range: 70-574] and 266 days [range: 28-664] for patients receiving at least one high dose vs. subjects who received lower doses, respectively (p NS). Progression free survival was 63 vs. 55 days for patients who received high vs. lower doses, respectively (p=0.01). Median follow-up was 232 days. Six patients had a partial response and/or prolonged disease stability (≥180 days). Tumor growth rates showed a statistically significant dose response. Eleven patients received combination therapy of up to 4 doses of VB-111 together with bevacizumab after progression on VB-111 monotherapy. Median time to second progression was 93 days. These data are shown in FIG. 2. FIG. 3 provides an example of a patient who was treated with a combination of VB-111 and bevacizumab upon disease progression. VB-111 was safe and well tolerated both as monotherapy and combined therapy.

Conclusions:

VB-111 was safe and well tolerated in patients with recurrent GBM with repeat doses of up to $1\times10^{13}$ VPs. Tumor responses were seen. Overall survival was about 3 months longer compared to historical data in recurrent GBM including standard of care anti-angiogenic agents. Data suggests that VB-111 potentiates the response to bevacizumab given at further progression.

Example 4

Administration of Multiple Doses of Ad5-PPE-1-3X-Fas-c Combined with Bevacizumab OBJECTIVE: To evaluate the safety, tolerability, and efficacy of multiple doses of VB-111 $1\times10^{13}$ viral particles (VP) in patients with recurrent GBM every 8 weeks as monotherapy, combined with bevacizumab 10 mg/Kg every 2 weeks upon progression compared to bevacizumab monotherapy in patients with recurrent GBM.

The patients in the intervention arm will first receive VB-111, followed by combination of VB-111 with bevacizumab upon progression.

In one embodiment, further efficacy of VB-111 can be observed in combination with bevacizumab even after progression on VB-111 monotherapy, since synergism may potentiate VB-111 activity and overcome drug resistance. Also, in some cases delayed response to VB-111 was observed in the patients several months after receiving VB-111. Thus, some patients may experience rapid disease progression upon study enrollment without the opportunity to respond to VB-111. The proposed regimen may provide benefit from such delayed responses.

Inclusion Criteria

First or second progression or first recurrence of Glioblastoma (according to updated RANO Criteria, see Table 8) following standard of care treatment with temozolomide and radiation;

A histologically confirmed diagnosis of GBM. Patients with surgically resectable disease at recurrence may be enrolled, even if there is no residual disease upon surgical resection. An interval of at least 4 weeks between prior surgical resection and study enrollment;

TABLE 8

Criteria for Response Assessment Incorporating MRI and Clinical Factors (From updated RANO criteria as published in Wen et al., "Updated response assessment criteria for high-grade gliomas: response assessment in neuro-oncology working group., *J Clin Oncol* 28: 1963-1972 (2010).

| Response | Criteria |
|---|---|
| Complete response | Requires all of the following: complete disappearance of all enhancing measurable and non-measurable disease sustained for at least 4 weeks; no new lesions; stable or improved non-enhancing (T2/FLAIR) lesions; patients must be off corticosteroids (or on physiologic replacement doses only); and stable or improved clinically. Note: Patients with non-measurable disease only cannot have a complete response; the best response possible is stable disease. |
| Partial response | Requires all of the following: ≥50% decrease compared with baseline in the sum of products of perpendicular diameters of all measurable enhancing lesions sustained for at least 4 weeks; no progression of non-measurable disease; no new lesions; stable or improved non-enhancing (T2/FLAIR) lesions on same or lower dose of corticosteroids compared with baseline scan; the corticosteroid dose at the time of the scan evaluation should be no greater than the dose at time of baseline scan; and stable or improved clinically. Note: Patients with non-measurable disease only cannot have a partial response; the best response possible is stable disease. |
| Stable disease | Requires all of the following: does not qualify for complete response, partial response, or progression; stable non-enhancing (T2/FLAIR) lesions on same or lower dose of corticosteroids compared with baseline scan. In the event that the corticosteroid dose was increased for new symptoms and signs without confirmation of disease progression on neuroimaging, and subsequent follow-up imaging shows that this increase in corticosteroids was required because of disease progression, the last scan considered to show stable disease will be the scan obtained when the corticosteroid dose was equivalent to the baseline dose. |
| Progression | Defined by any of the following: ≥25% increase in sum of the products of perpendicular diameters of enhancing lesions compared with the smallest tumor measurement obtained either at baseline (if no decrease) or best response, on stable or increasing doses of corticosteroids*; significant increase in T2/FLAIR non-enhancing lesion on stable or increasing doses of corticosteroids compared with baseline scan or best response after initiation of therapy* not caused by comorbid events (e.g., radiation therapy, demyelination, ischemic injury, infection, seizures, postoperative changes, or other treatment effects); any new lesion; clear clinical deterioration not attributable to other causes apart from the tumor (e.g., seizures, medication adverse effects, complications of therapy, cerebrovascular events, infection, and so on) or changes in corticosteroid dose; failure to return for evaluation as a result of death or deteriorating condition; or clear progression of non-measurable disease. |

All measurable and non-measurable lesions must be assessed using the same techniques as at baseline. Abbreviations: MRI, magnetic resonance imaging; FLAIR, fluid-attenuated inversion recovery. * Stable doses of corticosteroids include patients not on corticosteroids Exclusion Criteria Pregnant or breastfeeding patients;

Evidence of CNS haemorrhage CTCAE grade 2 or above on baseline MRI;

Patients who suffered from an acute cardiac event within the last 12 months;

Patients with active vascular disease, either myocardial or peripheral (i.e. acute coronary syndrome, cerebral stroke, transient ischemic attack or arterial thrombosis or symptomatic peripheral vascular disease within the past 3 months);

Patients with known proliferative and/or vascular retinopathy;

Patients with known liver disease (alcoholic, drug/toxin induced, genetic, or autoimmune);

Patients that have undergone major surgery within the last 4 weeks before enrollment;

Minor surgical procedure, e.g. stereotactic biopsy, within 7 days of first study treatment; placement of a vascular access device, within 2 days of first study treatment;

History of intracranial abscess within 6 months prior to first study treatment;

History of active gastrointestinal bleeding within 6 months prior to first study treatment;

Serious, non-healing wound, active ulcer, or untreated bone fracture;

Treatment Plan

This study is a prospective, randomized, controlled, 2-arm, open label, multi-center, Phase 3 study, measuring the efficacy, safety, tolerability of multiple doses of intravenously administered VB-111 followed by VB-111 and bevacizumab as compared to bevacizumab monotherapy in patients with recurrent GBM.

Patients will be screened for eligibility and then, up to 28 days later, at the baseline visit, randomized to one of two treatment groups in a 1:1 ratio (investigative arm to control arm). Patients will be randomized and stratified according to age at randomization (≤60 years, <60 years), KPS (<80, ≥80) and progression (1st progression, 2nd progression). The intervention arm will receive monotherapy with VB-111 administered as multiple intravenous infusions of $1 \times 10^{13}$ VPs every 8 weeks, which will, upon progression, be combined with bevacizumab 10 mg/kg every 2 weeks. This regimen will continue until further progression. The control arm will receive monotherapy with bevacizumab 10 mg/kg every 2 weeks until progression.

The patients will remain in the study until discontinuation due to disease progression or withdrawal. Thereafter, follow-up for survival will continue until the patient expires.

An overview of the study is shown in FIG. 1.

Study Visits

Screening, Day −28-0 (All Patients)

Prospective patients will be screened within 4 weeks of enrollment. Patients will be informed of the advantages, risks and constraints of the study and will be asked to sign an informed consent form. Patients who have provided consent will be assigned an identification number which consists of the center number (e.g. 01) plus the subject/patient number in sequential order (e.g., 001, 002, 003, etc.). The full identification number for the first patient at center 01 will be 01-001, 01-002, etc.

Patients will proceed to screening assessments as shown in Example 2.

Baseline Visit Day 1 (All Patients)

Study treatment (VB-111 or bevacizumab) will be administered as an outpatient. Once the subject/patient is found eligible, he/she will be scheduled to arrive at the clinic within 4 weeks from screening in a fasting state until 30 minutes following study drug administration.

Prior to dosing (D1):

On the day of admission to the site, each subject/patient will be re-verified for eligibility according to inclusion/exclusion criteria and then tested within 24 hours prior to dosing for the following evaluations:

ADVERSE EVENTS: Patients will be asked about changes in their physical and mental status since signing the consent form.

CONCOMITANT MEDICATIONS: Patients will be asked about changes in their therapies since signing the consent form.

TUMOR MEASURE: Contrast and non-contrast brain MRI imaging will be done to assess extent of cancer. If there are less than 2 weeks between screening and baseline visits, only 1 MRI will be required.

LABORATORY ANALYSES:

Blood samples:
Hematology: hemoglobin, complete blood count with differential, INR, PT and activated PTT;
Chemistry: electrolytes, creatinine and blood urea nitrogen, bilirubin, alkaline phosphatase, ALT and AST, calcium, total protein and albumin;
Antibody to the Ad-5 virus sample.

Urine will be collected for the following evaluations:
Routine urinalysis
Dipstick for Proteinuria
No dose modifications for grade 1/2 events
Grade 3-(UPC>3.5, urine collection >3.5 g/24 hr, or dipstick 4+): Hold bevacizumab treatment until ≤Grade 2, as determined by either UPC ratio ≤3.5 or 24 hr collection ≤3.5 g
Grade 4 (nephrotic syndrome): Discontinue bevacizumab HEALTH-RELATED QUALITY OF LIFE ASSESSMENTS: EORTC core Quality of Life Questionnaire (QLQ-C30) and a Brain Cancer Module (BCM20) will be completed prior to receiving treatment.

RANDOMIZATION: Patients meeting all of the entry criteria will be randomized to one of two treatment groups in a 1:1 ratio, respectively, using a centralized randomization procedure: (1) VB-111 $1 \times 10^{13}$ VPs monotherapy every 8 weeks followed by, upon progression, VB-111 every 8 weeks and bevacizumab 10 mg/kg every 2 weeks or (2) Bevacizumab monotherapy: 10 mg/kg every 2 weeks. Randomization will be stratified according to age at randomization (≤60 years, <60 years), KPS (<80, ≥80) and progression ($1^{st}$ progression, $2^{nd}$ progression).

VITAL SIGNS: Vital signs (supine, systolic and diastolic blood pressure, peripheral heart rate, body temperature, respiration rate) will be recorded 15 minutes prior to dosing.

PROPHYLACTIC TREATMENTS: VB-111 RANDOMIZED PATIENTS: For patients randomized to the VB-111 treatment arm, the following prophylactic treatments will be administered:

ANTI-PYRETIC TREATMENT: To avoid fever following study drug administration, prior to treatment with VB-111 only all patients will receive 1000 mg of acetaminophen starting 1-2 hours prior to dosing followed by 500 mg PRN 24 hours.

CORTICOSTEROID TREATMENT: To reduce potential edema response during drug administration, dexamethasone treatment will be administered prior to treatment with VB-111 only:

Initial dose with VB-111: 10 mg will be administered 30 minutes prior to dosing, followed by 4 mg×2/day for 14 days post dosing.

Subsequent doses with VB-111: 10 mg will be administered 30 minutes prior to dosing, followed by 4 mg×2/day for 3 days post dosing. Further corticosteroid treatment will be administered at Investigator's discretion.

If patients begin the study already on steroids, all efforts should be made by the Investigator not to change the steroid dose within 5 days of disease assessment, unless clinically warranted. A decision to continue the steroids or to begin tapering after this period of time is at the discretion of the Investigator.

Study Drug Administration:

VB-111: Prior to infusion, the solution for injection should be brought to room temperature. Maximum time for drug in saline is 90 minutes at room temperature (60 minutes plus a 30 minute window). The vials should be opened in a biological safety cabinet and combined with saline (see VB-111 Infusion Preparation below). VB-111 will be infused to the patient at the relevant dosage according to the patient's weight, according to the Operations Manual. Specifically, for patients who weigh less than 50 Kg, the dose will be reduced by 30%. A single infusion of VB-111 should be administered at 3 ml/minute. Patients receiving VB-111 should remain in the clinic for 8 hours for observation.

BEVACIZUMAB: To be administered as standard of care (SOC).

VITAL SIGNS: VB-111 RANDOMIZED PATIENTS: The vital signs (systolic and diastolic blood pressure, peripheral heart rate, body temperature, respiration rate) will be recorded at 30 and 60 minutes after dosing and at 4 and 6 hours post dosing, and/or upon disappearance of any adverse event, whichever comes first.

ADVERSE EVENTS: Patients will be monitored for adverse events through their observation following treatment at the clinic.

CONCOMITANT MEDICATIONS: Any concomitant medications administered during the patients' observation following treatment should be recorded.

VB-111 Monotherapy Follow Up Visits

Safety Telephone Contact Every Other Month in Between Dosing Visits (Days 28, 84, 140, Etc.)

A telephone call should be made every other month in between dosing visits (days 28, 84, 140, etc.) to the subject/patient to inquire about AEs and changes in medication.

Further VB-111 Administration (Every 8 Weeks Following Initial Dose: Day 56, Day 112, Day 168, Etc.)

On the day of admission to the site, each subject/patient will be re-verified for eligibility according to inclusion/exclusion criteria (where applicable) and then tested within 24 hours prior to dosing. Patients without evidence of progressive disease will be considered for further dosing. This visit and VB-111 dosing will be repeated every 8 weeks until disease progression.

The following assessments will be performed:

ADVERSE EVENTS: Patients will be asked about changes in their physical and mental status since the last visit.

CONCOMITANT MEDICATIONS: Patients will be asked about changes in their therapies since the last visit.

HEALTH-RELATED QUALITY OF LIFE ASSESSMENTS: EORTC core Quality of Life Questionnaire (QLQ- C30) and a Brain Cancer Module (BCM20) will be completed prior to receiving treatment.

TUMOR MEASURE: Patients will be assessed for response using contrast and non-contrast brain magnetic resonance imaging (MRI) with assessment based on the RANO criteria. MRI imaging will be done up to 72 hours prior to dosing to assess the extent of cancer. (If the patient has confirmed disease progression, the patient should be considered for participation in the combination therapy with VB-111 and bevacizumab. VB-111 $1\times10^{13}$ VPs will be administered every 8 weeks and bevacizumab will be administered every 2 weeks.)

PHYSICAL EXAM: Physical Examination will focus on tumor organs and tumor measurements, according to RANO criteria, as well as the following: Head and neck; Eyes; Lungs; Heart; Abdomen; Joints; Peripheral circulation; Skin; or Neurologic.

ECG (Day 168 and Early Termination Only): A standard 12-lead electrocardiogram with rhythm strip should be performed.

Laboratory Analyses:
Blood samples will be collected for the following evaluations:
Hematology: hemoglobin, complete blood count with differential, INR, PT and activated PTT;
Chemistry: electrolytes, creatinine and blood urea nitrogen, bilirubin, alkaline phosphatase, ALT and AST, calcium, total protein and albumin;
Serum pregnancy test
Antibody to the Ad-5 virus sample.
Urine will be collected for the following evaluations:
Routine urinalysis
Dipstick for Proteinuria
  No dose modifications for grade 1/2 events
  Grade 3-(UPC>3.5, urine collection >3.5 g/24 hr, or dipstick 4+): Hold bevacizumab treatment until <Grade 2, as determined by either UPC ratio ≤3.5 or 24 hr collection ≤3.5 g
  Grade 4 (nephrotic syndrome): Discontinue bevacizumab VITAL SIGNS: Vital signs (supine, systolic and diastolic blood pressure, peripheral heart rate, body temperature, respiration rate) will be recorded 15 minutes prior to dosing.

ANTI-PYRETIC TREATMENT: To avoid fever following study drug administration, prior to treatment with VB-111 all patients will receive 1000 mg of acetaminophen 1-2 hours prior to dosing followed by 500 mg every 4 hours for 24 hours.

CORTICOSTEROID TREATMENT: To reduce potential edema response during drug administration, prior to treatment with VB-111 dexamethasone treatment will be administered: 10 mg will be administered 30 minutes prior to dosing, followed by 4 mg×2/day for 3 days post dosing. Further corticosteroid treatment will be administered at Investigator's discretion.

If the patient is on steroids at the time of dosing, all efforts should be made by the Investigator not to change the steroid dose within 5 days of disease assessment, unless clinically warranted. A decision to continue the steroids or to begin tapering after this period of time is at the discretion of the Investigator.

STUDY DRUG ADMINISTRATION: Infusion will be done according to the operation manual. Prior to infusion, the saline should be brought to room temperature. The vials should be opened in a biological safety cabinet and injected into normal saline for infusion according to the operation manual (see VB-111 Infusion Preparation) below. The final solution for administration should be administrated not more than 90 minutes after preparation (60 minutes plus a 30 minute window). VB-111 will be infused to the patient at the relevant dosage according to the patient's weight, as detailed in the Operations Manual. For patients less than 50 Kg of weight, the dose of $1\times10^{13}$ VPs will be reduced by 30%. The intravenous infusions of diluted VB-111 should be administered at 3 mL/minute A regular meal will be allowed 0.5 hour after dosing.

ADVERSE EVENTS: Patients will be monitored for adverse events through their observation following treatment at the clinic.

CONCOMITANT MEDICATIONS: Any concomitant medications administered during the patients' observation following treatment should be recorded.

End of VB-111 Monotherapy Upon Disease Progression

Patients will continue to receive VB-111 every 8 weeks provided that they continue to be stable. Once patients experience disease progression, they will return to the clinic for a final study visit. In addition, if patients withdraw consent or it is determined by the Investigator that the patient should not continue in the study, the patient will return for an Early Termination Visit. Patients will be contacted by telephone every 2-3 months to follow up on survival.

VB-111+Bevacizumab Administration as Combination Treatment

At the time the patient experiences disease progression, the subject/patient will initiate treatment with VB-111 and bevacizumab as a combination therapy. VB-111 $1\times10^{13}$ VPs will be administered every 8 weeks and bevacizumab will be administered every 2 weeks.

Since a minimum of 8 weeks is required between doses of VB-111, if a subject/patient progresses before 8 weeks, the subject will begin treatment with bevacizumab (10 mg/kg) every 2 weeks and at 8 weeks from the last dose of VB-111, the subject/patient will receive the first combination dose with VB-111.

Patients will be re-informed of the advantages, risks and constraints of the combination therapy. The following assessments will be performed on each day of combination treatment:

ADVERSE EVENTS: Patients will be asked about changes in their physical and mental status since the last visit.

CONCOMITANT MEDICATIONS: Patients will be asked about changes in their therapies since the last visit.

HEALTH-RELATED QUALITY OF LIFE AND NEUROCOGNITIVE FUNCTION: EORTC core Quality of Life Questionnaire (QLQ-C30) and a Brain Cancer Module (BCM20) will be completed prior to receiving treatment.

TUMOR MEASURE: Patients will be assessed for response using contrast and non-contrast brain magnetic resonance imaging (MRI) with assessment based on the RANO criteria. MRI imaging will be done up to 72 hours prior to dosing to assess extent of cancer.

PHYSICAL EXAM: Physical Examination will focus on tumor organs and tumor measurements, according to RANO criteria, as well as the following: Head and neck; Eyes; Lungs; Heart; Abdomen; Joints; Peripheral circulation; Skin; or Neurologic VITAL SIGNS: Vital signs (supine, systolic and diastolic blood pressure, peripheral heart rate, body temperature, respiration rate) will be recorded 15 minutes prior to dosing.

ECG (to be performed every 6 months from the initial combination dose): A standard 12-lead electrocardiogram with rhythm strip should be performed.

Laboratory Analyses:

Blood sample will be collected for the following evaluations:

Hematology: hemoglobin, complete blood count with differential, INR, PT and activated PTT;

Chemistry: electrolytes, creatinine and blood urea nitrogen, bilirubin, alkaline phosphatase, ALT and AST, calcium, total protein and albumin;

Serum pregnancy test;

Antibody to the Ad-5 virus sample.

Urine will be collected for the following evaluations:

Routine urine analysis

Dipstick for Proteinuria

No dose modifications for grade 1/2 events

Grade 3-(UPC>3.5, urine collection >3.5 g/24 hr, or dipstick 4+): Hold bevacizumab treatment until ≤Grade 2, as determined by either UPC ratio ≤3.5 or 24 hr collection ≤3.5 g Grade 4 (nephrotic syndrome): Discontinue bevacizumab ANTI-PYRETIC TREATMENT: To avoid fever following study drug administration, prior to treatment with VB-111 all patients will receive 1000 mg of acetaminophen 1-2 hours prior to dosing followed by 500 mg every 4 hours for 24 hours.

CORTICOSTEROID TREATMENT: To reduce potential edema response during drug administration, prior to treatment with VB-111 dexamethasone treatment will be administered: 10 mg will be administered 30 minutes prior to dosing, followed by 4 mg×2/day for 3 days post dosing. Further corticosteroid treatment will be administered at Investigator's discretion.

If the patient is on steroids at the time of dosing, all efforts should be made by the Investigator not to change the steroid dose within 5 days of disease assessment, unless clinically warranted. A decision to continue the steroids or to begin tapering after this period of time is at the discretion of the Investigator.

BEVACIZUMAB ADMINISTRATION: Bevacizumab will be administered by infusion at a dose of 10 mg/kg before VB-111 on dosing days. The rate of infusion shall be according to the package insert for bevacizumab: Bevacizumab should be delivered over 60 minutes (+30 minute window) as an IV infusion. If the 60-minute infusion is tolerated, all subsequent infusions may be administered over 30 minutes.

VB-111 ADMINISTRATION: Infusion will be done according to the operation manual. Prior to infusion, the saline should be brought to room temperature. The vials should be opened in a biological safety cabinet and injected into normal saline for infusion according to the operation manual (see VB-111 Infusion Preparation below). The final solution for administration should be administered not more than 90 minutes after preparation (60 minutes plus a 30 minute window). VB-111 will be infused to the patient at the relevant dosage according to the patient's weight, as detailed in the Operations Manual. For patients less than 50 Kg of weight, the dose of $1\times10^{13}$ VPs will be reduced by 30%. The intravenous infusions of diluted VB-111 should be administered at 3 mL/minute.

VITAL SIGNS: For the initial combination dose, vital signs (systolic and diastolic blood pressure, peripheral heart rate, body temperature, respiration rate) will be recorded at 30 and 60 minutes after dosing and at 4 and 6 hours post dosing, and/or upon disappearance of any adverse event, whichever comes first. For further doses, vital signs should be recorded 15 minutes prior to dosing and 30 minutes following dosing ADVERSE EVENTS: Patients will be monitored for adverse events through their observation following treatment at the clinic.

CONCOMITANT MEDICATIONS: Any concomitant medications administered during the patients' observation following treatment should be recorded.

Follow Up: Combination Treatment with VB-111 and Bevacizumab:

Bi-Weekly Treatment with Bevacizumab

Bevacizumab will be administered according to standard of care practices every 2 weeks. It is preferred that the subject/patient visit the study clinic to receive this treatment and be seen by the Investigator to assess safety (via collection of adverse event and concomitant medication information). However, if the subject/patient lives more than 1 hour commute from the clinic, the subject/patient may receive this treatment from his/her local oncologist and safety information (collection of adverse event and concomitant medication information) should be transferred to the study clinic for inclusion into study records. Local visits should be pre-approved by the Medical Monitor on a per patient basis.

Days Following Initial Combination Treatment

One month following the initial combination treatment, each patient will be required to return to the clinic in a fasting state, for the following evaluations:

ADVERSE EVENTS: Patients will be asked about changes in their physical and mental status since the last visit.

CONCOMITANT MEDICATIONS: Patients will be asked about changes in their therapies since the last visit.

VITAL SIGNS: Vital signs (supine systolic and diastolic blood pressure, peripheral heart rate, body temperature, respiration rate) will be recorded.

Laboratory Analyses:

Blood sample will be collected for the following evaluations:

Hematology: hemoglobin, complete blood count with differential, INR, PT, and activated PTT Chemistry: electrolytes, creatinine and blood urea nitrogen, bilirubin, alkaline phosphatase, ALT and AST, calcium, total protein and albumin Antibody to the Ad-5 virus sample.

Laboratory samples drawn in response to a clinically significant event will be documented as unscheduled laboratory evaluations.

Urine sample will be collected for the following evaluations:

Routine urinalysis

Dipstick for Proteinuria

No dose modifications for grade 1/2 events

Grade 3-(UPC>3.5, urine collection >3.5 g/24 hr, or dipstick 4+): Hold bevacizumab treatment until ≤Grade 2, as determined by either UPC ratio ≤3.5 or 24 hr collection ≤3.5 g Grade 4 (nephrotic syndrome): Discontinue bevacizumab Study Therapy Termination: Combination Treatment with VB-111 and Bevacizumab Patients will continue to receive VB-111 every 8 weeks and bevacizumab every 2 weeks, provided that they continue to be stable. Visits will continue on days of combination treatment (every 8 weeks). Once patients experience disease progression, they will return to the clinic for a final study visit (see below). In addition, if patients withdraw consent or it is determined by the Investigator that the patient should not continue in the study, the patients will return for a final study visit. Patients will be contacted every 2-3 months to follow up on survival.

Follow up will continue until the patient expires.

Bevacizumab Administration as Monotherapy

Bi-Weekly Treatment with Bevacizumab (Days 14, 28, 42 . . . 70, 84, 98, Etc.)

BEVACIZUMAB ADMINISTRATION: Bevacizumab will be administered biweekly by infusion at a dose of 10 mg/kg according to standard of care practices. During the visits to the clinic to receive this treatment, the subject/patient should be seen by the Investigator to assess safety.

ADVERSE EVENTS: Patients will be asked about changes in their physical and mental status since signing the consent form.

CONCOMITANT MEDICATIONS: Patients will be asked about changes in their therapies since signing the consent form.

Bevacizumab Treatment (Days 56, 112, 168, etc.)

The following assessments will be performed:

ADVERSE EVENTS: Patients will be asked about changes in their physical and mental status since the last visit.

CONCOMITANT MEDICATIONS: Patients will be asked about changes in their therapies since the last visit.

HEALTH-RELATED QUALITY OF LIFE: EORTC core Quality of Life Questionnaire (QLQ-C30) and a Brain Cancer Module (BCM20) will be completed at each visit prior to receiving treatment.

TUMOR MEASURE: Patients will be assessed for response using contrast and non-contrast brain magnetic resonance imaging (MRI) with assessment based on the RANO criteria. MRI imaging will be done up to 72 hours prior to dosing to assess extent of cancer.

PHYSICAL EXAM: Physical Examination will focus on tumor organs and tumor measurements, according to RANO criteria, as well as the following: Head and neck; Eyes; Lungs; Heart; Abdomen; Joints; Peripheral circulation; Skin; or Neurologic.

ECG (to be performed 6 months from the initial bevacizumab dose): A standard 12-lead electrocardiogram with rhythm strip should be performed.

LABORATORY ANALYSES (according to the operation manual):

Blood sample will be collected for the following evaluations:
  Hematology: hemoglobin, complete blood count with differential, INR, PT and activated PTT;
  Chemistry: electrolytes, creatinine and blood urea nitrogen, bilirubin, alkaline phosphatase, ALT and AST, calcium, total protein and albumin;
  Serum pregnancy test
  Antibody to the Ad-5 virus sample.
  Urine will be collected for the following evaluations:
  Routine urine analysis
  Dipstick for proteinuria
    No dose modifications for grade 1/2 events
    Grade 3-(UPC>3.5, urine collection >3.5 g/24 hr, or dipstick 4+): Hold bevacizumab treatment until ≤Grade 2, as determined by either UPC ratio ≤3.5 or 24 hr collection ≤3.5 g
  Grade 4 (nephrotic syndrome): Discontinue bevacizumab VITAL SIGNS: Vital signs (supine, systolic and diastolic blood pressure, peripheral heart rate, body temperature, respiration rate) will be recorded 15 minutes prior to dosing.

BEVACIZUMAB ADMINISTRATION: Bevacizumab will be administered by infusion at a dose of 10 mg/kg before VB-111 on dosing days. The rate of infusion shall be according to the package insert for bevacizumab: The initial bevacizumab dose should be delivered over 60 minutes (+30 minute window) as an IV infusion.

Study Completion/Early Termination: Monotherapy with Bevacizumab:

Patients will continue to receive bevacizumab every 2 weeks, provided that they continue to be stable. Visits will continue every 8 weeks. Once patients experience disease progression, they will return to the clinic for a final study visit (see Section 4.5). In addition, if patients withdraw consent or it is determined by the Investigator that the patient should not continue in the study, the patient will return for a final visit.

Patients will be contacted every 2-3 months to follow up on survival.

Follow up will continue until the patient expires.

Study Therapy Termination (All Therapies)

At the time the subject/patient has been withdrawn from the trial, due to consent withdrawal or disease progression the following assessments will be performed as a final study visit:

ADVERSE EVENTS: Patients will be asked about changes in their physical and mental status since the last visit.

CONCOMITANT MEDICATIONS: Patients will be asked about changes in their therapies since the last visit.

HEALTH-RELATED QUALITY OF LIFE AND NEUROCOGNITIVE FUNCTION: EORTC core Quality of Life Questionnaire (QLQ-C30) and a Brain Cancer Module (BCM20) will be completed.

TUMOR MEASURE Patients will be assessed for response using contrast and non-contrast brain magnetic resonance imaging (MRI) with assessment based on the RANO criteria.

PHYSICAL EXAM: Physical Examination will focus on tumor organs and tumor measurements, according to RANO criteria, as well as the following: Head and neck; Eyes; Lungs; Heart; Abdomen; Joints; Peripheral circulation; Skin; or Neurologic ECG: A standard 12-lead electrocardiogram with rhythm strip should be performed.

Laboratory Analyses:

Blood sample will be collected for the following evaluations:
  Hematology: hemoglobin, complete blood count with differential, INR, PT and activated PTT
  Chemistry: electrolytes, creatinine and blood urea nitrogen, bilirubin, alkaline phosphatase, ALT and AST, calcium, total protein and albumin;
  Serum pregnancy test
  Antibody to the Ad-5 virus sample.
  Urine will be collected for the following evaluations:
  Routine urine analysis
  Dipstick for Proteinuria VITAL SIGNS: Vital signs (supine, systolic and diastolic blood pressure, peripheral heart rate, body temperature, respiration rate) will be recorded.

Duration of Study

The patients will remain in the study until discontinuation due to disease progression or early termination. Thereafter, the patient will be contacted by telephone survival data every 2-3 months until the patient expires.

Correlative/Special Studies

Antibodies

Serum samples will be collected for analysis of levels of antibodies to the adenovirus.

Measurement of Effect
Overall Survival

Overall survival is defined as the time from first dose of study medication until death from any cause. Patients will be followed for survival status after completion or removal from the study for progression or toxicity.

Tumor measurement: Tumor response will be assessed using the same criteria described in Example 2.

Guidelines for Evaluation of Measurable Disease: The Guidelines described in Example 2 will be followed.

Response Criteria: Response criteria will be assessed using the same criteria described in Example 2.

Confirmatory Measurement/Duration of Response

Confirmation: To be assigned a status of PR or CR, changes in tumor measurements must be confirmed by repeat assessments that should be performed 4 weeks after the criteria for response are first met.

Duration of Overall Response: The duration of overall response is measured from the time measurement criteria are met for CR or PR (whichever is first recorded) until the first date that recurrent or progressive disease is objectively documented (taking as reference for progressive disease the smallest measurements recorded since the treatment started).

The duration of overall CR is measured from the time measurement criteria are first met for CR until the first date that recurrent disease is objectively documented.

Duration of Stable Disease: Stable disease is measured from the start of the treatment until the criteria for progression are met, taking as reference the smallest measurements recorded since the treatment started.

Exploratory Assessments

Optional Biopsy Samples: Biopsies of brain tissue (preferably fresh frozen samples) may be collected for further testing by VBL as part of a clinically indicated procedure at any time in the study. If a sample of brain tissue is collected, a blood sample for transgene analysis should be collected on the same day.

Statistical Considerations
Study Design

Objectives: To evaluate the safety, tolerability and efficacy of multiple doses of VB-111 $1 \times 10^{13}$ viral particles [VPs] Q2 months as monotherapy, combined with bevacizumab 10 mg/Kg every 2 weeks upon progression compared to bevacizumab monotherapy in patients with recurrent GBM.

All data collected will be summarized and presented. Continuous variables will be described as the mean, median, standard deviation and range of n observations. Categorical data will be described with contingency tables including frequency and percentage. Individual subject/patient listings will be generated and presented.

All patients meeting the eligibility criteria who signed a consent form and have received VB-111 and/or bevacizumab will be considered evaluable for safety and efficacy analysis.

Statistical descriptions and analyses will be carried out using SAS statistical analysis software (SAS Institute, Inc., Cary, N.C., USA).

Study Endpoints

Primary Efficacy Endpoint: Overall Survival (OS), is defined as the time from first dose of study medication until death from any cause. Patients will be followed for survival status after completion or removal from the study for progression or toxicity.

Secondary Efficacy Endpoints: Progression Free Survival (PFS) is defined as the time from first dose of study medication until objective tumor progression, assessed according to RANO. Tumor response is measured by RANO Criteria including complete response, partial response, stable disease and progression.

Tertiary Efficacy Endpoints: Tumor growth rate is defined by the rate of change (slope) of tumor size in each subject/patient. Tumor size will be determined as the product of the perpendicular dimensions of the tumor.

Health-Related Quality of Life and Neurocognitive Function [EORTC core Quality of Life Questionnaire (QLQ-C30) and Brain Cancer Module (BCM20)]

Safety and Tolerability Endpoints: adverse events, vital signs, physical examinations, laboratory evaluations, and electrocardiogram (ECG).

Statistical Methods

All data collected will be summarized and presented. Continuous variables will be described as the mean, median, standard deviation, minimum and maximum. Categorical data will be described with contingency tables including frequency and percentage. Individual subject/patient listings of all data will be generated and presented.

Statistical descriptions and analyses will be carried out using SAS statistical analysis software (SAS Institute, Inc., Cary, N.C., USA).

Study Populations

The intention to treat population (ITT) will include all patients meeting the eligibility criteria who have signed a consent form and have received VB-111 will be considered evaluable for safety and efficacy analyses.

In one aspect, efficacy analyses will also be completed in a Per-Protocol population. These analyses will be exploratory and will be defined in the Statistical Analysis Plan.

In another aspect, all patients who received at least one repeat dose of $1 \times 10^{13}$ VPs of VB-111 will be considered evaluable and included in all efficacy analyses.

Demographic and Baseline Parameters

Demographic and baseline parameters including sex, age, height and weight, details of initial diagnosis and treatment history will be summarized overall and by treatment group. Stratification parameters including age ($\leq 60$ years, $>60$ years), KPS ($<80$, $\geq 80$), and progression history ($1^{st}$ progression, $2^{nd}$ progression) will be summarized overall by treatment group. All continuous variables will be summarized by descriptive statistics. All discrete variables will be summarized by frequencies and percentages.

Study Duration and Compliance

All study drug administration and compliance data will be summarized.

Prior and Concomitant Medication

All relevant prior medication and all concomitant medications will be summarized by frequencies and percentages. All medications will be coded using the World Health Organization (WHO) drug dictionary.

Efficacy Analyses
Primary Efficacy Analysis

Overall survival rates including median survival time and 12 month survival rate will be estimated using the Kaplan-Meier method. OS will be measured from the time of the first dose until death or until the last known date on which the patient was alive. Patients will be followed for survival status after completion or removal from the study for progression or toxicity until death. For patients who have not died at the time of analysis, survival data will be censored at the patient's last known alive date. The log rank test will be used to compare the survival distributions of the two treatment groups. In another aspect, the Cox Regression model with the stratification variables as adjusting covariates will be used to compare the survival distributions of the two treatment groups.

Secondary Efficacy Analyses

Progression free survival rates will be estimated using the Kaplan-Meir method. PFS will be measured from the time of the first dose to the date of first progression or death or until the last known date on which the patient was stable. Patients will be followed for progression status after completion of the study. The log rank test will be used to compare the survival distributions of the two treatment groups. In another aspect, the Cox Regression model with the stratification variables as adjusting covariates will be used to compare the survival distributions of the two treatment groups.

Tumor response will be assessed every 2 months until disease progression. The proportion of patients who had complete response, partial response, stable disease and progression will be summarized at each visit by treatment group. Differences between the proportions in each group will be tested using a Chi Square test. In another aspect, differences between the proportions in each group will be tested using a Cochran Mantel Haenszel (CMH) test controlling for age, KPS, and progression history.

Tertiary Efficacy Analyses

Tumor measurements will be taken every 2 months until disease progression. Tumor growth rate will be determined by calculating the change and percent change from baseline of the tumor size at each visit. The rate of change (slope) of each patient will be calculated and summarized by treatment group. The difference in log transformed tumor growth rate will be compared between the treatment group using the 2 sample T test or Wilcoxon non parametric test, as appropriate.

Subgroup Analyses

Subgroup analysis for the primary and secondary efficacy endpoints will be performed for the following categories:
  Age (≤60, >60);
  KPR (<80, ≥80);
  First or second disease progression;
  Residual tumor size post the initial surgical resection (cutoff will be determined prior to study unblinding);
  Tumor size at study enrollment (cutoff will be determined prior to study unblinding);
  MGMT mutation status;
  Gender
  Country The detailed definitions of the subgroup analyses will be outlined in the statistical analysis plan. The approach to inference will be a conservative one, based on interactions between treatment group and subgroup category, and adjusting for multiple comparisons.

Safety and Toxicity Analyses

Adverse events monitoring and clinical findings including physical examinations, vital signs, laboratory test results, concomitant medications, and withdrawals/terminations will be used to assess safety.

Adverse Events

AEs will be categorized by SOC and Preferred Terms using the MedDRA dictionary. The incidence of AEs as well as the severity and relationship to study drug will be presented by treatment group. The incidence of AEs leading to withdrawal from the study and serious AEs (SAES) will be summarized by frequency and percentages.

As per NCI CTCAE Version 4.0, the term toxicity is defined as adverse events that are classified as either possibly, probably, or definitely related to study treatment. The maximum grade for each type of toxicity will be recorded for each patient and will be used for reporting. Frequency tables will be reviewed to determine toxicity patterns. In addition, all adverse event data graded as 3, 4, or 5 and classified as either "unrelated or unlikely to be related" to study treatment in the event of an actual relationship developing will be reviewed.

Serious adverse events will be similarly summarized.

Infusional adverse events will also be summarized by both the investigator's and the sponsor's assessment of causality.

Clinical findings will include evaluation of physical examinations, vital signs and laboratory test results, concomitant medications, and withdrawals/terminations. These findings will be summarized by treatment group. Continuous variables will be described as the mean, median, standard deviation, and range of n observations. Categorical data will be described with contingency tables including frequency and percent.

Interim Analysis

A Data and Safety Monitoring Committee (DSMC) will be appointed to review the data on safety and efficacy as they accumulate.

Data on adverse outcomes will be reviewed on an ongoing basis. The committee will meet at regular intervals to be agreed upon by the members of the committee and the sponsor.

The final analysis of the results will be conducted after all patients have been followed for at least 12 months. A single formal interim analysis will be conducted 8 months before the planned final analysis, when it is calculated that 60% of the expected total number of events will have accrued. The statistical guideline for the committee to recommend early termination of the trial due to efficacy/futility will be based on attainment of a statistically significant difference in the direction of benefit to VBL-111 at the two-sided 0.003 level.

Under the stopping rule, computer simulations show that in order to preserve the overall two-sided 0.05 level, the final analysis should use a two-sided 0.0493 level instead of 0.05.

In another aspect, the statistical guideline for the committee to recommend early termination of the trial due to efficacy/futility will be based on the conditional probability (under the alternative hypothesis) of attaining a statistically significant result at the end of the trial being less than 0.05. Under this futility stopping rule, the significance level of the final analysis will remain at the two-sided level of 0.05, because futility analyses do not increase the probability of a type I error in the direction of advantage to the experimental treatment.

At the time of this interim analysis, the Data and Safety Monitoring Committee will provide the sponsor with the estimated Kaplan-Meir survival curves for the two treatment groups together with the estimated hazard ratio and two-sided p-value for the comparison.

Power and Significance Level

The trial is planned to enroll 252 subjects/patients, who will be randomized to VB-111 vs. bevacizumab, at a 1:1 ratio. See FIG. 1. The final analysis of the results will be conducted after all patients have been followed for at least 12 months. The expected number of deaths that will have been observed at that time is 151, under the assumption that recruitment of all patients will be achieved at a uniform rate over 12 months. If recruitment takes longer than 12 moths or recruitment rates, instead of being uniform, increase as the trial proceeds, then the expected number of deaths will be larger than 151. The sample size justification is described below:

Assuming a proportional hazards model, the hazard ratio is calculated as the ratio of the logarithms of the survival rates (at any time). Assuming a 37.6% 12 month survival rate in the bevacizumab treatment group (based on bevacizumab study) and a 55% 12 month survival rate in the VB-111 group (based on the 12 patients treated at high dose of VB-111 reported above), the hazard ratio $\lambda = \ln(0.55)/\ln(0.376) = 0.611$.

It is expected that this study will recruit patients for 12 months and then follow up for 12 months.

A single formal interim analysis will be conducted after 60% of the expected total number of events will have accrued. In order to preserve an overall two-sided 0.05 significance level, the final analysis will use a two-sided 0.0493 level instead of 0.05. Based on the bevacizumab study and, where necessary, on exponential decay extrapolations, the percentage of deaths observed in the bevacizumab group is expected to be 75.4%. Given the hazard ratio of 0.611, the percentage of deaths observed in the VB-111 group is expected to be 58%.

The final analysis will compare the survival curves of bevacizumab versus VB-111 using the Logrank Test. In order to calculate the required sample size, the following formula was used:

$$\frac{1}{d_1} + \frac{1}{d_2} = \frac{(\ln \lambda)^2}{(z_\alpha + z_\beta)^2} \quad (1)$$

where
$d_1$ = number of deaths observed in VB-111 group
$d_2$ = number of deaths observed in the bevacizumab group
$\lambda$ = assumed hazard ratio = 0.611
$z_\alpha$ = standard normal deviate for two-sided significance level of 4.93% (adjusted for the interim analysis to preserve the overall 5% level) = 1.966
$z_\beta$ = standard normal deviate for statistical power of 85% = 1.0364 Given:
$d_1 = p_1 \times n_1$, where $n_1$ is the sample size in the VB-111 group;
$d_2 = p_2 \times n_2$, where $n_2$ is the sample size in the bevacizumab group;
$p_1$ = overall proportion of deaths expected to be observed in the VB-111 group = 0.58;
$p_2$ = overall proportion of deaths expected to be observed in the bevacizumab group = 0.754; and $n_1 = n_2$
Solve formula (1) for $n_1$ and $n_2$.
These numbers were divided by 0.9 to account for a 10% drop-out rate.

Based on the assumptions above, a sample size of 126 patients in the bevacizumab group and 126 patients in the VB-111 group, giving a total of 252 patients will be required. (FIG. 1).

VB-111 Infusion Preparation

Drug Description

Study drug vials will be supplied for each patient in labeled 1.8 ml cryovials (polypropylene) or 10 ml borosilicate vials. Each cryovial contains a volume of 1.1 ml (1012 VP/ml). Each borosilicate vial contains a volume of 5.3 ml (1012 VP/ml). The drug will be stored in the pharmacy at or below −65° C. The patient information (Patient number, Visit Date) should be added by hand to the label using a permanent ink marker and recorded in the patient records.

Procedure Prior to Infusion

The entire process of drug preparation shall be carried out at room temperature in the BSC type II room. After thawing, the drug may be maintained up to 3 hours in ice water during preparations. The drug is diluted in room temperature saline. The preparation of the drug and drug injection shall be completed within 1 hour, with a window of 30 minutes (for a maximum time of 90 minutes).

The pharmacist preparing the drug shall verify that the information on the container is appropriate for the study and for the patient: product name, concentration, batch number.

For each patient, use the appropriate syringe as specified in Table 9. Place volume needed of saline (brought to room temperature) in a 50 ml sterile plastic tube. Thaw the vials of VB-111 solution by rubbing between the gloved hands. Be sure to mark the time of thaw.

Using a 10 ml syringe, pull 1 ml of VB-111 from each of the cryovial or 5 ml from the borosilicate vial intended for the specific patient. Add VB-111 to the plastic tube containing the saline solution prepared in advance. Draw the piston to mix the remaining VB-111 in the syringe with saline and push it back into the plastic tube. Mix the diluted drug by swirling the contents by hand. Determine the volume to be applied according to the patient's weight and draw the required volume for injection into the syringe for administration.

After completing the preparation, perform a reconciliation process: check that the correct number of source vials was used; and record vials assigned to the patient in the drug accountability log.

After preparation of the drug solution, clean the drug formulation area in the pharmacy according to the pharmacy procedures.

VB-111 Infusion

Patients should receive VB-111 in a fasting state. "A fasting state" means that the patient has had nothing to eat or drink for at least the previous 2 hours.

A single intravenous infusion of the diluted VB-111 should be administered according to the instructions below at 3 ml/minute.

An infusion pump may be used. A regular meal may be provided to the patient 30 minutes after completion of dosing. On dosing days where the patient is treated with both VB-111 and bevacizumab, bevacizumab shall be prepared and dosed prior to VB-111.

TABLE 9

| VB-111 Preparation | | |
|---|---|---|
| Dose | $1 \times 10^{13}$ | $1 \times 10^{13}$ |
| Concentration in vial (VP/ml) | $10^{12}$ | $10^{12}$ |
| Volume of VB-111 in tube | 1.1 ml | 5.3 ml |
| # Vials of VB-111 | 10 | 2 |
| Take this volume of VB-111 | 10 × 1 ml | 2 × 5 ml |
| Syringe Type for VB-111 | 10 ml | 10 ml |
| Volume of saline | 40 ml | 40 ml |
| Tube type for saline | 50 ml* | 50 ml* |
| Total volume prepared | 50 ml | 50 ml |
| Volume to inject patient weight ≥50 kg | Entire volume (50 ml) | Entire volume (50 ml) |
| Volume to inject patient weight <50 kg | 35 ml** | 35** |

*The pharmacy may alternatively use a sterile empty bag and add 40 ml NS + 10 ml VB-111 to the bag, or the pharmacy can use a 50 ml bag of NS and remove the excess volume then add the VB-111. Either way is an acceptable pharmacy practice.
**35 ml for patients <50 kg represents a 30% reduction of VB-111 mixed with saline, in accordance with the Protocol, "Study Drug Administration."?

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The present application claims priority to U.S. provisional Application No. 61/760,601, filed Feb. 4, 2013, U.S. provisional Application No. 61/800,716, filed Mar. 15, 2013; U.S. provisional Application No. 61/858,467, filed Jul. 25, 2013; and U.S. provisional Application No. 61/907,286, filed Nov. 21, 2013, all of which are incorporated herein by reference in their entireties.

What is claimed:

1. A method of inducing apoptosis of an endothelial cell in a tumor of a subject in need thereof comprising:
   (i) administering to the subject a vector consisting of the nucleotide sequence set forth in SEQ ID NO: 19, wherein the responsiveness of the subject to a VEGF antagonist is increased after the administration of the vector, and
   (ii) administering a VEGF antagonist to the subject, wherein the tumor size or tumor growth in the subject is reduced after administration of the VEGF antagonist.

2. The method of claim 1, wherein the VEGF antagonist is an anti-VEGF antibody or a VEGF binding molecule.

3. The method of claim 2, wherein the anti-VEGF antibody is a monoclonal antibody, a humanized antibody, a human antibody, a single chain antibody, or a chimeric antibody.

4. The method of claim 3, wherein the anti-VEGF antibody is bevacizumab.

5. The method of claim 1, wherein the vector is administered at an effective amount of about $1\times10^{11}$ virus particles to about $1\times10^{14}$ virus particles.

6. The method of claim 4, wherein the bevacizumab is administered at an effective amount of about 1 mg/kg to about 15 mg/kg.

7. The method of claim 4, wherein the vector is administered at an effective amount of about $1\times10^{12}$ to about $1\times10^{13}$ virus particles and bevacizumab is administered at an effective amount of 5 mg/kg to 15 mg/kg.

8. The method of claim 2, wherein the vector is repeatedly administered.

9. The method of claim 4, wherein the bevacizumab is repeatedly administered.

10. The method of claim 4, wherein the vector is repeatedly administered every 2 months and the bevacizumab is repeatedly administered every 2 weeks.

11. The method of claim 1, wherein the tumor is a metastatic tumor.

12. The method of claim 1, wherein the tumor is associated with Leukemia, Hodgkin's Disease, Non-Hodgkin's Lymphoma, multiple myeloma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, premalignant skin lesions, testicular cancer, lymphomas, thyroid cancer, papillary thyroid cancer, neuroblastoma, neuroendocrine cancer, esophageal cancer, genitourinary tract cancer, malignant hypercalcemia, cervical cancer, endometrial cancer, adrenal cortical cancer, prostate cancer, Mullerian cancer, ovarian cancer, peritoneal cancer, fallopian tube cancer, uterine papillary serous carcinoma, metastatic colorectal cancer (mCRC), advanced nonsquamous non-small cell lung cancer (NSCLC), metastatic renal cell carcinoma (mRCC), or glioblastoma multiforme (GBM).

13. A method of inhibiting or reducing angiogenesis in a tumor of a subject in need thereof comprising:
   (i) administering to the subject a vector consisting of the nucleotide sequence set forth in SEQ ID NO: 19, wherein the responsiveness of the subject to a VEGF antagonist is increased after the administration of the vector, and (ii) administering a VEGF antagonist to the subject, wherein the disease or condition in the subject is treated after administration of the VEGF antagonist.

14. The method of claim 13, wherein the tumor is associated with Leukemia, Hodgkin's Disease, Non- Hodgkin's Lymphoma, multiple myeloma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, premalignant skin lesions, testicular cancer, lymphomas, thyroid cancer, papillary thyroid cancer, neuroblastoma, neuroendocrine cancer, esophageal cancer, genitourinary tract cancer, malignant hypercalcemia, cervical cancer, endometrial cancer, adrenal cortical cancer, prostate cancer, Mullerian cancer, ovarian cancer, peritoneal cancer, fallopian tube cancer, uterine papillary serous carcinoma, metastatic colorectal cancer (mCRC), advanced nonsquamous non-small cell lung cancer (NSCLC), metastatic renal cell carcinoma (mRCC), or glioblastoma multiforme (GBM).

15. A method of identifying a candidate for a VEGF antagonist therapy comprising:

measuring a tumor size of a subject who is diagnosed as having a tumor prior to administering a vector which consists of the nucleotide sequence set forth in SEQ ID NO: 19, wherein progression of the tumor after the administration of the vector is measured by magnetic resonance imaging (MRI), and the tumor is determined to be progressed when the tumor has grown after the administration of the vector, wherein the subject is identified as a candidate for a VEGF antagonist therapy after the tumor has progressed, and a VEGF antagonist therapy is administered to the patient.

16. The method of claim 15, wherein the anti-VEGF antibody is bevacizumab.

\* \* \* \* \*